(12) United States Patent
Wang

(10) Patent No.: US 12,344,854 B2
(45) Date of Patent: Jul. 1, 2025

(54) METHODS AND COMPOSITIONS FOR PLANT PATHOGEN RESISTANCE IN PLANTS

(71) Applicant: UNIVERSITY OF FLORIDA RESEARCH FOUNDATION, INC., Gainesville, FL (US)

(72) Inventor: Nian Wang, Auburndale, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 18/089,985

(22) Filed: Dec. 28, 2022

(65) Prior Publication Data

US 2024/0132907 A1 Apr. 25, 2024

Related U.S. Application Data

(62) Division of application No. 16/761,409, filed as application No. PCT/US2018/059269 on Nov. 5, 2018, now Pat. No. 11,634,725.

(60) Provisional application No. 62/627,496, filed on Feb. 7, 2018, provisional application No. 62/581,491, filed on Nov. 3, 2017.

(51) Int. Cl.
*C12N 15/82* (2006.01)

(52) U.S. Cl.
CPC ............................. *C12N 15/8281* (2013.01)

(58) Field of Classification Search
None
See application file for complete search history.

(56) References Cited

U.S. PATENT DOCUMENTS

| | | |
|---|---|---|
| 5,384,253 A | 1/1995 | Krzyzek et al. |
| 5,459,252 A | 10/1995 | Conkling et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,591,616 A | 1/1997 | Hiei et al. |
| 5,610,042 A | 3/1997 | Chang et al. |
| 9,322,006 B2 | 4/2016 | Liu et al. |
| 9,389,230 B2 * | 7/2016 | Ma .................... G01N 33/581 |
| 11,634,725 B2 * | 4/2023 | Wang ................ C12N 15/8281 800/279 |
| 2011/0119788 A1 | 5/2011 | Rodriguez Baixauli et al. |
| 2015/0203871 A1 | 7/2015 | Juillerat et al. |
| 2016/0369301 A1 | 12/2016 | Church et al. |
| 2017/0106025 A1 | 4/2017 | Kovarik |
| 2017/0191082 A1 | 7/2017 | Chen et al. |

FOREIGN PATENT DOCUMENTS

| | | |
|---|---|---|
| EP | 0154204 A2 | 9/1985 |
| WO | 199409699 A1 | 5/1994 |
| WO | 1997041228 A3 | 11/1997 |
| WO | 2019090261 A1 | 5/2019 |

OTHER PUBLICATIONS

Pang et al (Citrus CsACD2 Is a Target of Candidatus Liberibacter Asiaticus in Huanglongbing Disease. Plant Physiology, vol. 184, pp. 792-805, 2020) (Year: 2020).*
Gray et al (A Novel Suppressor of Cell Death in Plants Encoded by the Lls1 Gene of Maize. Cell, vol. 89, 25-31, Apr. 4, 1997). (Year: 1997).*
Zhou et al (Diversity and Plasticity of the Intracellular Plant Pathogen and Insect Symbiont "Candidatus Liberibacter asiaticus" as Revealed by Hypervariable Prophage Genes with Intragenic Tandem Repeats. Applied and Environmental Microbiology, p. 6663-6673, 2011) (Year: 2011).*
Cell death suppressor protein Lls1—*Cyanobium* sp _ UniProtKB _ UniProt_2024 (Year: 2024).*
Vasil, Vilma et al., "Increased Gene Expression by the First Intron of Maize Shrunken-1 Locus in Grass Species", Plant Physiol., 1989, vol. 91, pp. 1575-1579.
Vijaybhaskar, Virupapuram et al., "Identification of a root-specific glycosyltransferase from *Arabidopsis* and characterization of its promoter", J. Biosci., 2008, vol. 33, No. 2, pp. 185-193.
Wang, Z. et al., "Blackwell Publishing Ltd Development and application of molecular-based diagnosis for 'Candidatus Liberibacter asiaticus', the causal pathogen of citrus huanglongbing", Plant Pathology, 2006, vol. 55, pp. 630-638.
Wang, Hua et al., "From protein sequence to protein function via multi-label linear discriminant analysis", IEEE/ACM, May/Jun. 2017, vol. 14, No. 3, pp. 503-513.
Wang, Nian et al., "The Candidatus Liberibacter—Host Interface: Insights into Pathogenesis Mechanisms and Disease Control", ARI, Jun. 13, 2017, vol. 13, No. 36, pp. 20.1-20.32.
Wang, Nian et al., "SDE15 of Candidatus Liberibacter asiaticus suppresses host programmed cell death to facilitate chronical intracellular infection", Cell, Sep. 2, 2018, 77 pages.

(Continued)

*Primary Examiner* — Charles Logsdon
*Assistant Examiner* — Wayne Zhong
(74) *Attorney, Agent, or Firm* — Timothy H. Van Dyke; Wolter Van Dyke Davis, PLLC

(57) ABSTRACT

The disclosure relates to a plant that is tolerant or resistant to species of Ca. *Liberibacter*. Specifically exemplified are *Citrus* and solanaceous plants. Provided by the disclosure is a modified *Citrus* or solanaceous plant that is resistant or tolerant to Sec-dependent effectors secreted by bacteria. Also provided by the disclosure are methods of modifying a plant genome plant to provide tolerance or resistance to species of Ca. *Liberibacter*. Still further provided by the disclosure are methods conferring a population of plants with tolerance or resistance to species of Ca. *Liberibacter* and screening that population for the plants that are tolerant or resistant to species of Ca. *Liberibacter*.

15 Claims, 11 Drawing Sheets

Figures 3A, 3B:
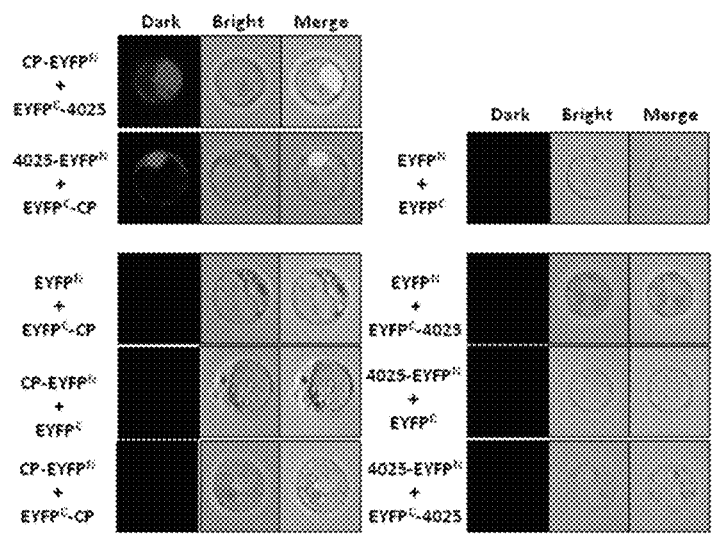

Specification includes a Sequence Listing.

(56) References Cited

OTHER PUBLICATIONS

Wuthrich, Karin L. et al., "Molecular cloning, functional expression and characterisation of RCC reductase involved in chlorophyll catabolism", The Plant Journal, 2000, vol. 21, No. 2, pp. 189-198.
Yao, Nan et al., "The mitochondrion—an organelle commonly involved in programmed cell death in *Arabidopsis thaliana*", The Plant Journal, 2004, vol. 40, pp. 596-610.
Zhang, Chao et al., "A sec-dependent secretory protein of the Huanglongbing-associated pathogen suppresses hypersensitive cell death in Nicotiana benthamiana", Front. Microbiol., 2020, vol. 11, No. 59, 11 pages.
Akpata, M.I. et al., "Chemical composition and selected functional properties of sweet orange (*Citrus sinensis*) seed flour", Plant Foods for Human Nutrition, 1999, vol. 54, pp. 353-362.
Albrecht, Ute et al., "Transcriptional response of susceptible and tolerant citrus to infection with Candidatus Liberibacter asiaticus", Plant Science 185-186, 2012, pp. 118-130.
Albrecht, Ute et al., "Gene expression in *Citrus sinensis* (L.) Osbeck following infection with the bacterial pathogen Candidatus Liberibacter asiaticus causing Huanglongbing in Florida", Plant Science, Sep. 2008, vol. 175, No. 3, pp. 291-306.
Bouchez, D. et al., "The ocs-element is a component of the promoters of several T-DNA and plant viral genes", The EMBO Journal, 1989, vol. 8, No. 13, pp. 4197-4204.
Bove' J.M., Huanglongbing: a Destructive, Newly-Emerging, Century•Old Disease of Citrus1 Journal of Plant Pathology, 2006, vol. 88, No. 1, pp. 7-37.
Callis, Judy et al., "Introns increase gene expression in cultured maize cells", Genes & Developments, 1987, vol. 1, pp. 1183-1200.
Cho, Hyung-Taeg et al., "Regulation of Root Hair Initiation and Expansin Gene Expression in *Arabidopsis*", The Plant Cell, Dec. 2002, vol. 14, pp. 3237-3253.
Citovsky, Vitaly et al., "Subcellular Localization of Interacting Proteins by Bimolecular Fluorescence Complementation in Planta", J. Mol. Biol., 2006, vol. 362, pp. 1120-1131.
Clark, Kelley et al., "An effector from the Huanglongbing-associated pathogen targets citrus proteases", Nature Communications, 2018, 11 pages.
Donmez, Dicle et al., "Genetic Transformation in Citrus", The Scientific World Journal, 2013, 8 pages.
Downward, Julian, "RNA interference", BMJ, 2004, vol. 328, pp. 1245-1248.
Edgar, Robert C., Muscle: multiple sequence alignment with high accuracy and high throughput, Nucleic Acids Research, 2004, vol. 32, No. 5, pp. 1792-1797.
Ellis, R.H. et al., "The Influence of Temperature on Seed Germination Rate in Grain Legumes", Oxford University Press, 1987, pp. 1033-1043.
Fraley, Robert T. et al., "The SEV System: A New Disarmed TI Plasmid Vector System for Plant Transformation", 1985, Bio/Technology, 1985, vol. 3, pp. 629-635.
Friedberg, Iddo, "Automated protein function prediction-the genomic challege", Briefing in Bionformatic,2006, vol. 7, No. 3, pp. 225-242.
Fu, Shimin et al., "Transcriptome analysis of sweet orange trees infected with 'Candidatus Liberibacter asiaticus' and two strains of Citrus Tristeza Virus", BMC Genomics, 2016, vol. 17, No. 349, 18 pages.
Gallie, Daniel R. et al., "Visualizing mRNA Expression in Plant Protoplasts: Factors Influencing Efficient mRNA Uptake and Translation", The Plant Cell, vol. 1, Mar. 1989, pp. 301-311.
Garrido, Jose L. et al., "Rapid separation of chlorophylls a and b and their demetallated and dephytylated derivatives using a monolithic silica C col. 18 and a pyridine-containing mobile phase", Journal of Chromatography A., vol. 994, 2003, pp. 85-92.
Hijaz, Faraj et al., "Collection and Chemical Composition of Phloem Sap from *Citrus sinensis* L. Osbeck (Sweet Orange)", Plos One, Jul. 2014, vol. 9, issue 7, 11 pages.

Hinchee, Maud A. et al., "Production of Transgenic Soybean Piants Using Agrobacterium-Mediated DNA Transfer", Bio/Technology, Aug. 1988, vol. 6, pp. 915-922.
Hortensteiner, Stefan et al., "Chlorophyll breakdown in senescent cotyledons of rape, *Brassica napus* L Enzymatic cleavage of phaeophorbide a in vitro", New Phytol., 1995, vol. 129, pp. 237-246.
Ikuta, Koichi et al., "A Developmental Switch in Thymic Lymphocyte Maturation Potential Occurs at the Level of Hematopoietic Stem Cells", Cell, Sep. 7, 1990, vol. 62, pp. 863-874.
Jagoueix, Sandrine et al., "The Phloem-Limited Bacterium of Greening Disease of Citrus Is a Member of the a Subdivision of the Proteobacteria", International Journal of Systematic Bacteriology, 1994, p. 379-386, vol. 44, No. 3.
Katz, Edward et al., "Cloning and Expression of the Tyrosinase Gene from Streptomyces antibioticus in Streptomyces lividans", Journal of General Microbiology, 1983, vol. 129, pp. 2703-2714.
Killiny, Nabil et al., "One Target, Two Mechanisms: The Impact of 'Candidatus Liberibacter asiaticus' and its Vector, Diaphorina citri, on Citrus Leaf Pigments", MPMI, 2017, vol. 30, No. 7, pp. 543-556.
Kim, Jeong-Soon et al., "Response of Sweet Orange (*Citrus sinensis*) to 'Candidatus Liberibacter asiaticus' Infection: Microscopy and Microarray Analyses", Phytopathology, 2009, pp. 50-57, vol. 99, No. 1.
Kurata, Tetsuya et al., "Cell-to-cell movement of the Caprice protein in *Arabidopsis* root epidermal cell differentiation", Development, 2005, vol. 132—No. 24, pp. 5388-5399.
Lee, Lan-Ying et al., "Vectors for multi-color bimolecular fluorescence complementation to investigate protein-protein interactions in living plant cells", 2008, Plant Methods, vol. 4, No. 24, 11 pages.
Lehner, A. et al., "Microbiological, Epidemiological, and Food Safety Aspects of Enterobacter sakazakii", Journal of Food Protection, vol. 67, No. 12, 2004, pp. 2850-2857.
Li, Jinyun et al., "Candidatus Libreribacter asiaticus' Encodes a Functional Salicylic Acid (SA) Hydroxylase That Degrades SA to Suppress Plant Defenses", MPMI, 2017, vol. 30, No. 8, pp. 620-630.
Ma, W. et al., "Effectoromics of the Huanglongbing (HLB)-Associated Pathogen", College of Nat & Agr Sciences, project 2016-2021, downloaded from Internet Mar. 21, 2019, 7 pages.
Mach, Jennifer M. et al., "The *Arabidopsis*-accelerated cell death gene ACD2 encodes red chlorophyll catabolite reductase and suppresses the spread of disease symptoms", PNAS, Jan. 16, 2021, vol. 98, No. 2, pp. 771-776.
Munyaneza, Joseph E., "Zebra Chip Disease of Potato: Biology, Epidemiology, and Management", Am. J. Pot Res, 2012, vol. 89, pp. 329-350.
Orbovic, Vladimir et al., "Citrus transformation using juvenile tissue explants", Agrobacterium Protocols, 2014, 3 pages, Abstract only.
Ow, Keith et al., "Transient and Stable Expression of the Firefly Luciferase Gene in Plant Cells and Transgenic Plants", Science, Nov. 14, 1986, vol. 234, No. 4778, pp. 856-859.
Pang, Zhiqian et al.,"Citrus CsACS2 is a target of Candidatus Liberibacter Asiaticus in Huanglongbing Disease", Plant Physiology, Oct. 2020, vol. 184, pp. 792-805.
Pelz-Stelinski, K.S. et al., Transmission Parameters for Candidatus Liberibacter asiaticus by Asian Citrus Psyllid (Hemiptera: Psyllidae), J. Econ. Entomol., 2010, vol. 103, No. 5, pp. 1531-1541.
Pitino, Marco et al., "Transient expression of Candidatus Liberibacter Asiaticus Effector induces cell death in Nicotiana benthamiana", Front. Plant Sci., 2016, vol. 9, No. 982, 13 pages.
Potrykus, Ingo et al., "Direct gene transfer to cells of a graminaceous monocot", Mol Gen Genet, 1985, vol. 199, pp. 183-188.
Prasher, Douglas et al., "Cloning and expression of the CDNA coding for Aequorin, A bioluminescent calcium-binding protein", Biochemical and Biophysical Research Communications, Feb. 15, 1985, vol. 126, No. 3, pp. 1259-1268.
Pruzinska, Adriana et al., "Chlorophyll Breakdown in Senescent *Arabidopsis* Leaves. Characterization of Chlorophyll Catabolites and of Chlorophyll Catabolic Enzymes Involved in the Degreening Reaction1", Plant Physiology, Sep. 2005, vol. 139, pp. 52-63.

(56) References Cited

OTHER PUBLICATIONS

Rawat, Nidhi et al., "Comprehensive meta-analysis, co-expression, and miRNA nested network analysis identifies gene candidates in citrus against Huanglongbing disease", BMC Plant Biology, 2015, vol. 15, No. 184, 21 pages.

Rodoni, Simona et al., "Partial Purification and Characterization of Red Chlorophyll Catabolite Reductase, a Stroma Protein Involved in Chlorophyll Breakdown", Plant Physiol, 1997, vol. 115, pp. 677-682.

Rogers, Scott O. et al., "Ribosomal RNA genes in plants: variability in copy number and in the intergenic spacer", Plant Molecular Biology, 1987, vol. 9, pp. 509-520.

Rondon, Silvia et al., "Potato Psyllid Vector of Zebra Chip Disease in the Pacific Northwest", PNW 633, May 2017, 8 pages.

Sheen, Jen et al., "Green-fluorescent protein as a new vital marker in plant cells", The Plant Journal, 1995, vol. 8, No. 5, pp. 777-784.

Stalker, David M. et al., "Herbicide Resistance in Transgenic Plants Expressing a Bacterial Detoxification Gene", Reports, Oct. 21, 1988, pp. 420-242.

Sutcliffe, J. Gregor, "Nucleotide sequence of the ampicillin resistance gene of *Escherichia coli* plasmid pBR322", Proc. Nati. Acad. Sci. USA, Aug. 1978, vol. 75, No. 8, pp. 3737-3741.

Thillet, Joelle et al., "Site-directed Mutagenesis of Mouse Dihydrofolate Reductase Mutants With Increased Resistance to Methotrexate and Trimethoprim", The Journal of Biological Chemistry, 1988, vol. 263, No. 25, pp. 12500-12508.

PCT Search Report & Written Opinion, PCT/US2018/059269, mailed Mar. 11, 2019, 17 pages.

\* cited by examiner

FIG. 1A
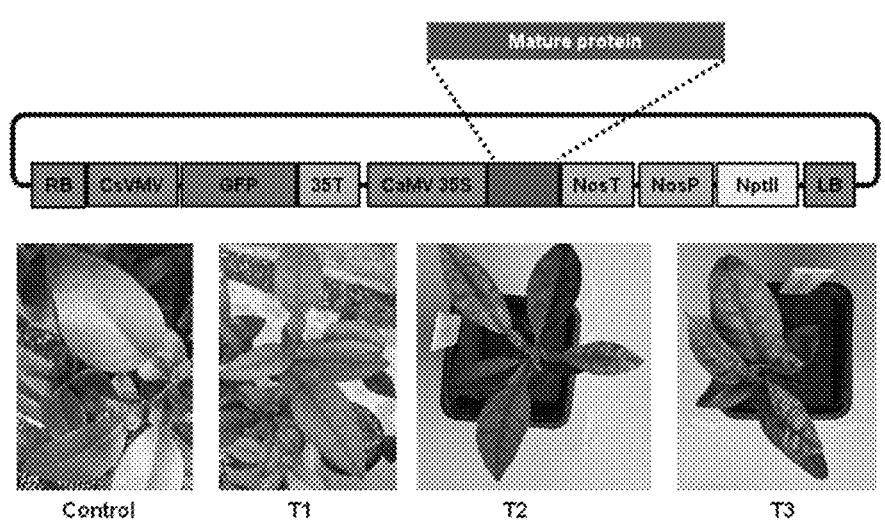
FIG. 1C
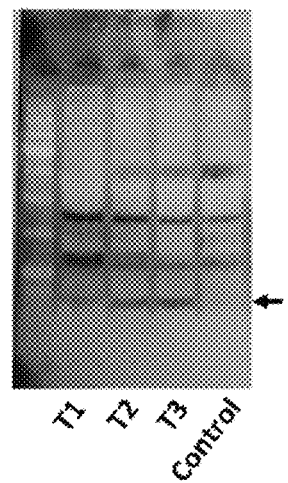
FIG. 1B

| BD | AD | Mating control (DDO) | Selection (DDO/X) | Selection (DDO/X/A) | Selection (QDO) | Selection (QDO/X) | Selection (QDO/X/A) |
|---|---|---|---|---|---|---|---|
| 4025 | RLK2 | | | | | | |
| EV | RLK2 | | | | | | |
| 4025 | PR10 | | | | | | |
| EV | PR10 | | | | | | |
| 4025 | PP2B2 | | | | | | |
| EV | PP2B2 | | | | | | |
| Positive | | | | | | | |
| Negative | | | | | | | |

FIGURE 2

FIG. 5A
FIG 5B
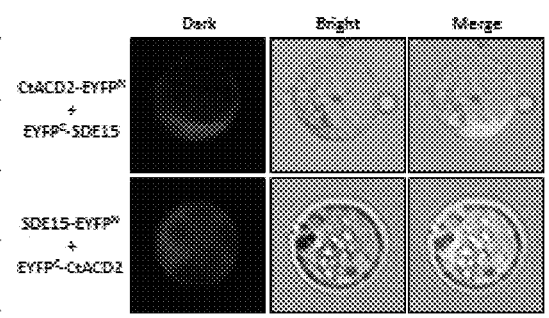
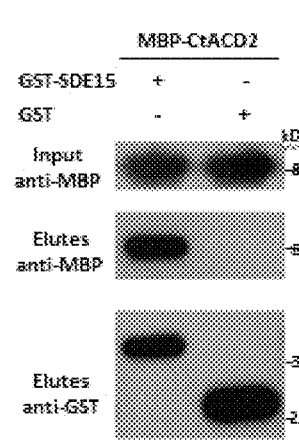
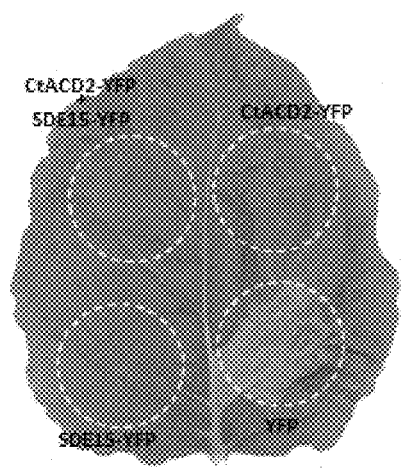
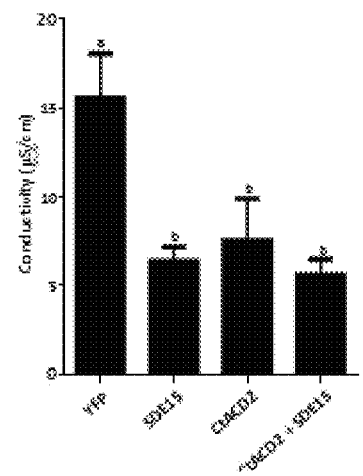
FIG. 5C          FIG. 5D          FIG. 5E Figure 6A
MTISKNQAILFFITGMILSSCGDTLSDSKQHNKINNTKNHLDLLFPIDDSHNQKPTEKKPN
TSSIKIKNNIIEPQPGPSRWEGGWNGERYVREWER
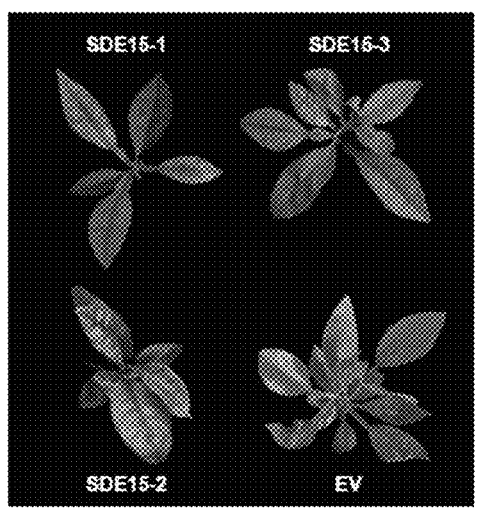
Figure 6B
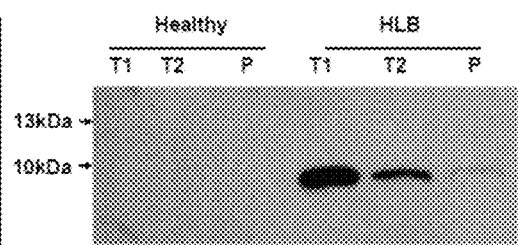
Figure 6C
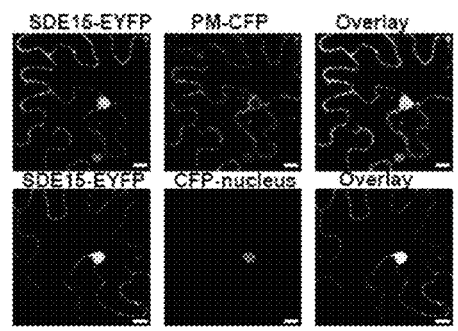
Figure 6D
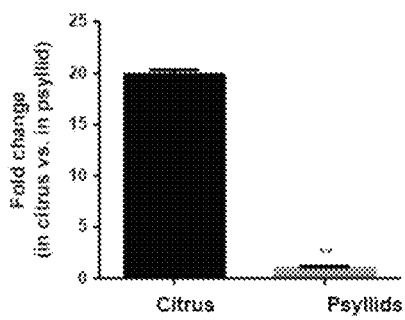
Figure 6E
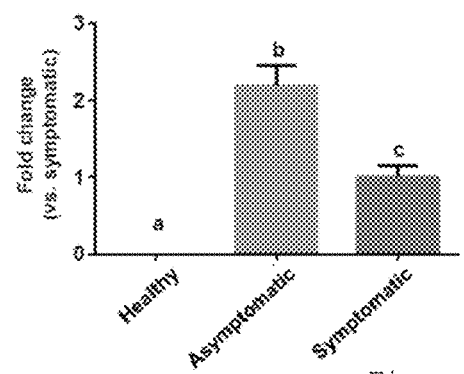
Figure 6F

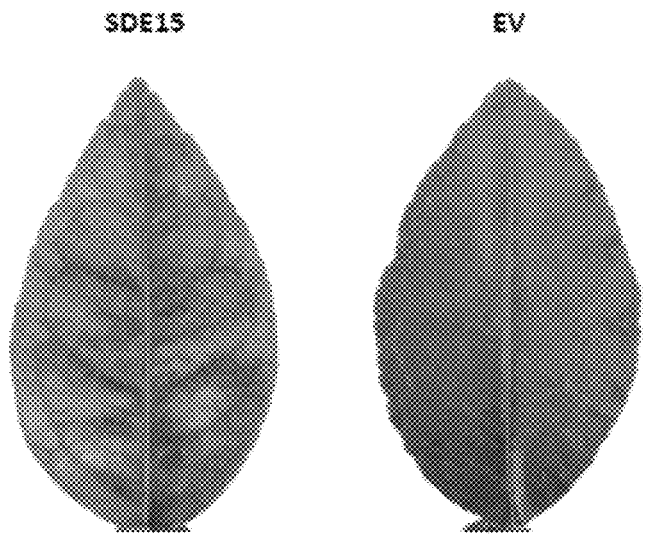
Figure 8
| Las Ct Value (per 100ng DNA) | | | | | |
|---|---|---|---|---|---|
| | 0 mpi | 1 mpi | 2 mpi | 3 mpi | 4 mpi |
| SDE15 | 37.17±0.46 | 37.43±0.53 | 35.38±2.09 | 32.54±1.38** | 32.11±0.68** |
| EV | 36.51±0.50 | 37.06±0.73 | 36.60±0.66 | 34.88±1.05 | 34.17±0.90 |
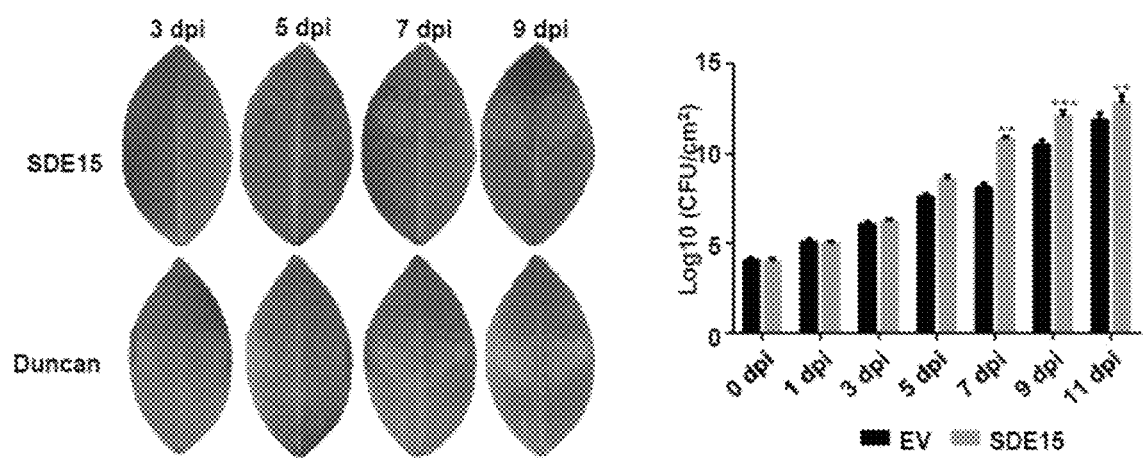
Figure 9A
Figure 9B

```
                              SEQUENCE LISTING

Sequence total quantity: 51
SEQ ID NO: 1            moltype = AA  length = 14
FEATURE                 Location/Qualifiers
source                  1..14
                        mol_type = protein
                        organism = Liberobacter asiaticum sp.
SEQUENCE: 1
DDSHNQKPTE KKPN                                                   14

SEQ ID NO: 2            moltype = DNA  length = 291
FEATURE                 Location/Qualifiers
source                  1..291
                        mol_type = genomic DNA
                        organism = Liberobacter asiaticum sp.
SEQUENCE: 2
atgacaatat caaaaaatca agccattctt ttctttatta caggcatgat actttcttct  60
tgtggtgata ctctctctga ctctaagcaa cataataaaa tcaacaatac aaaaaatcat  120
cttgatcttc ttttcccaat agacgactcc cataatcaaa agcctacgga aaaaaaacca  180
aatacatcat ccataaagat aaagaacaat ataatagaac cacaacccgg ccctagtcgc  240
tgggaaggag gatggaatgg tgaaagatac gttagagaat gggaaagata a          291

SEQ ID NO: 3            moltype = DNA  length = 156
FEATURE                 Location/Qualifiers
source                  1..156
                        mol_type = genomic DNA
                        organism = Liberobacter asiaticum sp.
SEQUENCE: 3
atgtatacca aaagtttgtt aatggtagct tatttgttat cttcggttgc aatatcgggt  60
gggctatgct ttaaccgccc aaaaggcccg tctaaagaag aacaagcacg aatagaacaa  120
atacgagcag aagcaagaga aaggcgctac caataa                           156

SEQ ID NO: 4            moltype = DNA  length = 1227
FEATURE                 Location/Qualifiers
source                  1..1227
                        mol_type = genomic DNA
                        organism = Liberobacter asiaticum sp.
SEQUENCE: 4
atgtttcaaa ataagaattt tttattaggc gttttgcgtc taaaaaagtg cacgcgtggt  60
gtttttttag ttattacagc tattttattg tcttcttttg tcgccatagt agatgttgtg  120
gtagatcagg tgacggtgat gcagaaaaca gcttggcttc aagaggtctt ggatcatgtt  180
atttatcgca cttctccaaa aaatttatat gatttaaggg aagcgggtag agataatttt  240
ataagacatc aaattgaaaa ggctttaaat acttataatt ccagagatct ttcaaatatt  300
gggagtatag aatcaatcgt taaagatgct gttattttaa cgaaaaatgt taattctttg  360
cctttacaat ttactgtcga catcgccctt tcgacaacgg ttcaattgcg aggatctctt  420
ttgcagatgt tttcgcaatc gaagggtaaa gttgatattt ctcgtcgaaa aaaagttatg  480
tataaacaaa atattggttt aatgattatg ccttttgcat gggatggcta ttggctagct  540
tcaagaggaa aggttgcaga ctcaaaagta catcctccaa agtatttgga gtattctcat  600
tattatcagc agtatcttaa tagaaatacg cttgtgaaaa attttctctc acaaattcct  660
tataaaaatt tctgtatggc tccttatcat tattcttcta ttctttattg ggcagtcgga  720
accttgacgt atagcgtgga taacaagacg actacgcgcg aatattataa ggatccttac  780
tatgctacat gggatcattt tccttattca tttatcaaga acgtatttga catgacttcc  840
aatcaatttg gagatgggca ggtattgact aataccaatc attgctttcc tcatggagca  900
agtcagaata aatatatgtt gatgcttgcg ataggaaatc agctatctcg aagttcagta  960
gagaaagaaa aaatagaaaa ggttctgcaa gactgccatt acatgcataa gcgtcataga  1020
actggaagag atgcaattac catattttct gtaggatttt ctccggatca agatacgcga  1080
tatactttaa gacaatgtgc aagtgatcca tctaaatatt atgaaattaa ttctgacgag  1140
aatgtcatgc ctatagccaa aagtcttgca cgtaatgtta taactaattg gtttagtcag  1200
tttacaatta ctgtggtcga tagctag                                     1227

SEQ ID NO: 5            moltype = DNA  length = 678
```

```
FEATURE              Location/Qualifiers
source               1..678
                     mol_type = genomic DNA
                     organism = Liberobacter asiaticum sp.
SEQUENCE: 5
atgagagata taagaaaaat tagaaattat tttaggaata ctgctaaaat tatattgagt    60
gggttatttc tagggttttt ttcttctgct gcaatggcag actatgggta ttctccccag   120
tttcagccga ctataatggt gtccaatttt gcaaaattta aagggttata tgttgctgct   180
gatttttcca aaatagatca tcagtcgcct gttcgtttgc aaaatctttc tttaaatggg   240
gtgtccattg gtcttgatgg tcaagatgga acccttgttt atggtgcttc tttgggtgtc   300
gagggatttc atcttgaacc acgaggggga attgatgggg ataaggtagc gggaacactc   360
ttgtttcgta ccggttttac gtttgataat aataattctt ctattctcca aaatactctt   420
atttatgggt ttggtggagc tcgtataaga aatattatgt ctgttgaatc tgctgacaca   480
gcaaaatcca caatacgaaa cattgtagca aacggttttc tagataaagt tattggtgtg   540
gggattgaaa agaaacttgc tagcatgctc tcgattcgtg gtgagtatcg ttatgtcgct   600
tgttatgacc agccttggga tgtcagcaag tggagagaaa aaggtgactt cacagctggt   660
gtggttttac gcttttaa                                                 678

SEQ ID NO: 6         moltype = DNA  length = 150
FEATURE              Location/Qualifiers
source               1..150
                     mol_type = genomic DNA
                     organism = Liberobacter asiaticum sp.
SEQUENCE: 6
atgaatacaa gaataatagg aaccgtatta atgcttgcta ttagtcctct tttatttagc    60
tgttcttcta aaaaggagg tgaaaaaaaa ggtgcggaga aaaaaacttc tgctccgttg   120
aaaaatggta aaaatcaatc cagaagatag                                    150

SEQ ID NO: 7         moltype = DNA  length = 1607
FEATURE              Location/Qualifiers
source               1..1607
                     mol_type = genomic DNA
                     organism = Citrus sinensis
SEQUENCE: 7
ataagcaagt ggccaagtag tgatttgacg gagtgattaa gaacgaatgg ctgtgaacca    60
cttatgccag tggcagtatt tacgcttcca gctctctcat ccatcggctc cggcttgcag   120
atatttatct ccttcgagac caaagtcctc aacgtcgtca accgccaaag tcaattgttc   180
tgccgcacca tcgtcgtctc cgatggactc gcacaacgaa ggccgtaaga agttcatgga   240
attccctac gcttcaggcc ctgttaggca gctgatggtt gatctcgtat caacggtaga   300
gaatacctc gattcgcagc tactcccttg cactctgcca ccagatgtac agtattcga   360
gaaccaaaat ggcactgctc aagcttctct tcaaatcaga tccgggctca agtcctcact   420
ggtagttctt tcttttacat aattggcgtt tgttaattg cgattgcaa cttgagtgaa   480
tttgtctcat aacttgattt aacctgaaac taggcgcctc tctaaacat tggaactgaa   540
cgcatttatg tctgaaatag atttttctttt cttagcctag gattgcacta ctctgcttag   600
ttgcctaagc ataagaaaca aatgattcaa aatttactag gctctagtgt gacattcaag   660
ttcgaggcgt acatggtctt caataatttg atgataatgg atgcgtgtca gattgatttc   720
atactgggaa gttggtaca cagtgagcta ccaacaggag cagcattgaa cataacaagc   780
cttttcagcat atctaaactc ttccactgat gcaccaaact tgctaattga gctcatccag   840
agtagccta cttctctagt cctcatcctt gacttgcctc tcgaaagga tcttgtcctc   900
catcccgact atcttcacac tttctatgaa agcacacggt tggatgaata taggcaaatg   960
cttgagaaag tacctgaagt tagaccctac ttctcttctt ccctttactt aagatgtgtc   1020
gtctctcctt cagcaattat ggtccgtgta gatactgaaa ctgaaactgg ggcaggtgaa   1080
tcaacacgtt tggactatat tataacaaat catgtgcatc ctgttgctaa gcaagttatt   1140
ggaatctggc taaatcagtg tgcttgtgga gggagacatg tagggagtc agacaaggct   1200
tatctggaaa agaggatgg gttgattaag aacaaaacta ttgagattga tctcggctct   1260
agctttccga gattgtttgg accgcaggta gcaagccggg tattaggcga gatacagaag   1320
gtttttactg cctgaggttg gtatttgaat ttgaggttgg gaatgtacaa agaattggag   1380
ttgattgacc ttaattttag tgtgtgtatg aacatcattg tcccccttt tatgcacaag   1440
ttctttgatt tcttcctgta attgatatgg cacttaaatt actgttgctt tctaatctta   1500
ttcgaattgg ttaaaatttc gtgcatgtat ggtgttttcta atcttgtaaa gcatgaagaa   1560
aggaacttac aacaatctca attaggaatg gaattgaatc ccttgaa                1607

SEQ ID NO: 8         moltype = DNA  length = 1434
FEATURE              Location/Qualifiers
source               1..1434
                     mol_type = genomic DNA
                     organism = Citrus sinensis
SEQUENCE: 8
atttgacgga gtgattaaga acgaatggct gtgaaccact tatgccagtg gcagtattta    60
cgcttccagc tctctcatcc atcggctccg gcttgcagat atttatctcc ttcgagacca   120
aagtcctcaa cgtcgtcaac cgccaaagtc aattgttctg ccgcaccatc gtcgtctccg   180
atggactcgc acaacgaagg ccgtaagaag ttcatggaat tccctacgc ttcaggccct   240
gttaggcagc tgatggttga tctcgtatca acggtgagga ataccctcga ttcgcagcta   300
ctcccttgca ctctgccacc agatgtacag tattacgaga accaaaatgg cactgctcaa   360
gcttctcttc aaatcagatc cgggctcaag tcctcactga ttgatttcat actgggaagt   420
tgggtacaca gtgagctacc aacaggagca gcattgaaca taacaagcct ttcagcatat   480
ctaaactctt ccactgatgc accaaacttg ctaattgagc tcatccagag tagccctact   540
tctctagtcc tcatccttga cttgcctcct cgaaaggatc ttgtcctcca tcccgactat   600
cttcacactt tctatgaaag cacacggttg gatgaatata ggcaaatgct tgagaaagta   660
```

```
cctgaagtta gaccctactt ctcttcttcc ctttacttaa gatgtgtcgt ctctccttca   720
gcaattatgg tccgtgtaga tactgaaact gaaactgggg caggtgaatc aaacacgtttg   780
gactatatta taacaaatca tgtgcatcct gttgctaagc aagttattgg aatctggcta   840
aatcagtgtg cttgtggagg gagacatgta ggggagtcag acaaggctta tctggaaaag   900
agggatgggt tgattaagaa caaaactatt gagattgatc tcggctctag ctttccgaga   960
ttgtttggac cgcaggtagc aagccgggta ttaggcgaga tacagaaggt ttttactgcc  1020
tgaggttggt atttgaattt gaggttggga atgtacaaag aattggagtt gattgacctt  1080
aatttagtg tgtgtatgaa catcattgtc cccttttta tgcacaagtt ctttgatttc  1140
ttcctgtaat tgatatggca cttaaattac tgttgctttc taatcttatt cgaattggtt  1200
aaaatttcgt gcatgtatgg tgtttctaat cttgtaaagc atgaagaaag gaacttacaa  1260
caatctcaat taggaatgga attgaatccc ttgaacatct tgttgaactg ttggtagatt  1320
aattaactcg ctagaatggg tgtgattgat gcactgaaga atatgaaatt tatttctgca  1380
tgattctact ctcatctcat cataatggtt tgatcactct gctgagcctt aaag         1434

SEQ ID NO: 9             moltype = DNA  length = 960
FEATURE                  Location/Qualifiers
source                   1..960
                         mol_type = genomic DNA
                         organism = Arabidopsis thaliana
SEQUENCE: 9
atggcgatga tattttgcaa cactctctac tcttcttctt ctccatcata tctctcgccg    60
ttaacttcaa aaccgtcgcg attctcaaag aatctcagct cattccagtc gattccagtc   120
atggaagacc acgacgatca cctccgccga aaatttatgg agttcccgta tgtgtcaccc   180
acgcggaagc agctcatggt tgatctcatg tcgacggtgg agaatcgcct ccaatcacaa   240
ctccttccct gtaacctccc tccagatgta cgaaacttca ataaccctaa cggttccgcc   300
gaagcatctc ttcatatcag atccggcgac aaatttcatt tgttataga                                     360
agttggatac attgcaagat cccaacagga gtatctttga atataacaag catctctgga   420
ttcttaaact catcaacaaa agctccaaac tttgtggtcg aactaataca gagcagttcc   480
aagtcgcttg tgctaatcct tgacctccca catcgtaaag atcttgttct taacccggat   540
tatctcaagg agtattacca agacactgct cttgattcct atcgacaatc tctccttaag   600
ctacctgaag ttaacccctta tgtgtctcct tctctctttg tccgttctgc tttctctcct   660
actgcttcga tgcttaagat tgatgcggag gaagaggata agttggagga gatattgaga   720
gatcatgtta gtccagctgc taaggaggtt ctcgaggttt ggttggagcg tgtgtgaag    780
gaagaagaag agaagattgt ggttgggaa aagagagaa tggagttgga gaagagagat    840
aaaagcttta gaaggaagag catatgaggac gatttggatt tgcagtttcc gagaatgttt   900
ggtgaagaag tttcctcccg tgttgtacac gctattaaag aagctttcgg tgttctctag   960

SEQ ID NO: 10            moltype = AA  length = 318
FEATURE                  Location/Qualifiers
source                   1..318
                         mol_type = protein
                         organism = Arabidopsis thaliana
SEQUENCE: 10
MAMIFCNTLY SSSSPSYLSP LTSKPSRFSK NLRPRAQFQS MEDHDDHLRR KFMEFPYVSP    60
TRKQLMVDLM STVENRLQSQ LLPCNLPPDV RNFNNPNGSA EASLHIRSGD KSSPIDFVIG   120
SWIHCKIPTG VSLNITSISG FLNSSTKAPN FVVELIQSSS KSLVLILDLP HRKDLVLNPD   180
YLKEYYQDTA LDSHRQSLLK LPEVNPYVSP SLFVRSAFSP TASMLKIDAE EEDKLEEILR   240
DHVSPAAKEV LEVWLERCVK EEEEKIVVGE EERMELERRD KSFRRKSIED DLDLQFPRMF   300
GEEVSSRVVH AIKEAFGV                                                 318

SEQ ID NO: 11            moltype = DNA  length = 3154
FEATURE                  Location/Qualifiers
source                   1..3154
                         mol_type = genomic DNA
                         organism = Citrus sinensis
SEQUENCE: 11
cagtgtgctc tctccaaaca aagcagacac aatcattagg catggctcgc cccgtacagt    60
tggtctcgtc cgtcatcttg ttgctttgct gcgctgccgc agcatcagca tcagcatcaa   120
gcttcgacga ctccaatccg atcagattgg tatcatcgga cggtctccgt gacttcgtga   180
cctccgtcct ccaggtgatc ggccaagccc gccatgtctc ctcctttgcc cgttttgctc   240
gcaggtatgg gaagatttac gagtccgttg aggagatgaa gctccggttc gcgactttct   300
ccaagaactt ggatttaatc agatctacca attgtaaagg cctatcttac aggctcgggt   360
tgaacagtaa gttttttcatt tgaatattg gtctgtagct caggaggcca gtcaagccat   420
ctgattgcct agattcctga ttggtctgta gttcacgtta ggcgtgct ttcctataac   480
aatctacgca ctagaatgaa ttttttacga ttttattatt attactgtta ttgttatgcc   540
catattttta ccaaaactca acttcgatga cataaaatga aagtgtgagg gcccaattta   600
attaggataa aacaatacaa actctaactc tcatcaaatt cagtattacg cgataagaga   660
taaaaattt ctaattaatt atactgttta ctttcaattat atatatttt tttttcatat   720
acgcgtgttc ttagttattc tatttgattt gtataggat tttgtacaaa tatattattt   780
ctcatcatag taactagtat tttgtgatct tcatttcttg ggaaccaatc atggattgat   840
gatgctttag cttatgtagt gattctgtag ttccctcagt agattaatca cggatggtta   900
taggttataa ttggataatc aagcttcaaa cttatatttt tgcattcatt tgtgtatctc   960
gtgcaatcta gtagtaaata tttatagtga aaatgaaaga ggtattaaaa ctgtcttatt  1020
tctactattg gattgtcaa ataacgaga atttgtataa aaaatttaag atcgtattta  1080
ctaaagttac actagtatta ttgattgcta attaactcta tacaattgtt gttgatggca  1140
tttaaatgta attaacataa cacgcagagt tgctgactg agctgggaa gagttccaaa  1200
ggcacaggtt gggagctgcg caaaactgct ctgccactac aaaaggaaat cacaagctta  1260
ctgctgatgt gcttccagaa acggtaattc tacgaaatac tattctcgat tgaacaacca  1320
agatgaccat cagtttctat aagcttgtat tttgtattac atagagagga aaagactgat  1380
```

```
ttttctgctg ctatatgtgt agaaagactg gagggaatct ggcatagtaa gcccagttaa  1440
agaccaaggt cactgtggat cttgctggac tttcaggtca gcttgatttg gaatgaaatc  1500
agaatttcta aactgagttt tcaattttag tgctaaataa ttacctttg cagcacgact   1560
ggatctcttg aggctgctta ccaccaggcc tttggaaagg gtatctcttt gtcagaacag  1620
cagcttgtag actgtgccca agctttcaac aaccaggat gcaatggtgg gttgccatcc   1680
caagcctttg aatacatcaa gtacaatggt ggccttgata ctgaggaagc atatccctac  1740
accggaaaag atggtgtctg caaattctca tctgaaaatg ttggcgtcca agtcctggac  1800
tcagtcaaca ttaccttggt gagttttatg ctgaattttc attttaaatg agagtagagt  1860
ctgcagtact ggactcacta catgccaaac aaatgaaaat caaccataaa taaatcaatc  1920
ataatctaga aactctggat atgtatatgt ttcaagtttc atgacttgta agacaatgca  1980
gggtgctgaa gatgaattac agcatgcagt tggtcttgtt cgacctgtga gtgtggcatt  2040
tgaagtagta gatggattcc gattttacaa gagtggagtt tacagcagca ctaaatgtgg  2100
aaatactccc atggtgagtc ttattgactt ggaaaacgat acattatttt gataggcatt  2160
gaatgcaaat ctgttaaaaa atgttttgat ttatgttcaa aatcaaaatt taacagggca  2220
ttcaagtttt gaagttttgc aaaacaaata aatgcctaac attatggtcc aaactctcca  2280
aacaacattt ctcattttct tttctgaact tctcagttgg tcaacatgtt actcacgcaa  2340
ggaatgctta atgtagacgt tgtgtaaatg atccttcact tggaattatc acccaagcat  2400
taaccactca tccgatgcat ttattgcatt tctaacttc tggattttat ggcaggatgt    2460
gaaccatgcc gtcgttgctg ttgggtacgg agttgaagat ggtgttccat attggctgat  2520
taagaactct tggggagaga actggggcga tcatggctac tttaagatgg agatggggaa  2580
gaacatgtgt ggtaagttac tgttacatct agattgtcag taccagatca ttgctcacaa  2640
cttaaattat cagtcatcgt caatttcgt catcatcaat tttcagtatg acctaagata   2700
tgatgtcaat aaaagaaaca gaataatgta gtatacatcc gataagtctt gataagttaa  2760
cagagtagta acagatctac gcatgaaatt tgaaacattt aaataggtga tatatatttg  2820
tgtttgctga ttttactgat ttgattgtag gtattgcaac ttgtgcatca tacccagttg  2880
tggcttagtc tgctcctgaa gaaatagttg gatctggtca tcagcaagtc atttgctcat  2940
aaaacttata ttatttcact caagaatgat agcagaatgg ttggctttat gtacgaaata  3000
aattcggaga ttaatgtcca tataatctac aatagcaatg catggctgct tgatgttcaa  3060
aataaattct gagatctatg tccatgtaaa cagtcattgt gactaggaca ccaacgatgt  3120
tatatatatt ttgtcaatgc aaggtagttg ttat                              3154

SEQ ID NO: 12          moltype = DNA   length = 2059
FEATURE                Location/Qualifiers
source                 1..2059
                       mol_type = genomic DNA
                       organism = Citrus sinensis
SEQUENCE: 12
cctctttgt gataaaaatg taagtaaaat attttgtacg attacaaatc attcctatat    60
taacagaaat gaacgctata acggcagaga aaaaaaccgt tacgacgacg tgaaggaatt   120
tcacgagaac gtcatcgcgc gcgtcagagt tagttcctat cgtctacgat acgacaaagc   180
cagcttagac gcccgttcta atctacaaat ttccaatcca tccctcagac tgaaaatgat   240
acggaatctt gagtcttgac ttatcttgca cccgacgagg catctcataa taataataat  300
aataataata ataataataa taataataca caactcattt caaccacata aattatgaat   360
ctcataattt tatataattg agatgaatta tgtaagttac attgaagata acttagcact  420
tgccgaataa taatagtgtt catagactgc attcatttaa tccgaagccc ttgagtgcag  480
tgtgctctct ccaaacaaag cagacacaat cattaggcat ggctcgcccc gtacagttgg  540
tctcgtccgt catcttgttg ctttgctgcg ctgccgcagc atcagcatca gcatcaagct  600
tcgacgactc caatccgatc agattggtat catcggacgg tctccgtgac ttcgagacct  660
ccgtcctcca ggtgatcggc caagcccgcc atgctctctc ctttgccgt tttgctcgca    720
ggtatgggaa gatttacgag tccgttgagg agatgaagct ccggttcgcg actttctcca  780
agaacttgga tttaatcaga tctaccaatt gtaaaggcct atcttacagg ctcgggttga  840
acaagtttgc tgactggagc tgggaagagt tccaaaggca caggttggga gctgcgcaaa  900
actgctctgc cactacaaaa ggaaatcaca agcttactgc tgatgtgctt ccagaaacga  960
aagactggag ggaatctggc atagtaagcc cagttaaaga ccaaggtcac tgtggatctt  1020
gctgacttt cagcacgact ggatctcttg aggctgctta ccaccaggcc tttggaaagg   1080
gtatctcttt gtcagaacag cagcttgtag actgtgccca agctttcaac aaccaggat   1140
gcaatggtgg gttgccatcc caagcctttg aatacatcaa gtacaatggt ggccttgata  1200
ctgaggaagc atatccctac accggaaaag atggtgtctg caaattctca tctgaaaatg  1260
ttggcgtcca agtcctggac tcagtcaaca ttaccttgca tgcagttggt cttgttcgac  1320
ctgtgagtgt ggcatttgaa gtagtagatg gattccgatt ttacaagagt ggagtttaca  1380
gcagcactaa atgtggaaat actcccatgg tgtgaacca tgccgtcgtt gctgttgggt   1440
acggagttga agatggtgtt ccatattggc tgattaagaa ctcttgggga gagaactggg  1500
gcgatcatgg ctactttaag atggagatgg ggaagaacat gtgtggtatt gcaacttgtg  1560
catcataccc agttgtggct tagtctgctc ctgaagaaat agttggatct ggctatcagc  1620
aagtcatttg ctcataaaac ttatattatt tcactcaaga atgatagcag aatggttggc  1680
tttatgtacg aaataaattc ggagattaat gtccatataa tctacaatag caatgcatgg  1740
ctgcttgatg ttcaaaataa attctgagat ctatgtccat gtaaacagtc attgtgacta  1800
ggacaccaac gatgttatat atattttgtc aatgcaaggt agttgttata tggaagcatt  1860
aggcaaatat caatgcattg cttaaaaaat tggttgtct tctgccctaa aaaggaactg    1920
agaacttgct gtgagaatga tcgtgtgttc attgtgacat ctgcctacta gatgccattc  1980
aattcatgct ctctacaggc cttttcatta tcataatttg ttgctgaaaa ataagggcac  2040
ttagcagctt aacctctta                                              2059

SEQ ID NO: 13          moltype = DNA   length = 2080
FEATURE                Location/Qualifiers
source                 1..2080
                       mol_type = genomic DNA
                       organism = Citrus sinensis
SEQUENCE: 13
```

```
cctcttttgt gataaaaatg taagtaaaat attttgtacg attacaaatc attcctatat    60
taacagaaat gaacgctata acggcagaga aaaaaaccgt tacgacgacg tgaaggaatt   120
tcacgagaac gtcatcgcgc gcgtcagagt tagttcctat cgtctacgat acgacaaagc   180
cagcttagac gcccgttcta atctacaaat ttccaatcca tccctcagac tgaaaatgat   240
acggaatctt gagtcttgac ttatcttgca cccgacgagg catctcataa taataataat   300
aataataata ataataataa taataataca caactcattt caaccacata aattatgaat   360
ctcataattt tatataattg agatgaatta tgtaagttac attgaagata acttagcact   420
tgccgaataa taatagtgtt catagactgc attcatttaa tccgaagccc ttgagtgcag   480
tgtgctctct ccaaacaaag cagacacaat cattaggcat ggctcgcccc gtacagttgg   540
tctcgtccgt catcttgttg ctttgctgcg ctgccgcagc atcagcatca gcatcaagct   600
tcgacgactc caatccgatc agattggtat catcggacgg tctccgtgac ttcgagacct   660
ccgtcctcca ggtgatcggc caagcccgcc atgctctctc ctttgcccgt tttgctcgca   720
ggtatgggaa gatttacgag tccgttgagg agatgaagct ccggttcgcg actttctcca   780
agaacttgga tttaatcaga tctaccaatt gtaaaggcct atcttacagg ctcgggttga   840
acaagtttgc tgactggagc tgggaagagt tccaaaggca caggttggga gctgcgcaaa   900
actgctctgc cactacaaaa ggaaatcaca agcttactgc tgatgtgctt ccagaaacga   960
aagactggag ggaatctggc atagtaagcc cagttaaaga ccaaggtcac tgtggatctt  1020
gctggacttt cagcacgact ggatctcttg aggctgctta ccaccaggcc tttggaaagg  1080
gtatctcttt gtcagaacag cagcttgtag actgtgccca agcttcaac aaccaggat   1140
gcaatggtgg gttgccatcc caagcctttg aatacatcaa gtacaatggt ggccttgata  1200
ctgaggaagc atatccctac accggaaaag atggtgtctg caaattctca tctgaaaatg  1260
ttggcgtcca agtcctggac tcagtcaaca ttaccttgga tgctgaagat gaattacgac  1320
atgcagttgg tcttgttcga cctgtgagtg tggcatttga agtagtagat ggattccgat  1380
tttacaagag tggagtttac agcagcacta atgtggaaa tactcccatg gatgtgaacc  1440
atgccgtcgt tgctgttggg tacggagttg aagatggtgt tccatattgg ctgattaaga  1500
actcttgggg agagaactgg ggcgatcatg gctactttaa gatggagatg gggaagaaca  1560
tgtgtgggtat tgcaacttgt gcatcatacc cagttgtggc ttagtctgct cctgaagaaa  1620
tagttggatc tggctatcag caagtcattt gctcataaaa cttatattat ttcactcaag  1680
aatgatagca aatggttggc ctttatgtac gaaataaatt cggagattaa tgtccatata  1740
atctacaata gcaatgcatg gctgcttgat gttcaaaata aattctgaga tctatgtcca  1800
tgtaaacagt cattgtgact aggacaccaa cgatgttata tatattttgt caatgcaagg  1860
tagttgttat atggaagctt taggcaaata tcaatgcatt gcttaaaaaa tttgttgtc   1920
ttctgcccta aaaaggaact gagaacttgc tgtgagaatg atcgtgtgtt cattgtgaca  1980
tctgcctact agatgccatt caattcatgc tctctacagg ccttttcatt atcataattt  2040
gttgctgaaa ataagggca cttagcagct taacctctta                          2080

SEQ ID NO: 14       moltype = DNA  length = 2243
FEATURE             Location/Qualifiers
source              1..2243
                    mol_type = genomic DNA
                    organism = Citrus sinensis
SEQUENCE: 14
caaactcacc gaaaattaat taaatctaat ctataataca aatacaaaaa cattaactac    60
cacgattgta taatgatatt tttgaatatt ccttcccact gaaagctctg tgcgaaaggg   120
ggaagtcaaa agtgttattc gttgttgtct atggctatga gttcgccact ttgggtagcc   180
ccaactttc tttctcgtcc atcgtcaaat atatcgagat caattactta caaacgttgc   240
aggtcttcgg caagtaactt tttctcacaa tcagacatgg agcagccgct gatgaagggg   300
cagaagctga tggaattccc tcacctgacg gcgcgcacaa aagatctgat ggttagctta   360
atctcagcct tggagactag gcttgactct catcttcttg cttcttcggt agtccctcct   420
gatgttgagt tttatcagaa tgaccaaggc acttctcagg gttctcttca tatcagacgt   480
ggccttcctt cctctcatgt actcgcttcc tctccctctc gtgtccagat tcaaattcac   540
tgttgcttat tcatatttat attattggtc attttaatct cgttaaatct ggatatatat   600
atatatatat atatatatat agggcactgt tccaatccgg attggaacag cctccgggaa   660
tggtttgggg atcattatat atatatatat atataattat ttttaagtgt ggacgctcgt   720
ttttttttgtt tttttataca gacactacgg tacagcagtt tttatacaga cactcttaaa   780
tcgtgtggtt taaaaaatta gttttttaaat aaactatata tatatatata tatattttat   840
tgcgaccgtc cttattttttt ttattcatgc tgatatactt taaaattaca gggtttaaga   900
gagttagttt ttaacacttt aaaactgcac ggttttataa ttcattcaat atatataaaa   960
ttattttttag gtgcggacat ccgcattttt ttaatcatga acacacttttt aaaccgaaaa  1020
gattagttat tgaatgaact ataaaatcat gtaattttta agagtgtccg cgtaaaaaaa  1080
aaaataaagg catcctctag agaatgacta tatatatata taatggtttt tggaatttga  1140
atgattaata accaccatgg agtcaattat caatcttaat gttaattggg atactgctga  1200
tcgcttttct cagcatgctt atagtagcta gctcatctt tccaaaactt atgtaaacat  1260
cctcctcttt tatgaacaat atactaggaa gtggtactag tgtactactc taaataattg  1320
actacctata tttttttcca aaaattctat caaaatcctc ctctttcatg aacaattaa   1380
atgggtaat attacgagag cccacttgtt ttcaagtgac gcttgctgga tattcacttt  1440
tgtataataa atgcttgtgg gaatgggaat cttttttctt ttttttttta acttttgctt  1500
ttggcatggt aacagattga tttcgtatta gcaagttggc ttcacttgga ggtaccaacg  1560
ggaagtgcca tgaacataac caatcttcaa gcttactaca aatcatcaac cgatgtacca  1620
cattttcaat tcgagcttgt ccaatgcagc cccacatatt tcattctctt cctagatata  1680
actcctagaa aagaccttgt tctataccca aattacctca aaacattta cgaagaagct  1740
cagcttgaaa cattgagaca gagacttgag caagtcccag aaaccaaacc ctacttgagt  1800
tcctctcttt actttcgtgg tgtggtctcc caactgggaa ttttggtcag cataaaaatgt  1860
gaggaagttg gtggaacgga tcgctgtgaa ggattatac gtgaacatgt gagccctata  1920
gctcatgatg tgatggtgat ttggttggag aagtattttt ctggagcaac tgttggggta  1980
actgagagag ctgaattgga gaagagagat ctttggttaa agactagagc catagagatg  2040
gacctgagtt ccagtctgcc cttgcagttt ggacaagaag tggcaaatcg agttttgagt  2100
gttattaaag gtgttttggg tgtgtagggt agaaagtgg ggagctccag attgcaagga  2160
attatagaat atattaaggt ggtgtttggt tgggaagaga gactagagga aatgaaagta  2220
```

```
atttaaattc tcgttttttt tta                                              2243

SEQ ID NO: 15           moltype = DNA  length = 1085
FEATURE                 Location/Qualifiers
source                  1..1085
                        mol_type = genomic DNA
                        organism = Citrus sinensis
SEQUENCE: 15
tgcgaaaggg ggaagtcaaa agtgttattc gttgttgtct atggctatga gttcgccact        60
ttgggtagcc ccaactttc ttctcgtcc atcgtcaaat atatcgagat caattactta         120
caaacgttgc aggtcttcgg caagtaactt tttctcacaa tcagacatgg agcagccgct       180
gatgaagggg cagaagctga tggaattccc tcacctgacg gcggcgcaca aagatctgat       240
ggttagctta atctcagcct tggagactag gcttgactct catcttcttg cttcttcggt      300
agtccctcct gatgttgagt tttatcagaa tgaccaaggc acttctcagg gttctcttca      360
tatcagacgt ggccttcctt cctctctat tgatttcgta ttagcaagtt ggcttcactt       420
gaaggtacca acgggaagtg ccatgaacat aaccaatctt caagcttacc taaaatcatc     480
aaccgatgta ccacattttc aattcgagct tgtccaatgc agcccacat atttcattct       540
cttcctagat ataactccta gaaaagacct tgttctatac ccaaattacc tcaaaacatt     600
ttacgaagaa gctcagcttg aaacattgag acagagactt gagcaagtcc cagaaaccaa     660
accctacttg agttcctctc tttactttcg tggtgtggtc tccccaactg ggattttggt      720
cagcataaaa tgtgaggaag ttggtggaac ggatcgctgt gaagagatta tacgtgaaca      780
tgtgagccct atagctcatg atgtgatggt gatttggttg gagaagtatt tttctggagc       840
aactgttggg gtaactgaga gagctgaatt ggagaagaga gatcttttgg ttaagactag       900
agccatagag atggacctga gttccagtct gcccttgcag tttggacaag aagtggcaaa       960
tcgagttttg agtgttatta aaggtgtttt gggtgtgtag ggtagaaaag tggggagctc      1020
cagattgcaa ggaattatag aatatattaa ggtggtgttt ggttgggaag agagactaga     1080
ggaaa                                                                  1085

SEQ ID NO: 16           moltype = DNA  length = 3474
FEATURE                 Location/Qualifiers
source                  1..3474
                        mol_type = genomic DNA
                        organism = Citrus sinensis
SEQUENCE: 16
agaaaacaac aaataaaaat tgcgtcattc cttcatgttg ggcaatttgc agcctcaagc        60
tcacggttcc ctgatcatga ctcatggcat gactcgtgtt cgtttcacaa ctatcaataa      120
ttgcctcaag ttttaatctt gcttgatctc tagtttgtgt tgagaacggt gctgcatgca      180
gccatggaag ctcttagact ctcctcggtt tcacttttt gtaacgctac attcaaactt      240
gagtacaata agacccactt cactaagccc aagttcttcagt t gcttt cagt cagttccctg 300
tccactttat catctttctc atcaaaacca tacaaaatct tcaccacctt atcaccatcg      360
tcacaagttt caactgaagc cacagaccca ccagaaagag agcttgaaac taactcacaa      420
gaggagaaat ttgattggtt ctcacagtgg tatccattga tgccggtgtg tgatttggac      480
aagagagtcc ctcatgcaaa gaaagtgttg gggcttgatg tcgtggtttg gtgggacagg      540
aatgagaatg aatggagagt ctttgctgat gcttgtcctc acagattggc tccttttgtca    600
gaaggaagaa ttgatcaatg gggaaggctt cagtgtgtgt atcatggctg gtgcttcagt     660
ggctcggggtg actgtaaatt tatccctcag gctcccccag acggccccc ggtaacatct      720
attgcttcac ttttgcatca cattcatatg ttttattatg ttttgtgttg ctatagatgc      780
ttttgcggtt gtctcgctta tgtgtagagt gagatgctat agttttgtcc aattagaatc      840
tcttctaggc atagagtttg tttgtttata attgttgcgc ttcagcgcgt tttttgcccg      900
aaagctatcc cggaaggact tacagactgg aagtaataaa ataggtcaag ggtctaattc      960
caagggggata cgtttaattc tgaaagagca gtagctaatt aaatgtttgg taaagccgtc     1020
acacctctca tcttcagttt aattgtgaag gaacaatgaa agataagggg aatacatgaa      1080
ttatgattcc attgcttgct tgataaaatt ttgttttgat ttttctgcaa tctagttttg       1140
attttttgtt cttgcatgca gttgttgtta agatttctac tttgctgggt ggctgattgc       1200
tttaattttt accaacttat ttgtcaaaat atgtaggtcc acacattcga gaaagcatgt        1260
gcagcagttt atccaagtac cgtccagcat gacatcgtat ggttttggcc aaatattgct        1320
cctcggtaca aggatattat caagactaag aaacctcctc acatcccgga actagatgac        1380
ccgtcattca caaaattgtt tgggaacaga gatataccct atgggtatgc aatgatccag       1440
tcttccattt taatttgagc gagttagcac acgaaattct agatttgaatt tgtactatac      1500
tgatatttgg caagagtcat taagaaaact agttgaactt aagtgtaatg acaacctggt      1560
caatgcaagt taacaacttt ttctaattgc aagtaagttg catttcagt tatgaggtct       1620
tattggaaaa tcttatggac cctgctcatg ttccatatgc acattacgga ttgatgcgta        1680
caaggaaacc caaggttga taaattccta gataaacctt gttctacgtt taagtcattt        1740
atattctctt cgtgaataaa acctattagt taatactaaa tttttctttac agtgaagctc      1800
gatagagaag ggggaagacc agttgaaatg agtgtcaata aaatagacat aaatggtttc       1860
attggaaagc aggagtgggg aagtagcaaa ttttggcac cttgtatctt ttttgcttat       1920
actgatctta tgaaggatca agaaaatgga tctgcatcat cagcaggagc cgaaaagta       1980
aaggtcaata tgtttgggct tgctcagctg acagtagaat tttgcactct tttcagttct      2040
tattctatgc tgtttgggct tcttttatc catatcatt tcggttggtg cagaagctgg      2100
agcaacaaag agcagctctg attttttatt gtgttccagt tagtcctggt cacagcagat      2160
taatatgggc gttcccaaga aacttttcaaa cttggataga caaagttgtt ccgcggtgga    2220
tatttcatat tggacagaat ctaattcttg attcagattt atacctgctt cacgttgagg       2280
tgattcctgt ctctgtatgc taaaataatt ttaacctaaa gttttttgaa aatgctgagt        2340
ggattccgt tcaagtctac tgctagtcta gccctcaaca tcagatttga gactcgtcga        2400
ccattcattt ttactagatt ggttgtgaca ccatcaaaa agcatatttt tgttttcctt         2460
ctcaatagaa ggtattcact taaatactac tctcctacaa tagaagaatt taatagattc        2520
tttcttgttt ctggctgtga attacctgac ttctgtttct ctctgcagga gcgaaagata       2580
atggatgttg gccctgctaa ttggcagaaa gcttgttttg tgccaacaaa agccgatgcc        2640
ctggtagttg gtttcaggag gtggttaaaa aaatatgccg gtggcaatt caattgggga        2700
```

```
gggaaattca atgcgactct tccaccaaca ccgcccaggg aacagctcat ggacaggtat  2760
ctgggcttca cttttataaa cttgaacccc ttaacaccat gtcatgggat tttacagtag  2820
ttcccagttt tgaaactcat ataaagagca gaggtttatg gatatttaaa agaagcatta  2880
tttgtttctt caagcttgag aaacatttt ctttgtgttt tgccaaattt cttatgcaat  2940
gccttgaaaa cgggaacact gtgaagtttg ttgtgacccc attaaaacat aagatttcgt  3000
acttaattaa aggaatttta ttcaaatttg caggtactgg tctcatgtgg tgaattgcaa  3060
aagttgcaat gcggcacaca agagtctcag cgcacttgag gtcacgctac aagtcgtctc  3120
cattgcttca attgggattg ttgctacaac caagcagaat gccatgtcaa tggctacaag  3180
aactacaatc atctcatttg cagtaatctg ctttgcggct tcaaaatgt tgtctcactt  3240
catctacaaa acctttcatt atcatgacta caatcgtgcc cttcgctgag cttagcattt  3300
aacgtcgaaa attagaatat gtaaatacaa cttatttttc tgtacgtaaa tactggaatg  3360
tagcttgtat gcaaacattt tgatcaagtg aaattagaaa gtgcagttgt aatagaaaac  3420
atataattat catcaccatt agcagttgta attgtaagta cattatcatc acca         3474

SEQ ID NO: 17          moltype = DNA   length = 2093
FEATURE                Location/Qualifiers
source                 1..2093
                       mol_type = genomic DNA
                       organism = Citrus sinensis
SEQUENCE: 17
atgcttcaga aaacaacaaa taaaaattgc gtcattcctt catgttgggc aatttgcagc  60
ctcaagctca cggttccctg atcatgactc atggcatgac tcgtgttcgt ttcacaaacta  120
tcaataattg cctcaagttt taatcttgct tgatctctag tttgtgttga aacggtgct  180
gcatgcagcc atgaagctc ttagactctc tcggtttca ccttttgta acgctacatt  240
caaacttgag tacaataaga cccacttcac taagcccaag ttcttaagct ttcagttcag  300
ttccctgtcc actttatcat cttctcatc aaaaccatc aaatcttca ccaccttatc  360
accatcgtca caagtttcaa ctgaagccac agacccacca gaaagagagc ttgaaactaa  420
ctcacaagag gagaaatttg attggttctc acagtggtat ccattgatgc cggtgtgtga  480
tttgacaag agagtccctc atgcaaagaa agtgttgggg cttgatgtcg tggtttggtg  540
ggacaggaat gagaatgaat ggagagtctt tgctgatgca tgtcctcaca gattggctcc  600
tttgtcagaa ggaagaattg atcaatgggg aaggcttcag tgtgtgtatc atggctggtg  660
cttcagtggc tcgggtgact gtaaatttat ccctcaggct cccccagacg gccccccggt  720
ccacacattc gagaaagcat gtgcagcagt ttatccaagt accgtccagc atgacatcgt  780
atggttttgg ccaaatattg ctcctcggta caaggatatt atcaagacta agaaacctcc  840
tcacatcccg gaactagatg acccgtcatt cacaaaattg tttgggaaca gagatatacc  900
ttatggttat gaggtcttat tggaaaatct tatggaccct gctcatgttc catatgcaca  960
ttacggattg atgcgtacaa ggaaacccaa agtgaagctc gatagagaag ggggaagacc  1020
agttgaaatg agtgtcaata aaatagacat aaatggtttc attggaaagc aggagtgggg  1080
aagtagcaaa ttttttggcac cttgtatctt tttttgcttat actgatctta tgaaggatca  1140
agaaaatgga tctgcatcat cagcaggagc cgaaaagaag ctggagcaac aaagagcagc  1200
tctgattttt atttgtgttc cagttagtcc tggtcacagc agattaatat gggcgttccc  1260
aagaaactc caaacttga tagacaaagt tgttccgcgg tggatatttc atattggaca  1320
gaatctaatt cttgattcag atttttaccct gcttcacgtt gaggagcgaa agataagga  1380
tgttggccct gctaattgcc agaaaagcttg ttttgtgcca acaaaagccg atgcctggt  1440
agttggtttc aggaggtggt taaaaaaata tgccggtggc caattcaatt gggggagggaa  1500
attcaatgcg actcttccac caacaccgcc cagggaacag ctcatggaca ggtactggtc  1560
tcatgtggtg aattgcaaaa gttgcaatgc ggcacacaag agtctcagcg cacttgaggt  1620
cacgctacaa gtcgtctcca ttgcttcaat tgggattgtt gctacaacca agcagaatgc  1680
catgtcaatg gctacaagaa ctacaatcat ctcatttgca gtaatctgct ttgcggcttc  1740
aaaatggttg tctcacttca tctacaaac cttcattat catgactaca atcatgcct  1800
tcgctgagct tagcattaa cgtcgaaaat tagaatatgt aaatacaact tatttttctg  1860
tacgtaaata ctggaatgta gcttgtatgc aaacatttg atcaagtgaa attagaaagt  1920
gcagttgtaa tagaaaacat ataattatca tcaccattag cagttgtaat tgtaagtaca  1980
ttatcatcac cattaacaat gcaagagaa acgtataca caactgaacc acggcttcag  2040
aatgaacaca agaagaacat ttttactagt tttcacaatg gtatctagtg atg         2093

SEQ ID NO: 18          moltype = DNA   length = 4930
FEATURE                Location/Qualifiers
source                 1..4930
                       mol_type = genomic DNA
                       organism = Citrus sinensis
SEQUENCE: 18
ccttgcttga tctcgatttt tgtgcagagt aaggtgttgc atgcagccat ggaagctctc  60
ttactctcct cagtttaccc atttttataac actccattaa aacttaagta caacagaacc  120
cacttcactg ctaagcccaa gctcttaagc ttccacttca gtccactatc cactttatca  180
tctttctcat caaaaccatc caaactcttc accaccttat caccatcatc tcaagtttca  240
actgaagcca cagaccccacc agagacagag cctgaaacta actcacaaga ggaaaaattt  300
gattggttct cacagtggta tccattgatg ccggtgtgtg atttggacaa gagagtcccc  360
catgcaaaga agtgttggg gcttgatgtc gtggtttggt gggacaggaa tgagaatgaa  420
tggagagtct tgccgatgc ttgtcctcac agattggctc ttttgtcaga aggaagaatt  480
gatcaatggg gacggcttca gtgtccgtat catggctggt gcttcagtgg ctcgggtgac  540
tgtaaatta tccctcaggc tcccccagac ggccccccgg taacatcgat tgcttcactt  600
ttgcatcaca ttcatatgtt ttattattt ttatgctgct atgtatgctt ttgcggtttt  660
cttgattacg tctagagtga gatgctactt ccttgctata ttttggtcta attagattcc  720
ctgaaggact aaaagactgg aagtaataaa ataggtcaag gcctaattc caatgggata  780
cgtttaattc tgaaagaact gtagctaatt taatgtttga taaagccacc acacctctcg  840
tcttcagttt gattgtgagg aaacaacgaa agataagcag aatacatgag ttatgattcc  900
atttcctgct tgataaaatt ttgtagtgat tttctgcaa tctagtattg attttcgttc  960
ttgcatgcag aagttgttaa gaattctact tgctgggtg gctgattgct ttaattttta  1020
```

```
ctgacttatt tatcaaaata cgcaggtcca cacatccaag aaagcatgtg cagctgttta   1080
tccaagtgcc gtacagaatg gcatcctatg gttttggcca gatattgctc ctcagtgcaa   1140
ggatatatc  aagactaaga aacctcctca catcccggaa ctcgatgacc cgtcatttac   1200
aaaaatgttt ggaagcaggg atgttcctta tgggtatgca gtgatccggt tttccatttt   1260
taatttgaaa ttccagtttg aatttgtacc atattgatat ttggcaacaa tcattaagaa   1320
aactagttga actcaagtgt aatgacagcc gggtaaatgc aagttaacag cttttttctaa  1380
gtgtaagtaa attgcatttt cagatatgag gtcctaatgg aaaatcttat ggatcctgct   1440
catcttacat atgcacatta cggaatgatg cgtacgagga aacccaaagg ttgataaatt   1500
cctggataaa ccttgtttta cgtttacgtc aactatatta ataaaaccca ttagctaatg   1560
ctaaattttc tttacagtga tgctcgatag agaaggggga agaccaatca aaataagttt   1620
cgagaaaata gacataaatg gtttcattgc aaagcaggat tcggaaagtg ccaaattttt   1680
ggcaccttgt gtctttgttg tttatttttga tcttctggag aatcaggaaa atggatctgc   1740
atcatcggga ggagccgaag aggtaagagt caatatgttt cgtaatgctc agctgacgga   1800
tagaattttg cactcttttc acccccctatt ctatgttgcc cccgcattgt ttgtccatat   1860
aaatttcgat cggtgcagaa gctgaagcaa cgaagagtag ctatgatttt tatttgtgct   1920
ccagtaagtc cgggtaacag cagagtaatc tgggccttcc caagaaactt ccagatttgg   1980
atagacaaag ttgttccgcg gtggatattt catattggac agaacctaat tctggattca   2040
gatttatgcc tgcttcacgt tgaggtgatt cctatctctg tatgctaaaa taattttaat   2100
ctaaagtttt tggaacatgc cgggtggatt ggcgttaaat tggagtgcta ggtagcatt    2160
atttatttg  tctgaaattt caatgagtga ataaatctct ctctctctct ctctctctct   2220
ctctctatat atatatatat atnnnnnnnnn nnnnnnnnnn nnnnnnnnnn nnnnnnncat   2280
atatatgaat aacatgttta tttttcttat tttgatatat gaataataagt gttattaaaa   2340
aaaaaaatga catcttctat atctatagag aagccaattt cgttgtagat tatatgcgca   2400
acctcacttt ttctcttcct tttggccttc ttgtgtacac tgccccacct ctaggtgtta   2460
ggtctctttt gcttcataac ttttacgggg tttctcaccc ccgttctgtt cttctttagc   2520
tcttttaga  gccccagttc aatiaataaa taaataaata aaatatgata ttttgaaata   2580
tataacatca taaatattaa caatacttat attttttttt attaaacaca tgacaagtta   2640
taaataaatt atttgattag taaaaaaaat ttaataatgt tttccttaac agagcacgaa   2700
aaataaaata tgtatctaac acacaatata tgatacttat gttgttatttt ttagtatatt   2760
atattgattt ttttaattac ttaatgtcaat taaagattgt ttaatcattt gaattaaatt   2820
taatgtatta aataaaattc aaaatctatt ataaaaatgg caaatataaa taccaagaga   2880
taggtccagt ggcggattta aaaaaataat ttaccggggg ctaaattaga taataataaa   2940
atatgaaaaa ttaaaatttt aaatatataaa aatatttgct agtacattta taattattct   3000
ctgcgcattt ttatatttta aaaatgttat acaattgact cattatcaat attattaaat   3060
ttattgtttc gtatataaac aatcaagttc aaatttaaat tttatggaga tttataattt   3120
atagtgatta ttttaataaa tttttttatgg gggttaatta aaaaactaaa atattttttct  3180
ttttaattt  taattttttta ttttgccagt gggggctcaa gccccacta gtcacatgct   3240
agatccgccc ctggataggt ctattataaa acacactcat ctaaagttcg attatgttca   3300
aaattctaat tcacaatata tatatatata tagttgaata catgtatata accaaaaaaa   3360
ggtaaataaa aaataataaa attatttata tgataggaa taaatttatt taatatgaat   3420
attaacgaga gagaatatta aaattacatt taaatatttt acaatttaga taaaagttgt   3480
agtatttaac ttttttgtatt tagatctaaa catcttataa ttagatataa gtaataaaaa   3540
aaagacagta aatatcataa aacaattaag attcaaactg agaaaaaaaa aatcaaacaa   3600
cccctgctcc tccagtctag gcctcaaact cagatattag actcgtcaac catttcattt   3660
tactagattg attgtgacac catccgaaaa gcatattttt gttttttcttc tcaatagaaa   3720
gtgttgatta aaataaacact ttgttgattt aaatactact ttcctacgat aaaagaaatg   3780
aatgcttct  ccgttgtttc tagccgcgaa taaaattctc tgcaacatat tgttacctga   3840
ctttggtttc tccctgcagg agcgaaagat aatggctgtt ggccctgcta attggcagaa   3900
agcttgtttt gtgccaacaa aatccgataa cctggtagtt ggtttcagga tgtggttaaa   3960
aaaatattcc ggtggccaat tcaattgggg aggaaaattc gatgcaactc ttccaccaac   4020
actgccaaga gaacagctca tggacaggta tttgggcttc acttcaataa acttgaatcc   4080
cttaacgccc tgtagttctt ggttttgaag aaagagcagg gatttatgga tttttaaaag   4140
aagcattatt tatttcttca ggcttgggaa acatttctc  ttgtgttttt gccaaaattc   4200
ttatgcaatg ccttgaaaac gggaacaata taagtttgc  tgtgaccca  ttaaaacgta   4260
agatcttgtg cttaattaaa ggaactttat tcaaattttc aggtactggt ctcatgtggt   4320
gaactgcaaa agttgcaatg ctgcacacaa gagtctcaat gcacttgagg tcatactgca   4380
agtcgtctct gttgtttcag ttgggattgt tgctgcaacc aagcagaacg ccatgtcaat   4440
ggctacaaga gctacgatcg tgtcatttgc agtaatctgc tttgcagctt caaaatggtt   4500
gtctcacttt gtctacaaaa cctttcatta tcatgactac aatcatgctc ttcgctaagt   4560
ttagcattgg taatactgta acttttaaaa taattgctat tacttatagc gttgaaataa   4620
tctgccgtga gcaaaatcaa tttaaaaact gataaatttt atttaaaaa atattgtgtc    4680
ttaaaaaata gtcgtatata agtttacatt ggtcataatg ttgaataaaa tttaggaaaa   4740
ttatcattcg tgtaccctaa agatgcactt ttatcaaaca tattcaaaca ctttcaaggt   4800
gtatcactca tccacccaaa aataccaaaa tatatctacc caccactatt ccgttagcca   4860
ccgtttgcaa actaacagaa ttgttgcgaa atgacaaata tgccctaaaa actaaaaaaa   4920
aacgcaaaaa                                                         4930

SEQ ID NO: 19          moltype = DNA   length = 2237
FEATURE                Location/Qualifiers
source                 1..2237
                       mol_type = genomic DNA
                       organism = Citrus sinensis
SEQUENCE: 19
cacaaacata agagacgcat taatttatgt tggactttc  agcgtcacgg tcagagtcca     60
ctgatcatga ctcatgtggc gcacgttcat tcgcaattag ctataattat ctcgagttct    120
aaccttgctt gatctcgatt tttgtgcaga gtaaggtgtt gcatgcagcc atggaagctc    180
tcttactctc ctcagtttca ccatttata  acactccatt aaaacttaag tacaacagaa    240
cccacttcac tgctaagccc aagctcttaa gcttccactt cagtccacta tccactttat    300
catctttctc atcaaaacca tccaaactct tcaccacctt atcaccatca tctcaagttt    360
```

-continued

```
caactgaagc cacagaccca ccagagacag agcctgaaac taactcacaa gaggaaaaat    420
ttgattggtt ctcacagtgg tatccattga tgccggtgtg tgatttggac aagagagtcc    480
cccatgcaaa gaaagtgttg gggcttgatg tcgtggtttg gtgggacagg aatgagaatg    540
aatggagagt ctttgccgat gcttgtcctc acagattggc tcctttgtca gaaggaagaa    600
ttgatcaatg gggacggctt cagtgtccgt atcatgcgtg gtgcttcagt ggctcgggtg    660
actgtaaatt tatccctcag gctccccag acgccccc ggtccacaca tccaagaaag      720
catgtgcagc tgtttatcca agtgccgtac agaatggcat cctatggttt tggccagata    780
ttgctcctca gtgcaaggat attatcaaga ctaagaaacc tcctcacatc ccggaactcg    840
atgaccegte atttacaaaa atgttggaa gcagggatgt tccttatgga tatgaggtcg    900
taatggaaaa tcttatggat cctgctcatc ttacatatgc acattacgga atgatgcgta    960
cgaggaaacc caaagtgatg ctcgatagag aaggggaag accaatcaaa ataagtttcg   1020
agaaaataga cataaatggt ttcattgcaa agcaggattc ggaaagtgcc aaattttgg   1080
caccttgtgt ctttgttgtt tattttgatc ttctggagaa tcaggaaaat ggatctgcat   1140
catcgggagg agccgaagag aagctgaagc aacgaagagt agctatgatt tttattgtg   1200
ctccagtaag tccgggtaac agcagagtaa tctgggcctt cccaagaaac ttccagatt   1260
ggatagacaa agttgttccg cggtggatat ttcatattgg acagaaccta attctggatt   1320
cagatttatg cctgcttcac gttgaggagc gaaagataat ggctgttggc cctgctaatt   1380
ggcagaaagc ttgttttgtg ccaacaaaat ccgataacct ggtagttgtt ttcaggatgt   1440
ggttaaaaaa atattccggt ggccaattca attggggagg aaaattcgat gcaactcttc   1500
caccaacact gccaagagaa cagctcatgg acaggtactg gtctcatgtg gtgaactgca   1560
aaagttgcaa tgctgcacac aagagtctca atgcacttga ggtcatactg caagtcgtct   1620
ctgttgtttc agttgggatt gttgctgcaa ccaagcagaa ccatgtcat atggctacaa    1680
gagctacgat cgtgtcattt gcagtaatct gctttgcagc ttcaaaatgg ttgtctcact   1740
ttgtctacaa aacctttcat tatcatgact acaatcatgc tcttcgctaa gtttagcatt   1800
ggtaatactg taacttttaa aataattgct attacttata gcgttgaaat aatctgccgt   1860
gagcaaaatc aatttaaaaa tcgataaatt ttattttaaa aaatattgty tcttaaaaaa   1920
tagtcgtata taagtttaca ttggtcataa tgttgaataa aatttaggaa aattatcatt   1980
cgtgtaccct aaagatgcac ttttatcaaa catattacaa cactttcaag gtgtatcact   2040
catccacca aaaataccaa aatatatcta cccaccacta ttccgttagc caccgtttgc    2100
aaactaacag aattgttgcg aaatgacaaa tatgcccta aaactaaaaa aaaacgcaaa     2160
aagacataaa taccccacaa accaagcaaa gaaaaataga tccgttagag acaataacag    2220
ttgtatttt tggctat                                                  2237

SEQ ID NO: 20         moltype = DNA  length = 4421
FEATURE               Location/Qualifiers
source                1..4421
                      mol_type = genomic DNA
                      organism = Citrus sinensis
SEQUENCE: 20
ccggttttc ttcttttc cgttttctga attctggaag cgtgaataca gacagacagc       60
tgggagaatt ggaggggcaa attgcaaact tgcacgcaaa gtcctcttct tttctgtct     120
ctctctcgaa agctcacttt attttcgctt cactagaatt ggaaaaatca tacaaaaatt    180
ttcattaaac tcaaagcaaa aggacatggc gctacttctt tctactactg ctaatatcac    240
cacatcacca agaaaaaccc ttccattttt ggccacagga accccgaagc gacaaatcac    300
ggtaaaaagc ttgcaaaaga gaagcaagaa tttgtctcca ctacgagtgg cagctcctcc    360
ttcagaccct gcagcatcag atgaagaaac gatgagaaaa gatgagaaag aagattatgg    420
atcattggtc gatgatgagt atggtaaaga gagttcggat tctaagtttt cttggaggga    480
tcattggtac ccagttctt tagttgaaga tttggacccg aacttgccta caccgtttca    540
gcttcttggg agagacttag ttctttggtt tgataacaat tctaataaat gggttgcatt    600
tgatgataaa tgccctcata gactcgcccc attatcggta atctattcta ttgttcctct    660
tgatctctgt aatttttgtga tcgaggtgaa acatagaaga taaaattgta atttgctcat    720
tttttattta atttttcgata ttatagtggt aatggaagaa gtaatatctg ttgttgtatc    780
ttattttctt tttaagaaat gaaatttgaa tggaggttt tctaggatct agagtgaagg    840
atatgaaatc taatttacaa attcatatct tgttctgttc ttgatcagtt tatccaagga   900
aagcctcaca tatagtcata tgaatgacca attttttgtc gttttcgata tagaatccga    960
aattcagaat tttgggagct gttgtttga ccattgatgt ttaatcttgg tagctaagtt   1020
gggaattatg tttcttagat catgtgattg atgggttcct taaaattta taggaagggc    1080
ggatcgatga aaatgggcat ttgcagtgtt cataccatgg atggtctttt gacgggtgtg   1140
gatcttgcac tcgcattccc caagcagcat ctgaagttcc tgaagctgt gcaattcagt    1200
ctcccagage gtgtgctacg aggtttccta caatggtgtc tcaaggtctg ctattcgttt   1260
ggccagatga gaatggtcag gaaagagcca atgccaccaa gccaccaatg taattgactc    1320
tattctctc ttctgttttt agattatgca ttgactgaat taccgactt gccgttcat     1380
taaacctgtg tggtaatgtt taggttgcct gatgactttg acaaacctga gttctcatcg   1440
gtcacaattc agcgggatct attttatggc tatgacatctc tcattgaaaa tgtctcagat   1500
ccttcccaca ttgattttgc acatcacaag gtacatactg aatttcaatg gtagtgtcgc    1560
tgggtgcaag atgaaatgt cattgaaca atagctggtt ggtttaagat aattttgata    1620
tgaattaaat atggtagtca gctcttggtc gatatgtctc attaactaaa ctagaaacac    1680
agttatcgtc tcttctgtcaag ttctttggtt ttcagtagtg tcaggaagtg cctgcaggta   1740
ttgttttctt agtggactga ttgaacacat agtggcgacg cttttgttt acttggccat    1800
gttgtgcttt ccttccagt cacttggaat ctcgtaacat cctagtactc atatacaggt    1860
catgttgttc tcattcatgg atatgtcctt gaacaaggag taaagtagtg aattctatac    1920
ccctatctcc tcattagatt gctataggaa tgtgacacta attgctctct ctgtggaaac   1980
aaatctccat gtaccttatt gagagacatc gttgcaggt taccggcaga agggacaggg   2040
ccaagcctta accgtttaag ttggagtcta gtggacattg gggatttgct ggagccaatg    2100
atggaaaccc aaggataagt gctaaatttg ttgctccttg ttattacatg aacaagtaag    2160
ttctccactg tctggaccag caaaattaat acgtctagat agactatctc ctttcctgct    2220
tatgctctct cagtgatact taaaattgtt gatttttca agaactggag atttgaataa    2280
tttcccaaac ttacttcaaa agcgtttagt attcctgatg aaaacattgt gtgataaagt    2340
gtgaacctta accatcaaat atttcctcct accaagactc aagttcattt tgttaagcca    2400
```

```
atcaatggag gcttgtattt caaagttaga ggttgacttt tggttaactg gaggatttat  2460
gcacaaacgt agaactgagt tgttttgaca tcagctgtag ttcaaggaag ccgatgaaac  2520
atcatttcat gtcttaattg tgtttaaaat tgaatacaac tgttgacgaa ctttctgctg  2580
agttaggtga tagttttagt tgattgagta ctatatttgt ttatcagttc attctgcttc  2640
cgaaacttaa ctatccgtgt attgcttttc ttccaggata gagatagata caaaacttcc  2700
tgtagttggt gataaaaaat ggataatatg gatttgttcc ttcaacgtac caatggcacc  2760
agggaaaacc cgctcaattg tttgtagtgc acgaaacttc ttccagttca ctatgccagg  2820
acctgcctga tggcaggtaa gaacatctca gttgtgtttc tgatgaaatt tgtataatgt  2880
gacacttgca tggaaacttt agtctaaaga gaacactcaa atgctgttga catgttcaag  2940
catacggaaa gtttatcttg ttaacacgct tgtgctagtg tgcacacaca tggttttagc  3000
ttccaattca ggtagttgat tgtcttatc ttggatacca tactgtccca tttgggaagg  3060
ggaagttttg gatgtctggc tgaaatgtgg agagaaaact ccttgatttg gagaagaaaa  3120
cttagttgag atgtatgctt aaaagttttc tccctgtttg agggccttt cttagatatt  3180
ggcatccgtg tcttgtaaac tttctaaata atattattca tattttcat gttgatgcca  3240
aagttccaat ctaaggggtt tgctgtcaga tttgataaga cttgttgag ctgtattgtt  3300
gatgattttc ctccacatga aattagttt ttaacggagt tatgtcctat ctccaccttta  3360
gaaaactaga aattttaatat ttttacttcg taaattggtg aattatctac aaaatggctt  3420
ccgattttac caggtggttc ctagatggca cgagcattgg acttcaaata aggtctatga  3480
tggagacatg attgtcctcc aaggtcaaga gaagatcttt cttcaaaat tgatggaagg  3540
ttctgaagat gttaacaagg agtacacaaa aattacgttt acacccacac aggcagatcg  3600
gcttgtgttg gcatttagaa attggctgag gcgacacggc aacagccaac ctgaatggtt  3660
cggcttcagc agccaacaac cttcccctt aacagtcttg tcgaaatgct aggtacgaaa  3720
cccttctcc attatttcaa gaaataaaaa atgaatattg ggattgaatt tagatttta  3780
aagtagatgg attcataatt tgtgttaagt gggacaatgt cacatttata ataagctcga  3840
ttaatatgtt attcacctt ctgggtttga tttcttcctt acgttttagt ttttctgttg  3900
ttgggtttg tttcagatgc tcgatagatt tgagcagcaa acctcaagt gttcatcatg  3960
tagagaagct tattcagcat tccgacgggg ccaaaagttt ctcattggcg cgaccgttgc  4020
attctgcgca acagctggga ttccttcaga tttgcaatca cggattgttt tggctgggct  4080
tgcactagtg agcgctgcct tggcttatgc tttgcatgaa ctacaaaaga attttgtgtt  4140
tgttgattat gtgcatgctg aaatcgatta gagagggagt agatatgct gctgaaagaa  4200
caatgtgtcc agaggtataa gaaagatatg gtgataaatc ttgtcaaaat ttgcgagttt  4260
gtatatatct attagataga aatcagtgtg atagctaagc ttagagttgtt tcctcagtat  4320
tccctttgtt tttgtgccaa atgaatgtca tcagataaat atgtgcagac atgcatccaa  4380
attcatgagt aaatggatta aacaatatac actttgtcaa a  4421

SEQ ID NO: 21            moltype = DNA   length = 2334
FEATURE                  Location/Qualifiers
source                   1..2334
                         mol_type = genomic DNA
                         organism = Citrus sinensis
SEQUENCE: 21
cacgaaaacac gccattgcca aagggcatta cgggaatttt gtgccagaaa atgtgacagt    60
aaatgaccag cagcccccttg acttttctatt ctgttagaac ctttaattgg tgagaccaat  120
catacaaact aaaccacaaa gtacttgatc gcaaatcgga caatcagaaa atcgagcta   180
accggttttt cttctttttt ccgttttctg aattctggaa gcgtgaatac agacagacag   240
ctgggagaat tggagggggca aattgcaaac ttgcacgcaa agtcctcttc ttttctgtc   300
tctctctcga aagctcactt tattttcgct tcactagaat tggaaaaatc atacaaaaat   360
tttcattaaa ctcaaagcaa aaggacatgg cgctacttct ttctactact gctaatatca   420
ccacatcacc aagaaaaacc cttccatttt tggccacagg aaccccgaag cgacaaatca   480
cggtaaaaag cttgcaaaag agaagcaaga attttgtctcc actacgagtg gcagctcctc   540
cttcagaccc tgcagcatca gatgaagaaa cgatgaaaga agatgagaaa gaagattatg   600
gatcattggt cgatgatgag tatggtaaag agagttcgga ttctaagttt tcttggaggg   660
atcattggta cccagtttct ttagttgaag atttggaccc gaacttgcct acaccgtttc   720
agcttcttgg gagagactta gttctttggt ttgataacaa ttctaataaa tgggttgcat   780
ttgatgataa atgccctcat agactcgccc cattatcgga agggcggatc gatgaaaatg   840
ggcatttgca gtgttcatac catggatggt cttttgacgg gtgtgggatct tgcactcgaa   900
ttccccaagc agcatctgaa ggtcctgaag ctcgtgcaat tcagtctccc agagcgtgtg   960
ctacgaggtt tcctacaatg gtgtctcaag gtctgctatt cgtttggcca gatgagaatg  1020
gtcaggaaag agccaatgcc accaagccac caatgttgcc tgatgacttt gacaaaccctg  1080
agttctcatc ggtcacaatt cagcgggatc tattttatgg ctatgacact ctcatgaaaa  1140
atgtctcaga tccttccac attgattttg cacatcacaa ggttaccggc agaagggaca  1200
gggccaagcc tttaccgttt aagttggagt ctagtggaca tggggatttt gctggagcca  1260
atgatggaaa cccaaggata agtgctaaat tgttgctcc ttgttattac atgaacaaga  1320
tagagataga tacaaaaactt cctgtagttg gtgataaaata tggatttgtn  1380
ccttcaacgt accaatggca ccagggaaaa cccgctcaat tgtttgtagt gcacgaaact  1440
tcttccagtt cactatgcca ggacctgcct ggtggcaggt ggttcctaga tggcacgagc  1500
attggacttc aaataaggtc tatgatggag acatgattgt cctccaaggt caagagaaga  1560
tcttttcttc aaaattgatg gaaggttctg aagatgttaa caaggagtac acaaaaatta  1620
cgtttacacc cacacaggca gatcggcttg ttggcatt tagaaattgg ctgaggcgac  1680
acggcaacag ccaacctgaa tggttcggct tcagcagcca acaacttcc ccttcaacag  1740
tcttgtcgaa atgtcagatg ctcgatagat ttgagcagca cacctcaag tgttcatcat  1800
gtagagaagc ttattcagca ttccagacgg gccaaaagtt tctcattggc gcgaccgttg  1860
cattctgcgc aacagctggg attccttcag atttgcaatc acggattgtt ttggctgggc  1920
ttgcactagt gagcgctgcc ttggcttatg ctacaaagaa aattttgtgt  1980
ttgttgatta tgtgcatgct gaaatcgatt agagagggag tagatatgct gctgaaagaa  2040
tcaatgtgtc cagaggtata agaaagatat ggtgataaat cttgtcaaaa tttgcgagtt  2100
tgtatatatc tattagatag aaatcagtgt gatagctaag cttagagtgt tcctcagta  2160
ttcccttttgt ttttgtgcca aatgaatgtc atcagataaa tatgtgcaga catgcatcca  2220
aattcatgag taaatggatt aaacaatata cactttgtca aatggaaagg agcgcatttc  2280
```

```
ctttaggaac aagcaaccac aaagtttagt catgaatcag tttgaaaaaa caat           2334

SEQ ID NO: 22          moltype = DNA   length = 2321
FEATURE                Location/Qualifiers
source                 1..2321
                       mol_type = genomic DNA
                       organism = Citrus sinensis
SEQUENCE: 22
cgtcatgcaa tgaggagaaa ttaggtgtcg aaatctcata cgcggaccca accacaagtt     60
tcttctgtct ttttggaaac atttattatc tgcttcatcc tgctttgcag tccactgaaa    120
caaatcgaaa atggagcgcc ttattctctc ctctctcctc ctcctcctcc tatcttctgt    180
gcttgcgtcc gctgtagctg tcaacgacga cgatgctatg atcagacagg tcgtgccgtc    240
agacggcgaa caatccgaag atcatctcct gaacgcggag caccacttct ccctcttcaa    300
gtccaaattc tccaagactt acgccaccca ggaggagcga gattaccgat tccgcgtgtt    360
caaggctaat ctgcgccgag caaagcgacg ccagctcctg gacccactg ctgtccacgg    420
tgtcaccaag ttctccgact taacgccgtc tgaattccgc cgtcagttcc ttggcttgaa    480
taggcggctt cggctgccag ctgacgctca aaaggctcct attctcccca ccaacgatcc    540
tcctactgac tttgactggc gtgatcacg cgccgttact ggcgtcaaag accaggtacg    600
ttagagaaag tgctttttt tttttcaaa aataaatttg aaaaaaataa ttgattttg       660
ttgatatttt tttattaatg tatgtagggc gcatgtggat cgtgctggtc gtttagtgca    720
accggcgctt tggagggagc gcacttctta tcgacgggcg agcttgtcag cctcagtgag    780
caacagcctg tggaactgtga tcacgaggtt tgttcaattg tttgttatat ttttaacgtt    840
agttaaatga tgaaaattac agattttgac tgattttgtt tgatagctag gatgagttgt    900
ataatttcta atcccaaaca gttagttatg acggtaaatc tcaaagttag attgggttct    960
cactctctga atttatgata aagaatttat atgtcagttt cctttttct tttaattct     1020
aatgttggtt cttcattatg ttaatctctt ttttttgtg gtttgatatt gttggatgcc   1080
ataatttgaa gttttgtggt gatatataat atcatataac tatccacaat atgttgggct  1140
tgtgctttt gtattctcaa tattgactgt ttgagttgtt tggacgtttc cctctcaagt   1200
ctgaactcac atctcacatg atcaaagtgt atgatttgac aaatataatt atgtttatta  1260
atgcaagttt tgtttcattt ttcagtgtga tccagagaa tctggttcat gtgactctgg   1320
gtgcaatggt gggctaatga actctgcctt tgagtacata ctcaaggctg gtggggttga  1380
gcgagagaag gactacctt acactgggac cgacggtggt tcctgcaaat ttgacaaaag   1440
caaaattgct gcagctgtat ctaatttcag tgttatttcc tctgatgaag atcaaatggc   1500
tgcaaatttg gtgaaacatg gccctctggc aggtaatgta gcttcgatac aattacctca   1560
tatttcgttt tccgtttctt ggcttttctc ttcactgtga gctctccaaa ataacatttg   1620
gaaaagttag ttaattaatt aatttctttt gagatgttgg taattttttt attaaacgga   1680
atggatagaa tgatgacaga atttgtgctg atcttgctgt ttgcttttgc agtgggtatc   1740
aatgccgttt ggatgcaaac atatattgga ggagtttcat gcccatatac ttgcgggaag   1800
tatttggatc atggagtgct tatcgtgggc tatggatctt caggtttcgc cccgatccgt   1860
ttcaaggaga agccttactg gatcataaag aactcctggg gagagaactg gggagagaat   1920
ggatattata agatctgcat gggtcgcaat gtctgtgggg tcgactccat ggtctcatct   1980
gtagctgctg tccatacaac ctcaagctag acattatgga ggttgtgcta ggcaagtgga   2040
gcttatatac gaagatatta taggatatcc ttttaaatag ccgtctgcaa ttataaggat   2100
gcctacatgc gtgggctgag gcatgaactt tatatgctct tgtaatattt aagcatatgt   2160
catgtcagaa tgtaatatttt atccatttta tagttaacca tgctacagaa ttgttattga   2220
agatggtatt aatatttct tttttatattg ggcaggcttg tagaaatatt ataatgttat   2280
attttctttt tatgtaactc aaaatagtag aacttcacgt a                       2321

SEQ ID NO: 23          moltype = DNA   length = 1890
FEATURE                Location/Qualifiers
source                 1..1890
                       mol_type = genomic DNA
                       organism = Citrus sinensis
SEQUENCE: 23
atttattata ataaaaaatt gttaccaata aattaataac ctaaaaaaaa aaattccaat     60
ggatgtatgg taaaggtgag tacgatcgat gcagtcatcc gtgacgccgg tttcttttgt   120
tttatagttc caatttgcag acttatatga ctaatcaaat ccgtcatgca atgaggagaa    180
attaggtgtc gaaatctcat acgcggaccc aaccacaagt ttcttctgtc ttttggaaa    240
catttattat ctgcttcatc ctgctttgca gtccactgaa acaaatcgaa aatggagcgc    300
cttattctct cctctctcct cctcctcctc ctatcttctg tgcttgcgtc cgctgtagct   360
gtcaacgacg acgatgctat gatcagacag gtcgtgccgt cagacggcga acaatccgaa    420
gatcatctcc tgaacgcgga gcaccacttc tccctcttca gtccaaatt ctccaagact   480
tacgccaccc aggaggagca cgattaccga ttccgcgtgt tcaaggctaa tctgcgccga    540
gcaaagcgac gccagctcct ggaccccact gctgtccacg gtgtcaccaa gttctccgac    600
ttaacgccgt ctgaattccg ccgtcagttc cttggcttga ataggcggct tcggctgcca    660
gctgacgctc aaaaggctcc tattctcccc accaacgatc ttcctactga ctttgactgg    720
cgtgatcacg cgccgttac tggcgtcaaa gaccagggcg catgtggatc gtgctggtcg    780
tttagtgcaa ccggcgcttt ggagggagcg cacttcttat cgacgggcga gcttgtcagc    840
ctcagtgagc aacagcttgt tggactgtga tcacgagtgt atccagaagg atctggttca    900
tgtgactctg ggtgcaatgg tgggctaatg aactctgcct ttgagtacat actcaaggct    960
ggtggggttg agcgagagaa ggactaccct tacactggga ccgacggtgg ttcctgcaaa   1020
tttgacaaaa gcaaaattgc tgcagctgta tctaatttca gtgttatttc ctctgatgaa   1080
gatcaaatgg ctgcaaattt ggtgaaacat ggccctctgg cagtgggtat caatgccgtt   1140
tggatgcaaa catatattgg aggagtttca tgcccataca ttgcgggaa gtatttggat   1200
catggagtgc ttatcgtggg ctatggatct tcaggtttcg cccgatccg tttcaaggag    1260
aagccttact ggatcataaa gaactcctgg ggagagaact ggggagagaa tggatattat   1320
aagatctgca tgggtcgcaa tgtctgtggg gtcgactcca tggtctcatc tgtagctgct   1380
gtccatacaa cctcaagcta gacattatgg aggttgtgct aggcaagtgg agcttatata   1440
cgaagatatt ataggatatc cttttaaata gccgtctgca attataagga tgcctacatg   1500
```

```
cgtgggctga ggcatgaact ttatatgctc ttgtaatatt taagcatatg tcatgtcaga    1560
atgtaatatt tatccatttt atagttaacc atgctacaga attgttattg aagatggtat    1620
taatatttc ttttatatt gggcaggctt gtagaaatat tataatgtta tatttcttt       1680
ttatgtaact caaaatagta gaacttcacg tatgcttaga cgcttgtatt ttcttattat    1740
atttgaagtt agctctattt agctctgttc atattaagaa atttcacaca actgccaagt    1800
ttgtgactgc ctgaccagtg tcactggttt aatagtctta tatgcttcta agtagcctaa    1860
gattacttag acttctcttt ataaactggt                                     1890

SEQ ID NO: 24              moltype = DNA   length = 1977
FEATURE                    Location/Qualifiers
source                     1..1977
                           mol_type = genomic DNA
                           organism = Citrus sinensis
SEQUENCE: 24
gaaattgatt tcagaaccag taaccaatat tcttcccaaa tatatcagtg ttaagttaca     60
aacacttctt gaaggatggg catttgcact ccgacaataa atactatcca tggaagcaca    120
atcacaagaa aagcaaaacc tggagcctgg taaaatgcca tcaagcatca tttctagtta    180
tcatttacaa gaactggctt ctgcttttta tctaacagat caatgtttc ttggatttca    240
tcaaaatcaa cacaaaaata atgaagttat agaagcttca ttaccaccat caaatcaatt    300
ttccggggat aatttttcca agaagttgtc tgagctagac actttggaat cattggtatt    360
atcgagcaac cgcaacagta aatttcccag aaaaaatagc agctttccca ctccttctga    420
gagcagccaa aatactaaag taagtttctt gtgttacctt acattatata atatatgtaa    480
ttattacatc aatcgattat tttctttct gaatttgac ctgtgtatat aacctttttt     540
tttttttgc atcactatag aatatgtctg aattttgacc tgtgtatata accttctttt    600
ctgaattttg acctgtgtat ataaccttt tttttttttt gcatcactat agaatatgag    660
catttttct tcagaagaaa agcattcttg tgggttgatt tctgattctt atcgacacat     720
tttgtcgaat aaaaaagaa ttacgtggac taaggatctg catgaacatt ttgtcgagtg    780
tgttaatcgc cttggaggtt ctgagagtga gtaaattgat atgatcaata atttatatag    840
gatctagcta atgattttat gtacttactt attttaattt ttgatgatca ttgtttgtga    900
attgattaat cctagaggca acaccaaagg cgatactgaa actgatgaaa tcgaaagaat    960
tgagtatcct acaagtaaaa agtcatttgc aggtttctat taattaatta aacaactgct   1020
attgctgtt ttttttttct tttacttca tgaaatttta attgtgattt atctcaacat    1080
gagatctgat atttcttgtt ttatttctct cttgctgctt gtcagaaata tcgatccgag   1140
aagctcatat cagaccagtc tttacaaggt aattaatcaa ttcttgttta aaaaatatat   1200
ttctatttaa tttgaatatc tgttaattaa aaaaaaaaaa ttgcaggatt tcccgagaaa   1260
acagtttgta tcaatgatat acctcagctt tacatgaaaa tgtacgcaaa ctcttcttga   1320
ttaatttcct tctacattct tgatattgtt cataacaatt ccagaaatta tgtgcttaaa   1380
ttaattttat gcaggggcat gcaaataaga gaggcacttc aattgcagct agaactcgag   1440
aagcattctc atgatcaatt agaggcatgt atttctatag aactttaatt tctattataa   1500
acttttaact ttttggtacg atatttttt tcaaaaaga aaaaagagtt aaaatcgtct    1560
tactacttta aaaattgtaa aataatagtg tccaatttat tattatattt tacaaaataa   1620
tttactactt ttctgttaat gccataaatt gacctgtaaa atactaatac taaaaaaaat   1680
tgggttattt tgtggaacaa ttaacaatga ttatcatctt catgaaaatg attaatttga   1740
ttcacctcac gtttaattta ttactttctt gctacagatg caaatgaatt tacaaaagct   1800
gattgaggat caagggaagc aggtgaagat gatgttagag aagcaattaa aatcaaacca   1860
gaaataattt gagcttacg attataatta tgtcgacaga gatcatgtta gaaaggatt     1920
aattgtagtt tattgacaac ataatcacaa gaaaacaaa aatgattgta gtaataa       1977

SEQ ID NO: 25              moltype = DNA   length = 693
FEATURE                    Location/Qualifiers
source                     1..693
                           mol_type = genomic DNA
                           organism = Citrus sinensis
SEQUENCE: 25
atggaagcac aatcacaaga aaagcaaaac ctggagcctg gtaaaatgcc atcaagcatc     60
atttctagtt atcatttaca agaactggct tctgctttt atctaacaga tcaatgtttc    120
tttggatttc atcaaaatca cacaaaaat aatgaagtta tagaagcttc attaccacca    180
tcaaatcaat tttccgggga taattttcc aagaagttgt ctgagctaga cactttggaa    240
tcattggtat tatcgagcaa ccgcaacagt aaatttccca gaaaaaatag cagctttccc    300
actccttctg agagcagcca aaatactaaa aaatatcgat ccgagaagca catatcgac    360
cagtctttac aaggatttcc cgagaaaaca gtttgtatca atgatatacc tcagctttac    420
atgaaaatgg gcatgcaaat aagagaggca cttcaattgc agctagaact cgagaagcat    480
cttcatgatc aattagagat gcaaatgaat ttacaaaagc tgattgagga tcaagggaag    540
caggtgaaga tgatgttaga gaagcaatta aatcaaacc agaaataatt tgagcttac    600
gattataatt atgtcgacag agatcatgtt agaaaaggat taattgtagt ttattgacaa    660
cataatcaca agaaaaacaa aaatgattgt agt                                 693

SEQ ID NO: 26              moltype = DNA   length = 1001
FEATURE                    Location/Qualifiers
source                     1..1001
                           mol_type = genomic DNA
                           organism = Citrus sinensis
SEQUENCE: 26
aacataaacg aatttactct ctgataacac ttttaatat atatttcac ttacctgcag      60
ttgtagcgct atctgctgac tgctgctgct gctgctactc aaaatggctg aaaggatcca    120
ccccgaaacg acaccgcgca acgaacaaga gccctctcat ccgccggcgc ccgcggccgc    180
aggaacctac gtcatccaaa tcccgaagga tcaaatctac cgagttccgc cccccgaaa    240
cgccgaccgc atcaagggcc tctcccgccg ccgcaagtcc cgcagcacta cctgctgctg    300
cttccgtttc tgctgctgct cgctgcttct cctcgtcctc ctcttggcca tcgccgcgg    360
```

|  |  |  |  |  |  |
|---|---|---|---|---|---|
| cgtcttctac | ctcgtcttcc | gtcccgaatc | ccccaactac | tccgtcgacg | gcgtctccat | 420 |
| cgccggcctc | aacctcacct | cgccgtcctc | cgtcgtctct | cccggttcg | acgtctccgt | 480 |
| caccgccgac | aatccgaacg | acaagatcgg | aatctactac | gagagaggca | gctcggtgga | 540 |
| ggtctcctac | aaggacgtcg | ccttatgcga | cggcgaatgg | cctcagtttt | accagccgag | 600 |
| caacaatgtc | acggttttca | agaccctcgct | gaaaggatcg | tccatcgagt | tgaccagcgc | 660 |
| tatgcgcaaa | gacctggttg | ctgctcagac | gagtggcaag | acggtgccgt | ttaaggtgaa | 720 |
| cttaagagtg | ccggttaaaa | taaaagtggg | gtcggttaag | acgtggacga | ttaaggtaaa | 780 |
| agtgagatgt | gatctgacgg | tggataagct | gacgtctcag | tcgaagatcg | tatctaagga | 840 |
| ctgtgattac | tctgtcaaac | tttggtaaaa | aaagttaaaa | aaatttcaaa | tcaaaaggat | 900 |
| tcattgtaat | tgtaggatta | gattatacaa | ttaattatta | taatttgtgg | tgtatttgtt | 960 |
| acaaatacac | acttattatt | atacttgtta | ttagtctgtt | t |  | 1001 |

SEQ ID NO: 27           moltype = DNA   length = 1141
FEATURE                 Location/Qualifiers
source                  1..1141
                        mol_type = genomic DNA
                        organism = Citrus sinensis
SEQUENCE: 27

|  |  |  |  |  |  |  |
|---|---|---|---|---|---|---|
| gtcagacaca | cacggccaaa | gtttaggcat | acgcgttagc | gcgtacgcgg | tttctttatc | 60 |
| aaaatatatg | ctatgctgca | tgcatatgat | ataataacat | aaacgaattt | actctctgat | 120 |
| aacacttttt | aatatatatt | ttcacttacc | tgcagttgta | gcgctatctg | ctgactgctg | 180 |
| ctgctgctgc | tactcaaaat | ggctgaaagg | atccaccccg | aaacgacacc | gcgcaacgaa | 240 |
| caagagccct | ctcatccgcc | ggcgccgcg | gccgcaggaa | cctacgtcat | ccaaatcccg | 300 |
| aaggatcaaa | tctaccgagt | tccgcccccc | gagaacgccg | accgcatcaa | gggcctctcc | 360 |
| cgccgccgca | agtcccgcag | cactacctgc | tgctgcttcc | gtttctgctg | ctgctcgctg | 420 |
| cttctcctcg | tcctcctctt | ggccatcgcc | gccggcgtct | tctacctcgt | cttccgtcg | 480 |
| gaatccccca | actactccgt | cgacggcgtc | tccatccgcg | gcctcaacct | cacctcgccg | 540 |
| tcctccgtcg | tctctccccg | gttcgacgtc | tccgtcaccg | ccgacaatcc | gaacgacaag | 600 |
| atcggaatct | actacgagag | aggcagctcg | gtggaggtct | cctacaagga | cgtcgcctta | 660 |
| tgcgacggcg | aatggcctca | gttttaccag | ccgagcaaca | atgtcacggt | tttcaagacc | 720 |
| tcgctgaaag | gatcgtccat | cgagttgacc | agcgctatgc | gcaaagacct | ggttgctgct | 780 |
| cagacgagtg | gcaagacggt | gccgtttaag | gtgaacttaa | gagtgccggt | taaaataaaa | 840 |
| gtggggtcgg | ttaagacgtg | gacgattaag | gtaaaagtga | gatgtgatct | gacggtggat | 900 |
| aagctgacgt | ctcagtcgaa | gatcgtatct | aaggactgtg | attactctgt | caaactttgg | 960 |
| taaaaaaagt | taaaaaaatt | tcaaatcaaa | aggattcatt | gtaattgtag | gattagatta | 1020 |
| tacaattaat | tattataatt | tgtggtgtat | ttgttacaaa | tacacactta | ttattatact | 1080 |
| tgttattagt | ctgttttgta | aaattcttgt | gtggaaacaa | gatatacaat | taattaatta | 1140 |
| a |  |  |  |  |  | 1141 |

SEQ ID NO: 28           moltype = DNA   length = 1380
FEATURE                 Location/Qualifiers
source                  1..1380
                        mol_type = genomic DNA
                        organism = Citrus sinensis
SEQUENCE: 28

|  |  |  |  |  |  |  |
|---|---|---|---|---|---|---|
| caaggttttc | aaaggagagt | gacctttaaa | aaaaaatgtc | accgcacac | aagaaaaaaa | 60 |
| taattaaaat | aaataaataa | aaaaatgtct | aagtccccta | tataataagt | gcatgtgaag | 120 |
| ctgagcgatg | ccattcaata | agtagccctc | gcagaacaaa | aaatgatttt | cctactactc | 180 |
| ctctcagtttt | tcttcgcgg | agcttcttca | tcaatccttt | ccgaagacac | acctattagc | 240 |
| ttctcatttc | cctcattcgc | caaagacagt | tgtgacaata | gaccctcat | ttgctacgga | 300 |
| gcgattgaaa | gttccggcgc | cttaagcatc | acaccaggtc | ctccaccaaa | cctgccgatc | 360 |
| agaaaggttg | gacgggtttt | atacggcaag | cctctgagtt | tacagcgatc | ttttattgat | 420 |
| accaccatca | ccattaagat | ctcacgccat | cagaattaca | ctgatcgtgc | cggagatggc | 480 |
| atgacgttca | tttttgcaag | cgataaaaac | ggtccatcag | caaagggcgt | cggcgaatat | 540 |
| cttggactgc | agtcttcacc | aggtatgatt | atcaatgtga | agaattaaga | atttatgcag | 600 |
| ataccattga | aagtactgac | aaatgcatgc | atgggcgcat | tttatttata | atggcagtca | 660 |
| aatgataaac | aatatgatga | tatatcatat | gttctatata | taacacttat | acatatatat | 720 |
| tcatgatcat | gcatgtaaat | tatgcaggcg | ataaatttcc | tccattagcc | gtggagctgg | 780 |
| acacatgcct | gaacaagaac | ctgaatgatc | cagatgataa | ccatattggc | atcgacataa | 840 |
| acggaatcga | atcaaatcca | gttaatagtc | tgcttgacgt | tgatctcaaa | agtggacgag | 900 |
| caatccaggt | tcgaatttat | tacaatccag | actttggaca | actctctatt | tatgcggcat | 960 |
| attcggggga | aacacttgtg | aaggtgattg | aaaaacccat | taacctgtca | gatataattc | 1020 |
| caacgcccgt | ctatgttgga | ttcacagcag | ctacggggga | ctttttagaa | agccatgagg | 1080 |
| ttataaattg | gaccttcaac | tcgttcccag | tgccgcctc | tctcaaggag | aaaaacgtgg | 1140 |
| tgatgccaat | ataattctaa | accgtccttg | aaaaaccatg | tcacataaat | tataatcaat | 1200 |
| aataattaat | atcaccaata | aagtgacatg | gctcttgcat | taaaatattg | aataaaatga | 1260 |
| tagcagcgac | taggattaat | actgtttgct | tgctgtctga | gatgtactgt | atgtgcttat | 1320 |
| gtagaaatgc | tcatattcag | cttctattga | ttacgttgca | gctttgagct | tctgatgttt | 1380 |

SEQ ID NO: 29           moltype = DNA   length = 1512
FEATURE                 Location/Qualifiers
source                  1..1512
                        mol_type = genomic DNA
                        organism = Citrus sinensis
SEQUENCE: 29

|  |  |  |  |  |  |  |
|---|---|---|---|---|---|---|
| acacaaggtt | tcaaaggag | agtgaccttt | aaaaaaaaat | gtcaccgaca | cacaagaaaa | 60 |
| aaataattaa | aataaataaa | taaaaaaatg | tctaagtccc | ctatataata | agtgcatgtg | 120 |
| aagctgagcg | atgccattca | ataagtagcc | ctcgcagaac | aaaaaatgat | tttcctacta | 180 |
| ctcctctcag | ttttttcttcg | cggagcttct | tcatcaatcc | tttccgaaga | cacacctatt | 240 |

```
agcttctcat ttccctcatt cgccaaagac agttgtgaca ataagaccct catttgctac   300
ggagcgattg aaagttccgg cgccttaagc atcacaccag gccctccacc aaacctgccg   360
atcagaaagg ttggacgggt tttatacggc aagcctctga gtttacagcg atcttttatt   420
gataccacca tcaccattaa gatctcacgc atcagaatt  acactgatcg tgccggagat   480
ggcatgacgt tcattttgc  aagcgataaa aacggtccat cagcaaaggg cgtcggcgaa   540
tatcttggac tgcagtcttc accaggcgat aaatttcctc cattagccgt ggagctggac   600
acatgcctga acaagaacct gaatgatcca gatgataacc atattggcat cgacataaac   660
ggaatcgaat caaatccagt taatagtctg cttgacgttg atctcaaaag tggacgagca   720
atccaggttc gaatttatta caatccagac tttggacaac tctctattta tgccggcatt   780
tcggggggaaa cacttgtgaa ggtgattgaa aaacccatta acctgtcaga tataattcca   840
acgcccgtct atgttggatt cacagcagct acggggact  ttttagaaag ccatgaggtt   900
ataaattgga ccttcaactc gttcccagtg ccgccttctc tcaaggagaa aaacctggtg   960
atgccaatat aattctaaac cgtccttgaa aaaccatgtc acataaatta taatcaataa  1020
taattaatat caccaataaa gtgacatggc tcttgcatta aaatattgaa taaaatgata  1080
gcagcgacta ggattaatac tgtttgcttg ctgtctgaga tgtactgtat gtgcttatgt  1140
agaaatgctc atattcagct tctattgatt acgttgcagc tttgagcttc tgatgttttc  1200
ttacccttt  cctcgttctc ttctttaagt ttatcggaac aaaattctct tctcacggtg  1260
gatatcatag cataaaattt aaccatagga aacaatgcat gcatcgctat agatattaat  1320
tacatgtgga gtccttttct cctgcgaacg tctgtacgta ttttgtgcg  atggaactca  1380
gatttttaga acgtcgtaca tttgcctcta gatgtatatg acaatataaa ctctattaga  1440
aatctgaatt catacatta  ttgcgtagtc catagttcta tcgataataa atatgaaata  1500
tgtgaaaaga at                                                      1512

SEQ ID NO: 30          moltype = DNA   length = 7810
FEATURE                Location/Qualifiers
source                 1..7810
                       mol_type = genomic DNA
                       organism = Citrus sinensis
SEQUENCE: 30
atggagaaat taattaagca aatcatgaat caaatacgag aagaatcgaa agaaattcaa    60
gaaccgttcc aacaatcacc tccactggta agtgattcta ttttttcact tttactccct   120
ccttcctttt acctcatata atttcaggta aacgctaatt tggtccatat aatttaagag   180
aattattccc tataaatttt gtcttattag ataaactctt acaatcagaa cactaggcca   240
agaagacaaa ggcttcagcg aaatggacaa atatggcgag gtcaattctt ttttgttttt   300
tttttggctt cttttttcac aattaatacg gtacagcagt cagagtcatg tgatgagatc   360
ttgcatttta catctttgc  tttaagcaca tggaatggaa ttgttggtat atgaatttta   420
gaattttctg ctgtaccgta catccgcctt ggccgtacag cagaaggtga gtacaaaatt   480
ccaatccatt gattatatat atactataat ttatggatgc catttaatta attcacgtag   540
gaaacagaag atttgaggct gaagattgat gaattggcag aggaagtaaa gaatggagaa   600
attaattaag caaatcatga atcaaatacg agaagaatcg aaagaaattc aagaaccgtt   660
ccaacaatca cctccactgg taagtgattc tattttttca cttttactcc ctccttcctt   720
ttacctcata aattcagg  taaacgctaa tttggtccat ataattaag  agaattattc   780
cctataaatt ttgtcttatt agataaactc ttacaatcag aacactaggc caagaagaca   840
aaggcttcag cgaaatggac aaatatggcg aggtcaattc tttttgtt   ttttttggc   900
ttctttttc  acaattaatg cttctttttt ctcgttgttt tagctgtttt agttgattaa   960
gttgtattca ttatttattt tatagttttt cttttccttt agtgagtcgg ccgacagctt  1020
atttactcgg ttgagcttt  aataaataaa tttatttct  ttttgttaaa aaaattgccc  1080
caaccccccca agggtttcac caagtagttt ttttaattga tcaccagaac ttaaatttg   1140
agcaggttgg agggctaaaa aaaaaaaatta atttaaactt ttaaaattaa tttatttgta  1200
aattaatttg tgaggtgtac tcagaaatca gggttttcag aaaattttta ggggtgccag  1260
tagcaccaat cttaattttt agagtttttc tctgacgaag atcgaaag attttataag    1320
cagactaaaa tatatacctg atttagcttg aaaactttga attaaactca ctagcgagaa  1380
aattctaaat taactattta agatccgata cttatgaaga cagtaattaa ccaaacatgt  1440
cttggccttt ctattttta  tatccttttt gtttaatcag ttttctcac  tctccttct   1500
ggtttatagg ttatgaggtg atcggtgagg taaggaacaa atgttgactg aaaagtctat  1560
caaattttg  tttctctctc tctctctctc tatttcttc  ttctaagaca ctgtcttata  1620
accagaaaac taatctagga cgacaaaggc ttcaacgaaa ggaaaaaatt tggccaggtc  1680
aagatacata ttttgtgttc tttgtttttcc cgttaatcac aatattttta ttctaaattc  1740
gaattttgta aaatttggat gttcaaacct gacaacaata tatatatata tattatttat  1800
ttcttttat  taaaataaaa atactcttat aaatagaaaa agaactccaa tgtattgaaa  1860
attttattt  tttatatttc agtacattgg agtttcgcat ttttttaaat tttcaaattg  1920
gagactaagg tggcgtttgt ttttaactt  aataacttaa agtgacttaa cttaattaat  1980
taagttaatt agaggtgttt gttttataa  cttaatgaga cttttagat  aactttgact  2040
taataaaata agtaattttt tttgactttt tacttaagtg agaatctgaa attaagtcaa  2100
ttacttgcta atgtcaaaaa tatccctatt ttataattta tttttcatgt atatcccaaa  2160
actcacccat agatatttac cccacataaa aatatccctg ttttttcttt cttatattat  2220
atacgataaa atttgaaatt tatggtattt tatatattaa attctaaaat aattatgtat  2280
tcacttgaat atagttttac ttataaatat taaaatattg tggtatttaa tatattattt  2340
atttgacatt caaatttaat aaggatataa atgtaaaagt acatattttc aacttttaa   2400
gttgaaaaaa ataaacaact taatacttat tttccgagat tcagacgaaa aaataaaat   2460
attatttaga ttcagacatt cagaccatt  cagaatttag acctattcag gtttattcag  2520
atttcagaca aaaaaacaaa cgtcacctaa gtctggagat agtcttttt  attttcgcat  2580
tttttttaaa aataaaaaaa ttttattttt tgttcatctt tttcacatt  ttttaattaa  2640
acaaatattt accctttttc attgtcctc  ctatattta  attctttat  gtttaattta  2700
tccttttttc tcctttttgg tttctaggat ctgaagaggt aattggtgac ggttgtcatg  2760
tttcgattcg tacggaaact aggaaaaaac ttaagatgt  agggatttgt gctcttcata  2820
attcaaaata taatttctcc taaaaaaaga aaaaattct  ctttataatt cataatataa  2880
atttatttt  tctaataata taccagattc gcggaaacaa tccatacccca ggatccatgg  2940
tcaaggataa agcaaaagaa attgttgatg acaataaggt cagtacaaaa ttatttgcaa  3000
```

```
acatcaatcc aaaacaaaat tcattactgt cttatatgtg ttattttatt attataggaa  3060
acagttgcta attcaattag tgaaggcttt gaagtgattg gcgacgaggt agatccagga  3120
ttaaatttat ttttatttta aattattagg taggaaaaag aacacttaca tccctaaggt  3180
cggagaaata attaaataga ccccaaattt tctaatccca agatatttt tttatatcat  3240
aatatctttt tattttttgtt aactcaaaaa atattgacaa aataaaaata taattttaaa  3300
ataaatgtaa taataaatac attttaaaat aactttaata ttaaaaaata ttttaatact  3360
taacaatcta ttagacattt tttattatat caaaataaaa ttttatacta aatagaaaca  3420
taatgtttaa acaaatatat taaaatctaa attattttaa atattatgta aaataataat  3480
tgggatattt taatttttcc actagaagtt ttttaatata tcacgttatt atcaagattt  3540
cttgaaagtt gcattttact acctaatgtt taggctatta tccttttaacc accaaaatgt  3600
taatatagtt aaaaatttac tgatgtcata agggctttaa agaaattttc attaaaacca  3660
atatgcatcg ttctcaatta tgaaataaac tgctaaataa taaaaaaatt aaaaaattcc  3720
taacccgaaa tgaaaattaa atggaaattt gaagaaattg agagtgaaga gaggaagaaa  3780
ggcaaatgct cttgagaatt tgaagaaggg agttcttagt tgagaatctg aagatgaagg  3840
agaaatggaa aagcagaaga aacgaagaag aagacaaaaa gggggaaaaa agttaaggaa  3900
aaaaaaaaga agaataaacg aagagggaaa gaaaagaaa aggaaaatg agagacattt  3960
gaagatgaag aagaaacaga gaagccggag aaatgaagaa gaagagaaaa aaggggggaaa  4020
aaaaaaatca gaaacacatt aaagccctac ccgcctcagc tgccgcaacc atccatcttc  4080
ttttcctcga tcatcaccac tagaaaacac tggccatcat aacccagcaa tcaacaccat  4140
gaaccgccgc cttaatgacc ataaaatacca tcaaacagct acgcagccaa acaacacaac  4200
tcgggtttgt tatttctttt tttttttcaaa ggacaagatt gtcttttgta ctctagggac  4260
aaaattgaat tttaacttat attctgttaa atatttactt atttttttaat ggaatagtgg  4320
tacagtaata accgcataaa tattaagtgg taaaatgcag ttttcacgaa tccttaatgt  4380
taactttttgg tagaaaaatg ataatgtccc taataaattta agcaccatta gtaagtaaga  4440
tattttacta attgtaaaat atatttaatc taaagattta tataaaatgt ctgtaataaa  4500
tacaaatata ttttttcaata tcaaaaatac ttttatatat tcaaaattat tttagatact  4560
acaaatattt taatattatt cgtcaactat attcaaagag tattatggta aaaaaatatc  4620
ttagtgttct tttctaaaaa cgtgagcatc tacatgtcta tttccaaaaa cttggatata  4680
actatccatt tctcctatta ggtcctaaaa aatataattt tgatagttaa atatgctagg  4740
ttacattgta atataccta catcaattgc aaaaggatc gattagctcc aagctcatgt  4800
catttttttt attcttttaa actcttttgt tcttagacaa gctctatcaa ccaagaaatt  4860
aggcacgac gacaaaggct tcagcgaaac ggaaacattt ggccaggtca attcgttttt  4920
tttccccttt attatttcct ttcttttttg ttttccttt tctaattaat catatctttt  4980
cccattctta gtttcatttt attacggtct aacatttgaa tttatttttt gtgtgtgtgt  5040
atgtatgtgt gtgtatatag agttctgcca tcattttact ttaatgcaga cttaattaag  5100
tagtaactaa gtgttttta atagtgataa aaaaatcaca aactctcatg tatatttatt  5160
taatggatta tgatgacaaa tgctactttg agtgaaaaaa agtgactgag aattttagtg  5220
agtttagaaa gagaccaaac tacctttact gattcttttg ttattattat tatttttaaa  5280
aggtaagggt ggataaagat aaaattatt tttaatctat acttcttta aaattttaaac  5340
tcatgtagtc agttaaagaa tattaattaa aaaccattta aaaaaaatacc attaatgatt  5400
tcaacttcta attaaagtaa ttaataatta aatttctgagt tagctgttta tgaatggaga  5460
cgtgcatgaa ggctgtaatc aaccaaaatt tgtcttggtc ctcctgtttt tactcatgca  5520
gtctcctttt cggtttctag gctctgaggt gattgttgac gatgttcaag attcggttcc  5580
tgtggattct gggaccaaca atgtagggac gtgacctctt ttccatacga cattatatgc  5640
atacgtgtca ttttttcactt tttcggcact gggattattt taattttttc gattattta  5700
tttctgatta gacaccgaaa aaaaaaaata caatcatttt gccagttaaaa taaaattgga  5760
aaagaaacaa atattaactc caaaatctgt cttttttttct ttcttttttg tcttttttgtt  5820
ttaatctttt tttttttttt tctattttct tcttcttaga tgagctctta cggccagaaa  5880
actaagccag gacggcaaag gcttaagcga aagaataca tttggccagg tcaatatata  5940
tattttttctt tcataactaa tctcatgttt tctcagtatg caggtttat ttttaattta  6000
ttttaatcct tagttaaaca taatgtcagc accttcacta gaaaatataa aaaaatatc  6060
catatatgta agaatgaaaa attaaatcac gaactaatat gtatgctgat ttaattcaga  6120
gtgatgctac ttgacggaac aaaaagtagg aaaaaaatct aacttcgatt ttgaaagagt  6180
ttgtataata ccgtgcttaa tttgggtaac tttttttttt tttttttggg tgaggatcac  6240
tgtatttcac ctcatttccc ccactaaggc tcgaacttag tacttggccc taagaagaca  6300
atgctcttac tatatgaact aagtcttcgc atccacttaa tttgggatact taggtaggat  6360
atctactgat gtgtcaccaa ttattaata ttatgtatat ggtattaatt aattttatta  6420
tcaattatta acctactact tttaaaattt ctcaataaat gatatataag atgctatatc  6480
agtaagtatc tcaattgagt atccaaagtg aataagcaca atattactgc tttaatttat  6540
atatcttgat cttttaatttt ttcttttcttt tctgttaaac ccattttct tattctcctt  6600
tttggtttct aggttctgag gtgattggtg agagtggttc gattcttact tatcaaaga  6660
aaaaactcga agatgtacga atttgagctc tttctattat tgatattaga tacatgtcat  6720
ttacaaattt ttaccactat gattaaatct attttttgatt ttcagattgg ttagtagtaa  6780
taaatatccc aaaattttat ccaaaaataa ttgggcatgt gatgtatgat tcatcaaaat  6840
agttgataaa tcttataggt cccaagtaaa ttagttataa tatttcacta tccaaacaaa  6900
tactacatca tttaggatca aagtttggga taggaaaaaa aaatattttg cttgaaaatt  6960
atttttgatt ttgtccagtc gggtataatt ttcggacact gttgtagtgc tctttgtgat  7020
gtattttgag ataaattcag tacattgtct tcactttgtg cagctacctg caaagtgcat  7080
ttcgcgcatc atttctctta cgacacctcg cgatgcaagt aggttggcac tggtatgtcc  7140
cgccttcaga tcggctgcgg attcagattc cgtatgggag aagtttttgc cgtccgatta  7200
cgaagggttc atttcgaact catctttgat cgacaggaag aagaaggatc tttattttca  7260
tctatgtcgc aaccccatcc tcttcgacaa taataccgcg agctttgggc tagagcaaga  7320
gagtggtaaa aaatgttaca tggctggtgc aaaatggatt tatgaaaatt cgggaatttc  7380
acaccgagat tgcgaaatga ttccttcatc agctgatct aggtttcctg aagtgattga  7440
acttaagctt atgtcgagtt tagaaatcga agcaagattt ggtacaacaa ttttttcacc  7500
caaaccaat tatgcagctt actttgtgtt caagtttgcg gaattcagag aagggcctga  7560
aactagtcct atagatttgg aagtctattt tgagggaagc cataatggca aaaagctag  7620
agagtttctt gatcctcaac tatctcaaga ccgaggaaat aggtggatag agattaagat  7680
gggtgagttc tctattgaaa atggagatga aggaacagta gtttgtaggc tgtccgaacc  7740
```

```
agaacccttaa tctaagcgtg gcactattat tttccaaggt attgaggtta ggcctgaata    7800
tggcaggtaa                                                            7810
```

| SEQ ID NO: 31 | moltype = DNA  length = 1434 |
|---|---|
| FEATURE | Location/Qualifiers |
| source | 1..1434 |
| | mol_type = genomic DNA |
| | organism = Citrus sinensis |

SEQUENCE: 31
```
atggagaaat taattaagca aatcatgaat caaatacgag aagaatcgaa agaaattcaa      60
gaaccgttcc aacaatcacc tccactgaac actaggccaa gaagacaaag gcttcagcga     120
aatggacaaa tatggccagg ttatgaggtg atcggtgaga cactgtctta taaccagaaa     180
actaatctag gacgacaaag gcttcaacga aggaaaaaa tttggccagg atctgaagag      240
gtaattggtg acggttgtca tgtttcgatt cgtacggaaa ctaggaaaaa acttaaagat     300
attcgcggaa acaatccata cccaggatcc atggtcaagg ataaagcaaa agaaattgtt     360
gatgacaata aggaaacagt tgctaattca attagtgaag gctttgaagt gattggcgac     420
gagacaagct ctatcaacca agaaattagg ccacgacgaa aaggcttca gcgaaacgga     480
aacatttggc caggctctga ggtgattgtt gacgatgttc aagattcggt tcctgtggat     540
tctgggacca acaatatgag ctcttacggc cagaaaacta agccaggacg gcaaaggctt     600
aagcgaaaag aatacatttg gccaggttct gaggtgattg tgagagtgg ttcgattctt     660
acttatcaaa agaaaaaact cgaagatcta cctgcaaagt gcatttcgcg catcatttct     720
cttacgacac ctcgcgatgc aagtacggtt gcactggtat gtcccgcctt cagatccggt     780
gcggattcag attccgtatg ggagaagttt ttgccgtccg attacgaagg gttcatttcg     840
aactcatctt tgatcgacag gaagaagaag gatctttatt ttcatctatg tcgcaacccc     900
atcctcttcg acaataatac cgcgagcttt gggctagagc aagagagtgg taaaaaatgt     960
tacatggctg gtgcaaaatg gatttatgaa aattcgggaa tttcacaccg agattgcgaa    1020
atgattcctt catcagctgg atctaggttt cctgaagtga ttgaacttaa gcttatgtcg    1080
agtttagaaa tcgaagcaag atttggtaca acaatttttt cacccaaaac caattatgca    1140
gcttactttg tgttcaagtt tgcggaattc agagaagggc ctgaaactag tcctatagat    1200
tttgaagtct attttgaggg aagccataat ggcaaaaagc gtagagagtt tcttgatcct    1260
caactatctc aagaccgagg aaataggtgg atagagatta agatgggtga gttctctatt    1320
gaaaatggag atgaaggaac agtagtttgt aggctgtccg aaccagaacc cttatctaag    1380
cgtggcacta tttttcca aggtattgag gttaggcctg aatatggcag gtaa           1434
```

| SEQ ID NO: 32 | moltype = DNA  length = 393 |
|---|---|
| FEATURE | Location/Qualifiers |
| source | 1..393 |
| | mol_type = genomic DNA |
| | organism = Citrus sinensis |

SEQUENCE: 32
```
atggctgaaa ggatccaccc cgaaacgaca cagcgcaacg aacaagagcc ctcacatccg      60
ccggcgcccg cggccgcaag aacctacgtc atccaaatcc cgaaggatca aatctaccga    120
gttatgcccc cgatgaacgc cgaccgcatc aagggcctct cccgccgccg caaatcccgt    180
agcactacct gctgctgctt ctgtttctgc tgctgctcgc tgcttctcct cgtcctcctc    240
ttggccatcg ccgccgacgt cttctacctc gtcttccgtc ccgaagcccc caactactcc    300
gtcgacgaca agatcggcat ctactacgag agaggcagct cgatggaggt ctactacaag    360
gacgtcggct tatgcgacgg cgtctggcct tag                                 393
```

| SEQ ID NO: 33 | moltype = DNA  length = 393 |
|---|---|
| FEATURE | Location/Qualifiers |
| source | 1..393 |
| | mol_type = genomic DNA |
| | organism = Citrus sinensis |

SEQUENCE: 33
```
atggctgaaa ggatccaccc cgaaacgaca cagcgcaacg aacaagagcc ctcacatccg      60
ccggcgcccg cggccgcaag aacctacgtc atccaaatcc cgaaggatca aatctaccga    120
gttatgcccc cgatgaacgc cgaccgcatc aagggcctct cccgccgccg caaatcccgt    180
agcactacct gctgctgctt ctgtttctgc tgctgctcgc tgcttctcct cgtcctcctc    240
ttggccatcg ccgccgacgt cttctacctc gtcttccgtc ccgaagcccc caactactcc    300
gtcgacgaca agatcggcat ctactacgag agaggcagct cgatggaggt ctactacaag    360
gacgtcggct tatgcgacgg cgtctggcct tag                                 393
```

| SEQ ID NO: 34 | moltype = DNA  length = 2434 |
|---|---|
| FEATURE | Location/Qualifiers |
| source | 1..2434 |
| | mol_type = genomic DNA |
| | organism = Citrus sinensis |

SEQUENCE: 34
```
tggtctttgg ttttgtcaat tagatcaatg ttcatttttc caatatatat atatacatac      60
acacacacat gaagtcttac ccccgaagat ttatggaata taagagagaa ttttaaccca    120
taagtttgaa ttcaacgaca tgtctgttca ttatttatcc attcaatctg catcttcctc    180
ttttcagatt ttccgtgttt gttgcgcggt tccttctctt ttaacaaatt agggctcgaa    240
taattttgat tctaccattt aaaaactgaa tgcatagcag gctagcaaga agttcttgtt    300
cataaaatttt tgcagtacct tccggaaatg aatactcaaa agcttaattt tcaggaaaca    360
tttcaaaaaa agcatttgga tttcgggcca ccatcccaat atttcggcga tatccaccac    420
cagcagccct ggatgatgag aacaaccacc cagcagcatc aaaatcttga tcatgctcga    480
tctccgagca caatcttgag ccggtttgag tctccagctt cagcttttta cgcaactgaa    540
agatacatgg ggttttgtca gtatgattcc caagctgctg gtaacaactg ctcacaattt    600
tccaggactt gtgattcttc acaacagttt catttgtatc agtcccctgg agaaaatttt    660
```

```
tctgttttat cagctgaaca agctgtccct ctagaaattc cctggaactt ttacaaatcc    720
cctgaagctt cgtgtatcaa tcccccttgga aaacaatatt caggtccatt tgatgaacat    780
caagatcata gagtaagtag tttcctccc tggagacttt tcattcattt ttttttcttt    840
ttttcattca gaatttgttt ttgattgtgg gtagttttg ttttttttt ctaccttcag    900
gtctctaatg atggttatgg attaacttca cttcacaac agggctacgc ttcacatcaa    960
gagaagcaat ctccaagatt tcttctagt agttctttt caactggacc tgtgatcacg   1020
aacaaaactc gaattagatg gactcaggat cttcatgaaa aatttgtcga atgtgtgaat   1080
cgactagggg gagcagacag taagtgttga tatttattga attttgtcag ttgaaggagc   1140
aaaattttt aattatttgt ttttccactt ttttttttt ttttgaattg gttgattaat   1200
tgcagaggcg acgccgaagg caatattgaa gctgatggat tctgaaggat tgacaatttt   1260
tcatgtgaaa agtcatttgc agaaatatcg aatggccaag tacgtccag atttcctga   1320
aggtatatta aatctgcact ggttttgttg aaattgattt ttttttcttt ttagggtcaa   1380
aattctgata ggaactctgt ttcttttgc aggaaaatta gagaaaagaa gtagcttgaa   1440
tgatttgcct caaatcgatg tcaaagcgta aattcattat attttggaat tttacagaaa   1500
taattgttta gaagtccttc taacaactg taacttccgt ctatggcagc actctgcaaa   1560
tcaaagaggc attacaactt caattagatg tccaaaggcg actgcatgaa caactagagg   1620
tacattccag aagttttgtt taatataatt tctatgaaaa tcctcaatgc caaacattcc   1680
cttaatagcc atggtccaaa aatgtaatct ttgtttcctc catgcaattc aatgttattc   1740
ttgaatggca gagtaaattt gattgatatt cttttgggg tcagattcag agaaaattac   1800
agttgagaat tgaagagcaa gggaagcatc tcaagatgtt gtttgatcaa caacaaaaag   1860
caagtaagga tcactcgaag cctcaaaatt tggaaaagt accagaagat gaccccccat   1920
ttaattttga agggatcgaa ttttcaactt cagagaattc gggaaactcc catttcacgt   1980
aaaagataag ttagttttcat ttaactgaag ctgaaatcgt ttgaaaattt tatacgaaga   2040
gacttggggt tgaagcaaag attattacag ttcgtgccaa tgaatcaaaa atagctgctt   2100
actgttacag agtgaagtat ttacattatg attctacaca cagaagaagt gattacaaag   2160
aagaagtaaa taattacaaa gaagaagtaa atatatattt tacttgttaa taaatcatac   2220
aatggtttgt gtataaaatt tagatctaca ttattgaatc tagtacggat taattcaagc   2280
tccatcatct tgtaacagat acagtgcgac agttttgatt tttgctgctt ggtctgtgta   2340
aagtaggttt caaattttga tttcatgttt tcatcagacg atgagtaggt ggagaaacag   2400
agttgaatac catgatcatt gtatcttctc ttaa                               2434

SEQ ID NO: 35          moltype = DNA  length = 1445
FEATURE                Location/Qualifiers
source                 1..1445
                       mol_type = genomic DNA
                       organism = Citrus sinensis
SEQUENCE: 35
atgaatactc aaaagcttaa ttttcaggaa acatttcaaa aaaagcattt ggatttcggg     60
ccaccatccc aatatttcgg cgatatccac caccagcagc cctggatgat gagaacaacc    120
acccagcagc atcaaaatct tgatcatgct cgatctccga gcacaatctt gagccggttt    180
gagtctccag cttcagcttt ttacgcaact gaaagataca tggggttttg tcagtatgat    240
tcccaagctg ctggtaacaa ctgctcacaa ttttccagga cttgtgattc ttcacaacag    300
tttcatttgt atcagtcccc tggagaaaat ttttctgttt tatcagctga acaagctgtc    360
cctctagaaa ttcccctggaa cttttacaaa tcccctgaag cttcgtgtat caatccccttt    420
ggaaaacaat attcaggtcc atttgatgaa catcaagatc atagagtctc taatgatggt    480
tatggattaa cttcactttc acaacagggc tacgcttcac atcaagagaa gcaatctcca    540
agattttctt ctagtagttc ttttcaact ggacctgtga tcacgaacaa aactcgaatt    600
agatggactc aggatcttca tgaaaaattt gtcgaatgtg tgaatcgact aggggggagca    660
gacaaggcga cgccgaaggc aatattgaag ctgatggatt ctgaaggatt gacaattttt    720
catgtgaaaa gtcatttgca gaaatatcga atggccaagt acgtcccaga atttcctgaa    780
ggaaaattag agaaaagaag tagcttgaat gatttgcctc aaatcgatca ctctgcaaat    840
caaagaggca ttacaacttc aattagatgt ccaaaggcga ctgcatgaac aactagagat    900
tcagagaaaa ttacagttga gaattgaaga gcaagggaag catctcaaga tgttgtttga    960
tcaacaacaa aaagcaagta aggatcactc gaagcctcaa aatttggaaa agtaccaga   1020
agatgacccc ccatttaatt ttgaagggat cgaattttca acttcagaga ttcgggaaa   1080
ctcccatttc acgtaaaaga taagttagtt tcatttaact gaagctgaaa tcgtttgaaa   1140
atttttatacg agaagacttg gggttgaagc aaagattatt acagttcgtg ccaatgaatc   1200
aaaaatagct gcttactgtt acagagtgaa gtatttacat tatgattcta cacacagaag   1260
aagtgattac aaagaagaag taataattaa caaagaagaa gtaaatatat attttacttg   1320
ttaataaatc atacaatggt ttgtgtataa aatttagatc tacattattg aatctagtac   1380
ggattaattc aagctccatc atcttgtaac agatacagtc gacagttttt gattttttgct   1440
gcttg                                                               1445

SEQ ID NO: 36          moltype = DNA  length = 1309
FEATURE                Location/Qualifiers
source                 1..1309
                       mol_type = genomic DNA
                       organism = Citrus sinensis
SEQUENCE: 36
atgaatactc aaaagcttaa ttttcaggaa acatttcaaa aaaagcattt ggatttcggg     60
ccaccatccc aatatttcgg cgatatccac caccagcagc cctggatgat gagaacaacc    120
acccagcagc atcaaaatct tgatcatgct cgatctccga gcacaatctt gagccggttt    180
gagtctccag cttcagcttt ttacgcaact gaaagataca tggggttttg tcagtatgat    240
tcccaagctg ctggtaacaa ctgctcacaa ttttccagga cttgtgattc ttcacaacag    300
tttcatttgt atcagtcccc tggagaaaat ttttctgttt tatcagctga acaagctgtc    360
cctctagaaa ttcccctggaa cttttacaaa tcccctgaag cttcgtgtat caatccccttt    420
ggaaaacaat attcaggtcc atttgatgaa catcaagatc atagagtctc taatgatggt    480
tatggattaa cttcactttc acaacagggc tacgcttcac atcaagagaa gcaatctcca    540
agattttctt ctagtagttc ttttcaact ggacctgtga tcacgaacaa aactcgaatt    600
```

```
agatggactc aggatcttca tgaaaaattt gtcgaatgtg tgaatcgact aggggagca    660
gacaaggcga cgccgaaggc aatattgaag ctgatggatt ctgaaggatt gacaattttt    720
catgtgaaaa gtcatttgca gaaatatcga atgccaagt acgtcccaga atttcctgaa    780
ggaaaattag agaaaagaag tagcttgaat gatttgcctc aaatcgatgt caaagccact    840
ctgcaaatca aagaggcatt acaacttcaa ttagatgtcc aaaggcgact gcatgaacaa    900
ctagagattc agagaaaatt acagttgaga attgaagagc aagggaagca tctcaagatg    960
ttgtttgatc aacaacaaaa agcaagtaag gatcactcga agcctcaaaa tttgaaaaaa   1020
gtaccagaag atgaccccc atttaatttt gaagggatcg aattttcaac ttcagagaat   1080
tcgggaaact cccatttcac gtaaaagata agttagtttc atttaactga agctgaaatc   1140
gtttgaaaat tttatacgag aagacttggg gttgaagcaa agattattac agttcgtgcc   1200
aatgaatcaa aaatagctgc ttactgttac agagtgaagt atttacatta tgattctaca   1260
cacagaagaa gtgattacaa agaagaagta aataattaca agaagaag                1309

SEQ ID NO: 37           moltype = DNA   length = 4122
FEATURE                 Location/Qualifiers
source                  1..4122
                        mol_type = genomic DNA
                        organism = Citrus sinensis
SEQUENCE: 37
tgaagtgtca atacttatat agttcccttt tacaggaaaa agaaatgaac atataagtaa     60
cgctagataa taaaggggaa gtgggaagag ggaatgggga actggttcag gaaaagagag    120
gattctgttc cttcaattaa atagaataag gagtcccctta agcttgcaaa ttggccacca    180
aaaaccccctg aaatgcaccc cccgttaata ttgaattaaa cgaaacatgc atgcttcgat    240
gagtcgatct caaactcaat ggtgccccga cattcatact ttaagctggt aaagagcatc    300
aaaatttcgg gaaaatgatg ctcattctag ctagttgctc atgcgcgtgg cgtaattaag    360
ccagaccaat ttgtagatcc tgctattgag tgctagctga acttattccc                420
atataaataa ccaccaatgg caataattta tacatacagg aggtttacaa tttctggaag    480
tgataccaag cttttgattt tgaatcccat aagcatgaaa gcgataccta acggttaaaa    540
tttttgacaa agaaataacc ccatgcataa taagaaaata ggtttaatct gtgcaactaa    600
tatacatcac agtattcatc caacaataag actagtattt ttagctgctt aatatgcaaa    660
aattattgac taataatagt aagtaattgt tttgacctgc taacgtagga atttgatcgg    720
tcagcgggaa agtatcaatc taatcgcttg aggccaaatt acccttttcga tacatatagc    780
ataggtgaag gcatatgtaa tatgctgtcc cttcaaactt ctaagggtca ttttttagata    840
gtgtccacct aaatggaacc aaaagaaaaa ccttttgttta ttagtggatc tcatgcttac    900
cctgatgcaa agagtcgtct tcatcatcac gcaagaattg tttgtttatt atcggtgtcc    960
ctcacaattg ataaagttat taaacaattt gcttgagcca ttttggaagt atcgagtact   1020
cccttgttta attagatcat gttcaatttg ccgcgtacag aatgatgatc gtaaaataca   1080
atgcttaacc tatgcattct gattaaattta taatgggatt cacaatgtat gcgtaacacc   1140
gttataacta agccaacttt cccagatact actgataatg acaagaactt tcctaaaatg   1200
taaaacaacc atgaagcgtg taggatagaa aatgacttgt aacctaccaa gtgtttaaga   1260
tcagtgatga tttgatgagc aacaaagtca agatttatct tagtaaatgg ctcgttgtaa   1320
tgtatgatta ttttttggaag tgatgaatga tcagttaatt atatgctgta agtgactaag   1380
taagtttgga acttcgggtg tatcaaacgc aaacaagatt aatgttacct ttctctctga   1440
cttggactga ttaaataaga tcaagcattg atgtcgacac cttatgctga agctttacac   1500
atcagatata cggagaaaga gtctcctaat ttcttttata agtaaacgaa attcatacct   1560
tactacattt tgttgctcct cctgatcaga tcatgtcttc gacatcttct atgcaataaa   1620
aataaagaaa gaaagaagaa aagaaagatt aaagttgtgc ccattctgag cattcatcaa   1680
catataaatt gaaagctagc tatacaaatt tattttggt tgcatcattt taaaatgaaa   1740
actgagaaga gaaaggtgct agaacagaga tacagttata gatcttcaca ggaacagctg   1800
ccatgcaagg tgggactcag cttccattct caattcccca acgtagaggg agaaggctca   1860
ttcaagctaa atccagggag ttgtaatgca tctggattca tttgttctag caatttcgca   1920
atgccaaatt cagtattcta tgcagctgag aattgcatgg acttttcaca agatttggac   1980
aattttgatc ttcaatcatc cgttaaagtt cacctgcaat acaatcagaa tcccagtttta   2040
cctaaaaagc agccgcatca agatgcttat cgaaattcac cagcaagtgt tttctcattt   2100
atgcaggacc cggcagaaga agaagcctcc ctgaacgaaa gacaaaaatg tgttagtttc   2160
agtgaatatc agaagcatca agttagtaca taaatatgtg cccttgttttg tatatatata   2220
tgcagctgca ggttgaaggt ggtttaactc cttgcccttg aactgccaga ttctgaaacc   2280
aagctcatat catgttcaga ctcaccatga gaagcagact cccaatacta tgactagtca   2340
tagcaaaacc agaataagat ggactcagca tcttcacaac cgatttgttg aatgcgtaga   2400
gtttcttggt ggtgctgaaa gtactgcaaa accttttttt tttttttccc agtatcggac   2460
tttatttatt gtgttactac tcatcaaatt ttgggtattt gtttgtagag gctactccta   2520
agggaatcct gaaactgatg gacatcgatg gattgaccat ctttcacgtt aaaagtcact   2580
tgcaggtttg atttgttgtt taaatatttt atggctgtca aatataatca taactcaaag   2640
cccttagtttt ttttattttc tttcttctcc tttttatttct tgtattttcca gaaatatcga   2700
acggcaaggc acattccaga aggtatatta ttttcaagtc cctgataatt gatatggttc   2760
ttaaactata aatttacctg tttgcatttg atttcatcct tgtccatgcc aaatgccagt   2820
gcctaaactt catgaatttt gacgcttttg ttgtttgca tcaaatatca acattgattg   2880
gtgtcacaga caagaacaat taacctgaca tcataacgaa aatatatatt tccaaaaaat   2940
aaaaataaaa aaggccatta atatgctttt tgaagagta ctttgtgtat acttggaccc   3000
agcatataga ttatttgatt cttatactttt atattcggaa ttcgcatagt taattcagct   3060
atcgtacgat taatgaaaca tgcttttgtc ccatgacatt tgttggcca aatgctatat   3120
attaaatgag ctgatgtaat tgtcgatctt ccctttaatc tgaattaatt agacctcaaa   3180
agaacaggta ctcgccagtt aacgaaacta atatatcatt tctattttga gatgaccatc   3240
atgggaatag gtttcagcac aaaagggcta ctagattcta ttatgtgaag taagacatac   3300
ataaaaatca tccattaatt accttaggcc tatcaacctg ggattttcag acacaacaat   3360
cgtcttcata ttagacccta atgtaatact aatagaatta gccgggccgc cttagaggct   3420
cagttagaaa tgggggaaa aagttacgtc tcagtaaatt tgctgtgcat tttatgcttt   3480
aattatatat gcgtgtgagt ttcgtatgca ggaaaatcaa agcgtgagag gacaaccgac   3540
ctgaatgcaa tagtaaggct cgactcagaa tcgtaagctt ccggtgctga tcatacatat   3600
```

```
attctccctt taaatatctc aatccttgca ttgacctcaa gtcatattcc tgttttcaac  3660
aaagagagct atagggaagt gatatctaca tgtatgcaat gcaaccatct aaaaattcta  3720
aatatgcatc cttgatctca gcttcattaa cagaggcatg cagcttgtgg aaacattgaa  3780
attgcagcta gatgtccaga agcgcttaca cgaccaactg gaggtaccct tttatcccta  3840
ttgtgattaa ggaattgata ctgatatatg ttcaccacat tataatccct taacagttct  3900
gtttcacttg tctgggttag gtccaaagaa atctacagtt gcagattgaa gaacaaggga  3960
agcagcttac acagatgtta gaccagcaac taaagccaaa caaatctctc gttgattcca  4020
acaacgtgga tatcgagttg caagataacc aaccaaatga tctcaaagac acgcgtccct  4080
tcaacatata aggtttcaag gatgcccttt atccttgcaa tg                    4122

SEQ ID NO: 38          moltype = DNA   length = 1008
FEATURE                Location/Qualifiers
source                 1..1008
                       mol_type = genomic DNA
                       organism = Citrus sinensis
SEQUENCE: 38
atgaaaactg agaagagaaa ggtgctagaa cagagataca gttatagatc ttcacaggaa    60
cagctgccat gcaaggtggg actcagcttc cattctcaat tacccaacgt agagggagaa   120
ggctcattca agctaaatcc agggagttgt aatgcatctg gattcatttg ttctagcaat   180
ttcgcaatgc caaattcagt attctatgca gctgagaatt gcatggactt ttcacaagat   240
ttggacaatt ttgatcttca atcatccgtt aaagttcacc tgcaatacaa tcagaatccc   300
agtttaccta aaaagcagcc gcatcaagat gcttatcgaa gcttaccagc aagtgttttc   360
tcatttatgc aggacccggc agaagaagaa gcctccctga acgaaagaca aaaatgtgtt   420
agtttcagtg aatatcagaa gcatcaaatt ctgaaaccaa gctcatatca tgttcagact   480
caccatgaga agcagactcc caatactatg actagtcata gcaaaccag aataagatgg   540
actcagcatc ttcacaaccg attttgttgca tgcgtagagt ttcttggtgg tgctgaaaag   600
gctactccta agggaatcct gaaactgatg gacatcgatg gattgaccat ctttcacgtt   660
aaaagtcact tgcagaaata tcgaacggca aggcacattc cagaaggaaa atcaaagcgt   720
gagaggacaa ccgacctgaa tgcaatagta aggctcgact cagaatcagg catgcagctt   780
gtggaaacat tgaaattgca gctagatgtc cagaagcgct tacacgacca actgaggtc   840
caaagaaatc tacagttgca gattgaagaa caagggaagc agcttacaga atgttagac   900
cagcaactaa agccaaacaa atctctcgtt gattccaaca acgtggatat cgagttgcaa   960
gataaccaac caaatgatct caaagacacg cgtcccttca acatataa              1008

SEQ ID NO: 39          moltype = DNA   length = 4640
FEATURE                Location/Qualifiers
source                 1..4640
                       mol_type = genomic DNA
                       organism = Solanum tuberosum
SEQUENCE: 39
ccaaaaagca gcgagatagg agtggacctg gcagtcctcc tgctatggcc gttccactct    60
tctctgccca atttcacact tcaattctca cacaaccact tccctcttct cgctcttttt   120
ccgtcgaaa actccttgtct tgctcgtcgt cgtcaactcc catggaacat catgaatcga   180
aattcaagga atttccttat gcatctgttc cgcatagaga gttaatggtg aacttgtat   240
cgactgtgga gaatcgtctt ggagaatctc tacttccttg tactctgcct tctcatgtgc   300
agtattttga gaatgaatct gctactgctc atgcttctct ctatgtcaga tctggaaatt   360
cctcttctca ggtactcttcc gactgattct actacttatt acctattcat tcatttctgc   420
acttgtgcca attatatgta ttagggtatg atataggaat tacttcctgt tggatgtttt   480
gttgaattag tatataggaa tgggttacat ctatgttata aaagcttcta tggaaactca   540
agcggataat ccaattcagg caactatatt tagcaagact gagattcgag tgaatatact   600
cctctctcatc ccattttatc ttaattttgt gttgttgcat cacaatgtta tgaaaacgaa   660
aaagcgcaaa aaaactttaa agtaggccgg gactttaagc ctgaaataca aataaagctt   720
gagctttaat gaaaaaaaga cacaataggg aaaaaaatac aatatattat tatgtatcca   780
agactaataa atataagcat gaataacaaa tctatggaca agaaattga tctttttata   840
ataaagtgtg ataccaatag cttagaaccc ttattcgcaa ggaaaagatt gcttaggga   900
ctgaatgacg acaatgaagt gcacattaag cgaggcaaag tgctcaacat attttgagcc   960
ttgcttctgg gattgagcat tcttaaagca cgcctttgac aacattgttg catcactcct  1020
acgtgagacc aaaaaaatgc gccaagaatt ttctcctaat accctccaat atgaatgatg  1080
tcactgctat cttgtacatg gtgaagataa agaaaacaag aaattattat gtactataga  1140
ataatgattg agaaagctag atcttgtcct ctaattttag tggatttggc ttatacagaa  1200
gagttaatcc attacgaatt gtgcttttgt tgattggcct ttttactatg tatgctaaat  1260
atatcagtct tttaataata gtaacatgaa ttgaaatgcc aaatacttaa ttgtataatg  1320
tgctgatggg agttaagaag atcagcagta cttgtattac tctgtgcatc tgtggtttc  1380
tccatccaat gaagtcagac aagtccttta tcaaatctgt ttttttttag ctaattcaa  1440
atttagtatt tcttgttcaa gccatatatc ttgcccttc tagtaaataa cagtcttata  1500
attccttta attggacatg gctctaagaa aggtgtttgg attatagctt atttaagta  1560
gcttttggct tttaagttcc ttttatttt tgaggtgttt gggaaagaca aaaagtgctt  1620
ttaagcactt atttttaggc gaaaatagta caaaaataag ttaaaaacca aaaattgggc  1680
atgaccaact tatgactttt agcttttagc ttataagca cttaaaaaaa gtcaatccaa  1740
tcaaccctc tgtagatgaa aaaaagcatc ctaattctat aataggttat tatatgggtt  1800
gttagtattc aaaatgttaa ctttctcaaa aaaaaatga tataagccaa atggcaaatg  1860
taaaaatagg cccttaaagc aatgttgtgt ctccttttga gttttaagtc tatcaatgga  1920
ttctggtgtc tagagtctaa agggcatgtt ttgaaagaca ataaacaaaa ggggtgtca  1980
taaaaatcac ataccaaaag gggttgtttg tgaattgtac tgcaaactgc catattttc  2040
acggacgacc cctaacgtcc atttgttaca tttaaaaaat ataaaacaaa cgcaattcgt  2100
gaaatgtggt gcgaattccc actaattttt taatagtttg tagcatgttc tgtgaactgc  2160
atctcaacta gttttgctgt gatcttgtca agtagtttg atctctgctt gttgcccctc  2220
ccctaggttg aggagctgta aggggaaaat tcttatgatc tgcaatctca ccttctcaca  2280
taagctttcc caacttcaat atctggtggc actgagttcc catctgaata ggtgccgagg  2340
```

-continued

```
tagtttgtga actagtatct aaactgaaac aatagaagtt tcttgctctg gtttaaaatt   2400
cagtgcgcat ctcaggaatt tcatagtgta tgcccaatg tgaatggatg acttgaaaat    2460
atgtgattga agtctgtttt gttacagaaa atcaatgtaa acagtgctgt agttgtagta   2520
tgcaatcttg actcttcctt tcaattgaaa ttgactcaca aaaattttcc ttagtttttt   2580
catagtaggt tccttttgatg aatttaccca caatagtcat ttgcaattat tggccgaatt  2640
cacgaaatag tcatcagcag agaaaaatat ggttggctta ccgagatgag tctcatgcct   2700
gatttcaata ggagcttcgg cggttgaggc aatcgccaaa tcagcttgaa cctttctgcg   2760
aaggttggtt tcgatggagc aacacccta cctttccctg ctaaattggg attttctgt     2820
tggagttgaa tattgggggtt tctgatctgg gcttgaaaga ttggttatag caggattttt  2880
atcagtggca gcagggttat gatcagtttc attgatgttg gtcgcggcaa ccgatttcaa   2940
ttttgaagag ggtgtgtcga aatctgagga caatttggc tgaggggggtg tatgattttg   3000
gtgggtggat ttcgaatggg cagtgttttc ctgttgaggt gttgcatggt gatcggaaaa   3060
agagtaggct gagtgttaat ggcatcttgg aggttctgga gaattgttgg gggcaagctt   3120
taggagctta ttactgtcca tgtgttgttc ctctgaaagta ttggaagata tagggggatga 3180
tgttttgttg ttgttgtggt tgttggtgct agaaggagtg gatttggtg agtttgggat    3240
ttctcgggtg gattggttca aactagcaat tgggggttgt aggagagcag gtgtgttttg   3300
ctgagttgtc ggtgtaggag aggctgcagt tggttgagat gagtatggat tgtggatgta   3360
taactagtgt tttaggtggg ttccgatgca ccatttgggt gtttgctgaa aagatcaata   3420
gatcttcata gagagaagct agagagaata tgcatccaaa attgaccaac caatctaaca   3480
gctcgattca agaattatcc ttgtgcataa tttgtagttt actgcatttc tgctagttgc   3540
gttcacccga tatcttcttg gggaagttat acataaggac tgcaaagca tcatggagat    3600
agcaagtagg aagtctaatt agttcatcaa tctaatcttc ctatgcttgt tcattcttga   3660
atttggatct ggcttctgtt catttattct tgtccagttc cattcctctg cttatagtta   3720
gtagttccac tgagagttct ttgacaagtc ttgtttctct ttgagattta aagttcttttt  3780
tctaacgcgt ataataaaag ataaactggg aacacacagt taacgatttc aactttctca   3840
tcaggagtat atgcaaggtt aatattttttg ccttttctaa attgtgacag gttgatttca  3900
tacttggtag ttgggttcac tgcaacctac ccacaggcgg agcgttgaat attacaagcc   3960
tttcagcata tttgagacct tcaactgatg caccaaactt cttaattgaa gttatccgca   4020
gcagtccaac aactctcatc cttattcttg atctacctcc gcgaaaggac cttgtccaac   4080
atcctgatta cctcaagacc ttttatgagg aaacacaatt agcaagcag agacaacttc    4140
tcgagaaatt acctgaggta aagccttact tctcttcgtc tctatatatt cgatccctag   4200
tctctccatt ggctatcttg gtttctatag aaaccgaacc ttcccaggcc attcgcattg   4260
atgagattat tcaggatcac ataagtcctg ttgctaaggt aatgctggat acatggttgg   4320
atctgtgtgc ttgtactgag agaagattga cagatgatga aagtgcagat ctggctaaga   4380
gggatcgaat aattaagaat aagactatcg agatagatct tgaatcaagc ttccctaggc   4440
ttttcgggca agaagtagcg aaccaggttt taggagtact aagggaaatc tacaacagtt   4500
gaatttcttg ctcctgctgc tgttttattg tgtgattatt gtatgtaatc tttataattc    4560
ttcaacatat aatacattta aaaagatgta aattgagagt aactataaaa gttgcattct   4620
tctatttaga gttcttgtca                                              4640
```

```
SEQ ID NO: 40          moltype = DNA   length = 939
FEATURE                Location/Qualifiers
source                 1..939
                       mol_type = genomic DNA
                       organism = Solanum tuberosum
SEQUENCE: 40
atggccgttc cactcttctc tgcccaattt cacacttcaa ttctcacaca accacttccc   60
tcttctcgct cttttttccgt cggaaaaactc ttgtcttgct cgtcgtcgtc aacttccatg  120
gaacatcatg aatcgaaatt caaggaattt ccttatgcat ctgttccgca tagagagtta   180
atggtggaac ttgtatcgac tgtggagaat cgtcttggag aatctctact tccttgtact   240
ctgccttctc atgtgcagta ttttgaaat gaatctgtca ctgctcatgc ttctctctat    300
gtcagatctg gaaattcctc ttctcaggtt gatttcatac ttggtagttg ggttcactga   360
aacctaccca caggcggagc gttgaatatt acaagccttt cagcatattt gagaccttca   420
actgatgcac caaacttctt aattgaagtt atccgcagca gtccaacaac tctcatcctt   480
attcttgatc tacctccgcg aaaggacctt gtccaacatc ctgattacct caagacctt    540
tatgaggaaa cgcaattaga caagcagaga caacttctcg agaaattacc tgaggtctcg   600
tcttatctct cttcgcctct atatattcca cccccaacca ctccatgggt tatattgaat   660
tctatacaaa ccgaaccttc ccaggccatt cgcattgatg atattattca ggatcacata   720
agtcctgttg ctaaggtaat gctggataca tggttggatc tgtgtgcttg tactgagaga   780
agattgacag atgatgaaag tgcagatctg gctaagaggg atcgaataat taagaataag   840
actatcgaga tagatcttga atcaagcttc cctaggcttt tcgggcaaga agtagcgaac   900
caggttttag gagtactaag ggaaatctac aacagttga                          939
```

```
SEQ ID NO: 41          moltype = DNA   length = 2345
FEATURE                Location/Qualifiers
source                 1..2345
                       mol_type = genomic DNA
                       organism = Solanum tuberosum
SEQUENCE: 41
ctattcctac aatccttccc acattacaat aattacaatg tcaagtctct cactcctatt   60
ggttcttgtc gccggccttt tcgctgctgc acttgccgga ccggcgacct tcgccgatga   120
gaatccgatc aggcaagtag tagtttccga agagctggaa aacggaattc ttcaagtcgt   180
cggccagact cgcaatgctc tctccttcgc tcgctttgct atcaggttac taaattcgaa   240
aatgagatac atttctctat cgttttgctt ttataattaa actaatattg ttctatttt    300
gaatgtttat aaaaggcatc ggaaaaggta cgagtccgtt gaggagatca agcaaaggtt   360
cgagatattt ttggacaatc tgaagatgat ccgatcgcat aacagcaaag gactatcata   420
caaactcggt gtcaatggta actttcttat ctttcaacta ggaaaacaag ttcacactta   480
ctaattagtt atttagatta taaaaactca gtatgaacta cttattcatg atgtataaaa   540
aaaacacttt gtagaagtta agttctttct ttattttact tagtaactaa tcaagctaaa   600
```

```
tgaacaattc ttaattgaat tcttatattc atcatatatg cttggataag tgtttgcaac    660
ttatgatcaa tctaattgtt tatcgattac ttttatgttt catggcagag tttaccgacc    720
taacatggga tgagttccgt agacacaagt tggggcatc  tcaaaactgt tctgccacta    780
caaagggcaa tctcaagcta actaacgtcg ttctgccaga gacggtatat ccaatctgaa    840
tgaactccga tcctttatgg ttatatattt ctggagttac tcattagagt taattaaact    900
agtttgtatc taatgcttta ttatttccaa gatggtagag tgcactgagt tgaattttgc    960
tataataaag atagaaacac taaacatcca tccaccgtgt gctgcgttaa ttagtgtgtt   1020
caattggttg cagaaagatt attttttttga tcctaacgaa caccaaattt ccaattttgt   1080
gattatagaa ggactggagg gaagtcggta ttgttagccc agtgaaggca cagggcaagt   1140
gcggatcttg ctggacattc aggtgagaat tagttagaat catgttggac tcctaaaatt   1200
gaaatctaat ggagcaggca tatatatgtg gggttttggc agcactactg gtgcactaga   1260
ggcagcatat gcccaagcat ttgggaaggg aatctctctg tcagagcagc agcttgtgga   1320
ctgtgctgga gcttttaata actttggctg caatgggggg ttgccatcac aagcctttga   1380
gtacattaaa ttcaatggtg gtcttgacac tgaagaagaa tatccataca ccggcaagaa   1440
tggcatatgt aaattctcac aagcaaatat tggtgtcaaa gtcatcagtt ctgtcaatat   1500
taccctggta attaagatct ctttagtttc cttgggatgg aaccaacttt tgccagtgt    1560
tattcagccc atttgtttaa cttattgagc tgctgctttt accaattaca catatggact   1620
cctgattaac atgtgttatt acagggtgct gaagatgaac tgaaatacgc agttgcattg   1680
gttaggcctg ttagtgttgc ttttgaggtg gtaaaaggtt tcaaacagta taagagcgga   1740
gtttacacca gcactgaatg tggcgacact cccatggtaa gtcatctgtc ccgagtaacc   1800
tgagaagatg caattatcta ttatcaccta aataggccta tatggacaat attacaaaca   1860
ctgactgttt cattggcagg acgtaaaacca tgctgttctt gctgtgggtt acggtgttga   1920
aaatggcgtt ccctactggc tcataaagaa ctcatgggga gcagattggg gtgaggatgg   1980
atacttcaaa atggagatgg gaagaacat  gtgtggtgtt cgacttgcg  catcctaccc   2040
aatcgttgcc taagctttgg agttttgtga aaaaattatg cataaatccg tgttgtccca   2100
gttaatgatg cagcagcagc attcaggctc cattctcaga tttatattca gaacatgtat   2160
ggatcgttat acatacaaaa atggtttagg ctacttatat gaaagaaaca ataagatcaa   2220
aatatttagt tcacagagat tattatgcag gaaaagtccc catgtaattt atacattata   2280
agtaatgaaa gggaggaaga aattcttatt gtaagcatta ttaatccact gttgtcctta   2340
gttta                                                                2345

SEQ ID NO: 42           moltype = DNA  length = 1071
FEATURE                 Location/Qualifiers
source                  1..1071
                        mol_type = genomic DNA
                        organism = Solanum tuberosum
SEQUENCE: 42
atgtcaagtc tctcactcct attggttctt gtcgccggcc ttttcgctgc tgcacttgcc     60
ggaccggcga ccttcgccga tgagaatccg atcaggcaag tagtagtttc cgaagagctg    120
gagaacggaa ttcttcaagt cgtcggccag actcgcaatg ctctctcctt cgctcgcttt    180
gctatcaggc atcggaaaag gtacgagtcc gttgaggaga tcaagcaaag gttcgagata    240
tttttggaca atctgaagat gatccgatcg cataacagca aaggactatc atacaaactc    300
ggtgtcaatg agtttaccga cctaacatgg gatgagttcc gtagacacaa gttgggggca    360
tctcaaaact gttctgccac tacaaagggc aatctcaagc taactaacgt cgttctgcca    420
gagacgaagg actggaggga agtcggtatt gttagcccag tgaaggcaca gggcaagtgc    480
ggatcttgct ggacattcag cactactggt gcactagagg cagcatatgc ccaagcattt    540
gggaagggaa tctctctgtc agagcagcag cttgtgact tgctggaggc tttaataac     600
tttggctgca atgggggtt  gccatcacaa gcctttgagt acattaaatt caatggtggt    660
cttgacactg aagaagcata tccatacacc ggcaagaatg gcatatgtaa attctcacaa    720
gcaaatattg tgtcaaagt  catcagttct gtcaatatta cctgggtgc  tgaagatgaa    780
ctgaaatacg cagttgcatt ggttaggcct gttagtgttg cttttgaggt ggtaaaaggtt   840
ttcaaacagt ataagagcgg agtttacacc agcactgaat gtggcgacac tcccatggac    900
gtaaccatg  ctgttcttgc tgtgggttac ggtgttgaaa atggcgttcc ctactggctc    960
ataaagaact catggggagc agattggggt gaggatggat acttcaaaat ggagatggga   1020
aagaacatgt ggtgttgcg  acttgcgca  tcctacccaa tcgttgccta a            1071

SEQ ID NO: 43           moltype =     length =
SEQUENCE: 43
000

SEQ ID NO: 44           moltype = DNA  length = 1632
FEATURE                 Location/Qualifiers
source                  1..1632
                        mol_type = genomic DNA
                        organism = Solanum tuberosum
SEQUENCE: 44
atgcaaacta tcaagcttc  ttccttttca ccatttcacc tcaacttgaa ctcaactagt     60
tcatttccca aaattaccaa cttgtacatt caacaaaatt atgaaaaccc catttcttgt    120
tttccctcaa ttcagagcca aaatgcaaaa ttcaaggttt ttactgctat ttccccaagt    180
gtttcaactg aatcagaaac cccatttgat gaaaggactg aaaatgaaaa tcaagaagag    240
aaatttgagt ggtatgctga gtggtaccca ataatgccaa tttgtgatct tgataagagg    300
aggccacatg gaagaaagt  gatgggtatt gatgtggttg tgtggtggga taagaatgag    360
aaagaatgga agtaatgga  tgattcttgt cctcatagat atgctccact ttctgaagga    420
agaattgatc aatggggaag attgcagtgt gtgtatcatg gttggtgctt taatggagct    480
ggtgattgta agtttatccc tcaagctcct agggatgggc ctccggttca tacgtccaaa    540
agagcttgtg caactgttta tccagttgtg tgcaaaatg  acattcttg  gttttggcca    600
aactctgatc ctctatacaa ggacatatat ttgacgaaaa ggcctcctta tacctgaa     660
cttgatgaca gttcgttttc gaaaaccttc atagtcagag atatatcata tgggtatgag    720
cttctgattg aaaaaccttat ggaccccagct catgtccaat attcacacta tggcattatg    780
```

```
aatgttccag tagccccaa  aagtgtgaaa gctgatagag aaggggggaag accacttgac  840
ataactgtca cgaagttgga tgtaaatgtc attactgcaa accagggacc tggacggaac  900
acatttgttc cgccttgtgt gtattatagt tattttgctt tcggaggacc tcagggaaaa  960
acatctgcta tatcatctgg aactgtacag gaaaaaccct cagctgagaa gcagaaaaaa 1020
gcacttctag ttttcatctg tattccggtt agtccaggtc atagcagaat tatatttgca 1080
tctccaagaa actttgccac ttgggcagat cgaataattc cacgttggat attcacctg  1140
ggacaaaatc taattctgga ttctgatttg tatcttcttc atgtggagga gcgcaagcta 1200
aaggaaattg gctcttacaa ttggcataaa gcttgctatg tgccaacaaa ggcagatgcc 1260
attgttgttg cttttagaag gtggctaaac aaatatgcaa gtggtcaagt tgattggcgt 1320
ggaaagtaca atggggacct cccgccaact cctccaaggg agcagctgct ggacaggtat 1380
tggactcata cagtgaattg cacaagttgc aatcttgcat ataaaggtct caatgctctt 1440
gaagttgtac tgcagatcgc ctccattggt gtgctcggaa ttgttgctgc tgcaaagcag 1500
ggcacattgt cagtggtggc taggtattct ttggtcacca ttgcattact atgcttcgtg 1560
gcctcgagat ggttatctca tttatatac  aaaaattttcc atttccacga ttatgatcac 1620
gcctttcgtt ga                                                     1632

SEQ ID NO: 45         moltype = DNA  length = 4284
FEATURE               Location/Qualifiers
source                1..4284
                      mol_type = genomic DNA
                      organism = Solanum tuberosum
SEQUENCE: 45
gattgacaca agaaaaagaa gcatacactt gaagactagc tagctatatg gaagctctta   60
aaatttctac ttgttttcca ccatttctct tcaacttgaa aacacctaga ttttcaagaa  120
ttatatgtga gaagaaacga aacttttctt tttctctaaa tcatcaacaa ccccacaagt  180
caagattcaa tctttcact  accaatattt ttaattcaac taatgaacca caacaactac  240
ttccaaatga tgaacaagaa attagtacta aaaatgaaaa aaatcaagaa aaagagaaat  300
ttgattggta tgcacaatgg tatccaataa tgccactaag tgaacttgat aagagaaggc  360
cacatggaa  aaaagtgatg ggaattgatt tagtagtgtg gtgggataaa aatttggagg  420
aatggagagt gatggatgat gcttgttctc atagattggc tccactttct caagggagaa  480
ttgatcaatg ggggaagattg cagtgtgtgt atcatggttg gtgttttagt ggttctggtg  540
attgcaagtt cattcctcag gctcctagag acaagcttca tgtaattact actccttttt  600
tatctgtcgt ttaacatatt gacacatcta ttaagaaaat catttgataa tatatgtaac  660
atttttttt  ttctgtttta cgttatttag ttcatttcag ctcaaggctc aaacacgaaa  720
tttctgatta gggttgaaag tatttttgtcc atcctcatct aatccttgga tttttccttt  780
agatgttttt caaagtgaat cacactttaa actttttta  acttctcatt ttacatttag  840
gttaatgacg tacattattt tccattgaca ttataaataa acatgctttt taacttggtc  900
tcagctagac acacacatcc catgtgacgt cctacatgat atttcacaac ctatgtaagt  960
tcctacttgt attatgccaa gtaggacatg tgtgtctatg tgttcctctt tatgcaagtt 1020
taagtatcta cttgtgcaca ctcaaattag ttgaagagca tagatgacaa ctgaggccaa 1080
taaaagactc atttatgcat ttacgctcag atccggaatt ccactgtccg gtacggagtg 1140
tgcataataa ttgacctggg gtatttccac ccccccttcaa tcagtcccgg ggagtttcca 1200
cacacacata tccgggagcc cgcattgaat cggatattga tctactatca tatcaaatta 1260
agatttactc ctaactcatt attgcatata ttcaaggtca atgagttttc caaataaggt 1320
tgtggtgaaa tgatcattaa ttaaatgttt cgacttttca cataattttg tacagttttt 1380
tttatttact tatgacaagg agtgactata tattaatttt ttgtaggttc acacatccaa 1440
aagagcatgt gtagcagtgt atccaagttt tgtgcaaaat gacattcttt ggtttttggcc 1500
caacactgat cctttataca aggacataca cttgagcaaa accccacctt atattccacc 1560
tttagatgat ttaacttcat atgcaaaaac aacacttgtt agagacatcc catatgggta 1620
agtacccttg taaatatatt tggtgtttta ttttggcatg acaaaaaata attttggaa  1680
aaatatttt  aagaaaataa gtcatttttt tgaaaaaaga aaaagttaat aagtcatttt 1740
ctgaagtttg gttaaaatta tcataaagta cttttcaagga aaaacatttt aaaatgactt 1800
ctctcacttt aggcaaaagt cattttccta cacaattatt tcaactctag aaaagtttgc 1860
attagcctat ttattattac ttggtagaat taatatttaa tcagagtttg aaaaatttaa 1920
ttgagaaata attattttt  caggtatgag ttttttgattg aaaacctcat ggacccatct 1980
catgtcaatt atgcacatca tggcataatg aaaattggga aaatagaagt tccaaacaga 2040
taagaaaatt aaaccttaac atatatacaa atacttgatt tgaattttta ttgtatttgg 2100
atattttac  caaactaata atatatattt aatatgtgca ctgtgaaggg tgatagaaga 2160
ggaggaaaac cacttgatat aagccttgaa aaattagaca taaatggatt tattgcaaag 2220
caaggacatg atgaacacaa atttattgcc ccttgtgtgt actatggtcc atttggtgtt 2280
caaagctatt tggataatta tgaatcaaag gtaattatct ttttttcgaat tttctctata 2340
atatcatcgt ttaaccaaat accttttgat tgttataaca tgctattttg ttatagaaa  2400
catataatat aacataaaaa ttgatctaaa taaattggct gctattttaa atgtcctacc 2460
tacccaatgt attcgaggga gaggttagaa tcgaaaaaga tcaggttcca cacatagaag 2520
ataggcagaa ggtatgggac gagtagtatg atgtacggag aaccaagacc agtttaatat 2580
taattaattg ctggatcaaa acaaaaatta accccccccc gccccggaag ttaaactgca 2640
ttgattatat gaagggataa gacactagta ccccattgta cacctttttgg tttacgtggc 2700
acactctgtg actccacgtg gttgaggcgc gtaggatatg tttggatgcc acgtaagcca 2760
aaaagatgta caaaattaca aataaataaa taattaga  ataatagaac cttagtttaa 2820
ttaaggtgtg cctctagatt tgatcatga  tctagaggga tacctgtgct ttatcgctaa 2880
tataaaagat ctttactatg aaagtgtact tctaagattt atttttattg tgatgtgatg 2940
caggaagaat catcatcaaa tgatacaaat agaatatttc tagtatttat atgtgttcca 3000
gtaagtccag gtaattgcag attgatgatg acatccttca gaaactttgc tggttgggag 3060
tataaactat ttccaccatg gaaatttcac cttgacaata acctaatcat tgattctgat 3120
ttatatttac ttcatcttca ggtaattaat tatcctctta caatttttttg atttttactag 3180
tagtcgtaac attaatcttg tcttttgatt ttattataa ataaaaatatt attttttcaa 3240
aatgatttat catgctatct ttagtatttc gtcgtgactt tttcactttt gttatgttag 3300
tttgatattt taatattaat aaaaatgtat catatgtcac gttatgtatc atcacaacct 3360
aactgattgt ttattttatt ttgtcaattt gttttcaact gtaatctatt ataatttatt 3420
```

```
gtatttatgg tatgttacac caacacttta ttatgttttt cgttgagttg agggcctagt    3480
gggaacaatc gttctacctt caaggtaggg gtaagatctg tgtatacact accttcctca    3540
atcttcactt gtggattata ctggtatata tatgttgtat ttcttaaaaa agttgattag    3600
tagaaattaa ttatgttgtt catcagactc tccaaaaata ttatcgctac aatgtgtaat    3660
atttagttcc ttttgaagga gcacaagcta agggaaaaag gtccacagaa ttggcaaaaa    3720
atttgttatg taccaacaaa ggcagatgca cttgtggttg gttttagaag atggttgacc    3780
aaatatggag gtgcccaagt tgattggggc acaaaattta ctggtgactt gcaaccaact    3840
cctgctaggg aacaacttt ggacaggtgt gtatatagct cgatcttaaa ttgtgtgaat    3900
cgtcttatct aaatattata cttgttatat gaatgctaga gtactggaca catacaataa    3960
attgtagcag ttgtagcaga gcatataaaa gtctaaatgt ccttgaaatc attatgcaaa    4020
ttatctctgt tgcttcaatt ggaattgctg ctgcagcaaa ggagagtgtc atgtcaattg    4080
ctgcaagata ttcattggtc ttcttggcat tactatgctt catggcttcc agatggttat    4140
ccaaatttat atacaaaagt ttccatttcc atgattatga tcatgccttt tgttaaatgg    4200
tgtactatgt aatagtattg gagatcctaa acattatgta ttattgagga tattgtgtta    4260
tgaataagat ttctccgtca gtaa                                           4284

SEQ ID NO: 46           moltype = DNA   length = 1632
FEATURE                 Location/Qualifiers
source                  1..1632
                        mol_type = genomic DNA
                        organism = Solanum tuberosum
SEQUENCE: 46
atggaagctc ttaaaatttc tacttgtttt ccaccatttc tcttcaactt gaaaacacct    60
agattttcaa gaattatatg tgagaagaaa cgaaactttt ctttttctct aaatcatcaa    120
caaccccaca agtcaagatt caatctttc actaccaata ttttttaattc aactaatgaa    180
ccacaacaac tacttccaaa tgatgaacaa gaaattagta ctaaaaatga aaaaaatcaa    240
gaaaaagaga aatttgattg gtatgcacaa tggtatccaa taatgccact aagtgaactt    300
gataagagaa ggccacatgg gaaaaaagtg atgggaattg atttagtagt gtggtgggat    360
aaaaatttgg aggaatggag agtgatggat gatgcttgtt ctcatagatt ggctccactt    420
tctcaaggga gaattgatca atggggaaga ttgcagtgtg tgtatcatgg ttggtgtttt    480
agtggttctg gtgattgcaa gttcattcct caggctccta gagacaagct tcatgttcac    540
acatccaaaa gagcatgtgt agcagtgtat ccaagtttg tgcaaaatga cattctttgg    600
ttttggccca acactgatcc tttatacaag gacatacact tgagcaaaac cccaccttat    660
attccacctt tagatgattt aacttcatat gcaaaaacaa cttgttag agacatccca    720
tatgggtatg agttttgat tgaaaacctc atggacccat ctcatgtcaa ttattcacat    780
catggcataa tgaaaattgg gaaaatagaa gttccaaaca gtgtgaaggg tgatagagaa    840
ggaggaaaac cacttgatat aagccttgaa aaattagaca taaatggatt tattgcaaag    900
caaggacatg atgaacacaa atttattgcc ccttgtgtgt actatggtcc atttggtgtt    960
caaagctatt tggataatta tgaatcaaag gaagaatcat catcaaatga tacaaatga    1020
atatttctag tatttatatg tgttccagta agtccaggta attgcagatt gatgatgaca    1080
tccttcagaa actttgctgg ttgggagtat aaactatttc caccatggaa atttcacctt    1140
gacaataacc taatcattga ttctgattta tatttacttc atcttcagga gcacaagcta    1200
agggaaaaag gtccacagaa ttggcaaaaa atttgttatg taccaacaaa ggcagatgca    1260
cttgtggttg gttttagaag atggttgacc aaatatggag gtgcccaagt tgattggggc    1320
acaaaattta ctggtgactt gcaaccaact cctgctaggg aacaactttt ggacaggtac    1380
tggacacata caataaattg tagcagttgt agcagagcat ataaaagtct aaatgtcctt    1440
gaaatcatta tgcaaattat ctctgttgct tcaattggaa ttgctgctgc agcaaaggag    1500
agtgtcatgt caattgctgc aagatattca ttggtcttct tggcattact atgcttcatg    1560
gcttccagat ggttatccaa atttatatac aaaagtttcc atttccatga ttatgatcat    1620
gccttttgtt aa                                                        1632

SEQ ID NO: 47           moltype = DNA   length = 792
FEATURE                 Location/Qualifiers
source                  1..792
                        mol_type = genomic DNA
                        organism = Solanum tuberosum
SEQUENCE: 47
atggctgatc gcgtacatcc tcagagattca tcgccggcga gttcaccgcc atcgtcaaat    60
aactccggcg aagtagccgc gggaactaat acaaagcatg tgccgtcgcc gggaacgtat    120
gttgttcaag taccaaaaga tcaaatctac cggtatcctc caccggggaa ttctcgccgt    180
tacgaagctt tgagaaaacg aaagcctcgt cggagcttct gttgccggtg cgtttgctac    240
actttctctc tccttctaat tctcattatc gcacttggaa tcactgctgc cgttctctac    300
ctcgtcttcc gtcctgaagc tccaaaatac actatatcca acgtcgcgat taagaatttc    360
aacttaactt cgtcgtctcc agtatcgccg gaattcgacg tcacgttccg agctgaaaat    420
cctaacaata agatcggaat ttactaccgg aaaggtagct ccgtcaccgt attctactcc    480
gatgtccgcc tctctaacgg cgaattgccg cgcgttctatc agccaacgaa taacgtaacg    540
gttttttcaga cgccgttaaa aggatcaaac gtcttgcttg gtaacgccgt taagacggcg    600
ttaaggaatg aacagttgaa agggaaagtt ccgtttaagg ttaacatcaa agcgcccgtt    660
aaagttaaag ttggcgccgt taagatgtgg gaaatcaccg ttaaggttaa gtgtgacata    720
acggtgaata cattaacggc caaatcaaaa ataatttctg aagattgtaa atatagtgtt    780
aggctttggt ag                                                        792

SEQ ID NO: 48           moltype = DNA   length = 792
FEATURE                 Location/Qualifiers
source                  1..792
                        mol_type = genomic DNA
                        organism = Solanum tuberosum
SEQUENCE: 48
atggctgatc gcgtacatcc tcagagattca tcgccggcga gttcaccgcc atcgtcaaat    60
```

```
aactccggcg aagtagccgc gggaactaat acaaagcatg tgcggtcgcc gggaacgtat  120
gttgttcaag taccaaaaga tcaaatctac cggtatcctc caccggggaa ttctcgccgt  180
tacgaagctt tgagaaaacg aaagcctcgt cggagcttct gttgccggtg cgtttgctac  240
actttctctc tccttctaat tctcattatc gcacttggaa tcactgctgc cgttctctac  300
ctcgtcttcc gtcctgaagc tccaaaatac actatatcca acgtccgcgt taagaatttc  360
aacttaactt cgtcgtctcc agtatcgccg gaattcgacg ttactgtccg agctgaaaat  420
cctaacaata agatcggaat ttactaccgg aaaggtagct ccgtcaccgt attctactcc  480
gatgtccgcc tctctaacgg cgaattgccg gcgttctatc agccaacgaa taacgtaacg  540
gtttttcaga cgccgttaaa aggatcaaac gtcttgcttg gtaacgccgt taagacggcg  600
ttaaggaatg aacagttgaa agggaaagtt ccgtttaagg ttaacatcaa agcgcccgtt  660
aaagttaaag ttggcgccgt taagatgtgg gaaatcaccg ttaaggttaa gtgtgacata  720
acggtgaata cattaacggc caaatcaaaa ataatttctg aagattgtaa atatagtgtt  780
aggctttggt ag                                                     792

SEQ ID NO: 49          moltype = DNA  length = 3380
FEATURE                Location/Qualifiers
source                 1..3380
                       mol_type = genomic DNA
                       organism = Solanum tuberosum
SEQUENCE: 49
gaggaggttt gactgtattt ctttgttgga aggggcaaaa tcctgttata tatagtagta   60
gtaaattgtt caccttgtaa aatgttatgg tcttatcatt tgttcattcc ttatctacgt  120
tacagaatat ttaaaatata gtcggcattt ggcacttaca tgttgacata ttcatattct  180
ttatattatg tgtatggagt catttagcat ataacaaaaa gaagaagaag aaattaggag  240
caaagattca attttatttt tcaagaatcc ttcatccttt tagtttcttg attttttcgcg  300
ctttttaatt aagacattca ttcaagaaat gcagtttgtt tgttgaaaat attaaaacag  360
aatcacccctt gtttgtgtat tttgataaga gttgctattt tcttgatctt gatcttgact  420
agtcgttttg gcgaaaaaat gagtattcag aactatgaat tagcaagtga ttgcaactta  480
gagttcccac agatgggatt tgtttccag cctgaaaact ctgcagaaaa tggttgtcaa  540
cagcagcagc aacagaattt ttggcctagt actgattcat catcatcgag aacgattata  600
agtcgaatag gatcatcacc ttctgctttt tttgctacag agaggtacct tggattaaca  660
caatatgaaa accaagacaa caataatagt tgttctcaac tatccaagaa tcttggtcct  720
caaactacgt cgtttactca gcaatgtgga aatggattct tggcagattc atcagcacga  780
gttgacaccg attttcctaa gatttcaatg ccatcattca cagatcaca gttttcaagt  840
agtcaaccat ttggtcctga aggactctat ggaaatccct ttagtaatct atcagataca  900
gagaggattt tgcttcttaa gagcaagttg tttagagaaa ttgactcttc aaataggcag  960
cctgcttcaa tcccttttca aggaaatcaa gactatggtg taagtacttg attcttgttt 1020
acataataca gtcaaatctc tctgtaacga ttttgtttct cctgatatgt tttggttgct 1080
atagctagat gttgttatcg agaacatcta atataacgta atatgaaagt ttgttccaaa 1140
gaaaacttgg ctggtataga gaggtctgac tgaagtatag ttttttcaagt atttgaattt 1200
aagtactttc aattgcttgt tgtctacata atacagtcaa acctctctat aacagtgttg 1260
tttgtcctga tatgttttag ttgctatagc gagatgttat tgaaaaccat ctaatattac 1320
gtaatatgaa agtctgttcc aaagaaaact tggccgttat agagaggcct gactgtagta 1380
ttgtttttca gttttttatt ctgactcgag ttatgttcca acaggtctca aataatacat 1440
gtggttttaa cttggtacat ataaggcaac aatctggaag tcaatcagca aatagtttta 1500
acaactctgg atgttctgga ggatctttat cgagtaaggc acgaatcagg tggactcagg 1560
atcttcatga tcgatttgtt gagtgtgtaa atcgtcttgg gggagctgac agtaagtaaa 1620
tttacacatt tttttagctt ttgtttcttt ggaggtgatc attttggcta tggattaatt 1680
gttcttcact tcatttgcca gaggcgacgc caaaggcaat actaaagctg atggattcag 1740
aaggattaac aattttcat gtaaaaagtc atttacaggt acttgttaat atgaaagaaa 1800
tactttcttg gaacactttt tgtatttaga caaaattctg aatcaaatgt tttttccttc 1860
ttgttttgac tagaaatatc gaaatgcaaa gttcatccct gaatcgacag aaggtatgta 1920
ttatccgaaa taagcttcat gtttattatg taagagatat tcatcccaca gcttgaaccc 1980
gtgacttgta gttcatacag agacaatttt atcgttctc caaggctctc ttcattactc 2040
aagcatcagt acagatgtat gctgcttgtt ttatgctttt ttgtgttaat ttctgagcaa 2100
aaaaaaatca aatatgtttc tccaaataca agatccttaa ccacatataa gtatcctcgt 2160
cttgataaac agttaataca ccttatttcc aaacaagttg gagtccgtta tatgaatcct 2220
cacgaaccat gttctaaacc ttcttcgaaa aatcttctct gctttcattt tttatcattt 2280
acgcaacagg tagatccaac atgatgaaaa acacaagaag acatatttc cttaaacaaa 2340
tatgctatta gtaaatctgt tgaagtcttt gaaatctcag aagattgaaa gaacatttc 2400
atcttacttc ttatacaaat cactttaatt ttatttcgta tgatgatgat atgaaatgag 2460
cttttaaatga aggagtgggg gattcgtata gcggacccca acttgtttga gactgaggcg 2520
tagttgttgt ttaaatttga tatttacagc aaactaaaaa cttaatttta actctgcttg 2580
tggaaaaatg ctctctgaga tatactcaaa tctgtcatta catgctaagt acttaatctt 2640
aaagtttcca tctctttctg gaaatgagag ttccctcctt cctatgatgc agggagatct 2700
ggaaaaacag acagcccgaa taatgtgtca cagatcgaca gcaaacgta tgttctttgc 2760
aactatcttg caaatttttc gtgactattt tagctgaaaa gttaccttaa tacagatttc 2820
ttttcagtgg aatgcaaatc aaagaagcat tgcatatgca gctagaagtc cagaggcgtc 2880
ttcacgagca actagaggta catttagtac atgaaaagat ataaatttaa acacttgtag 2940
gcatgcttag agctgaaaca gtatcaaggc aatcttctta aatcttattg tcttctgtt 3000
gttagattca gcggaagtta caattgagga tcgaagaaca aggggagcag ttgaagaaga 3060
tatttgaaca acaacaacaa acaactagga gtctcttgga gacacgaaat tcaagctttt 3120
cgtctcctgc tgatcagttc accccgcacg aagatgaagt tttgctgca gaaagcttca 3180
ataatactca tttccaatct aataagtt acaatgact gtaaacaaca ttagttttac 3240
attttttcag ctagttttg aaagagagtc gacgttagca tttctgtaaa gataattttg 3300
cctcccaagc aaactacaca aaaaaaaat gtatattaca aagtgaagac ataaatatca 3360
tgcaaaaact taaagtactt                                              3380

SEQ ID NO: 50          moltype = DNA  length = 1209
```

-continued

```
FEATURE                 Location/Qualifiers
source                  1..1209
                        mol_type = genomic DNA
                        organism = Solanum tuberosum
SEQUENCE: 50
atgagtattc agaactatga attagcaagt gattgcaact tagagttccc acagatggga  60
ttttgtttcc agcctgaaaa ctctgcagaa aatggttgtc aacagcagca gcaacagaat  120
ttttggccta gtactgattc atcatcatcg agaacgatta taagtcgaat aggatcatca  180
ccttctgctt tttttgctac agagaggtac cttggattaa cacaatatga aaaccaagac  240
aacaataata gttgttctca actatccaag aatcttggtc ctcaaactac gtcgtttact  300
cagcaatgtg gaaatggatt cttggcagat tcatcagcac gagttgacac cgattttcct  360
aagatttcaa tgccatcatt catcagatca cagttttcaa gtagtcaacc atttggtcct  420
gaaggactct atggaaatcc ctttagtaat ctatcagaga aagagaggat tttgcttctt  480
aagagcaagt tgtttagaga aattgactct tcaaataggc agcctgcttc aatccctttt  540
caaggaaatc aagactatgg tgtctcaaat aatacatgtg gttttaactt ggtacatata  600
aggcaacaat ctggaagtca atcagcaaat agttttaaca actctggatg ttctggagga  660
tctttatcga gtaaggcacg aatcaggtgg actcaggatc ttcatgatcg atttgttgag  720
tgtgtaaatc gtcttggagg agctgacaag gcgacgccaa aggcaatact aaagctgatg  780
gattcagaag gattaacaat ttttcatgta aaaagtcatt tacagaaata tcgaaatgca  840
aagttcatcc ctgaatcgac agaagggaga tctggaaaaa cagacagccc gaataatgtg  900
tcacagatcg acagcaaaac tggaatgcaa atcaaagaag cattgcatat gcagctagaa  960
gtccagaggc gtcttcacga gcaactagag attcagcgga agttacaatt gaggatcgaa  1020
gaacaagggg agcagttgaa gaagatattt gaacaacaac aacaaacaac taggagtctc  1080
ttggagacac gaaattcaag catttcgtct cctgctgatc agttcacccc gcacgaagat  1140
gaagtttttg ctgcagaaag cttcaataat actcatttcc aatctaatat aagttacaat  1200
gacatgtaa                                                          1209

SEQ ID NO: 51           moltype = DNA  length = 144
FEATURE                 Location/Qualifiers
source                  1..144
                        mol_type = genomic DNA
                        organism = Solanum tuberosum
SEQUENCE: 51
aagattttta gtatttgatt tatgaatgaa ttttttttt tgagaaatat tttttatttt  60
tactagagta gaaaataatt tttgaaattg aaaatagttt ttaaaaacaa acttaaattt  120
ttttattttt ttttgggggt gggc                                         144
```

METHODS AND COMPOSITIONS FOR PLANT PATHOGEN RESISTANCE IN PLANTS

REFERENCE TO ELECTRONIC SEQUENCE LISTING INCORPORATION OF SEQUENCE LISTING

The application contains a Sequence Listing which has been submitted electronically in .XML format and is hereby incorporated by reference in its entirety. Said .XML copy, created on Sep. 22, 2023, is named "10457-373US5.xml" and is 136,516 bytes in size. The sequence listing contained in this .XML file is part of the specification and is hereby incorporated by reference herein in its entirety.

FIELD OF THE INVENTION

The present disclosure relates to the field of biotechnology. More specifically, the disclosure relates to compositions and methods for producing plants that are resistant to Ca. Liberibacter infection in plants, such as Huanglongbing (HLB), also known as Citrus greening disease.

BACKGROUND

Currently available commercial Citrus plants lack tolerance or resistance to Huanglongbing (HLB), also known as Citrus greening disease. HLB is caused by species of the phloem-limited, gram-negative bacteria of genus Ca. Liberibacter. In the U.S., the predominant pathogenic species is Ca. Liberibacter asiaticus (Las); whereas, Ca. Liberibacter africanus (Laf) and Ca. Liberibacter americanus (Lam) are the predominant pathogenic species in South Africa and Brazil, respectively. Ca. Liberibacter is a vector-transmitted pathogen. The vector organisms are the Asian Citrus psyllid (ACP), Diaphorina citri, and African Citrus psyllid, Trioza erytreae. HLB was first detected in the United States in August 2005 and has rapidly moved into several Citrus producing areas. All commercial Citrus plants are susceptible to HLB, and infected Citrus plants will irrevocably decline. Thus, HLB has resulted in a severe decline in fruit production in Florida, where HLB has become endemic. Currently, HLB management consists of preventing trees from becoming infected, which includes protecting young flush from the Ca. Liberibacter vector organisms and destroying infected plant material. However, due to the lack of rapid curative methods that control HLB, new methods to prevent infection are required to stop the spread of infection and further decline of the U.S. Citrus industry.

SUMMARY

Certain embodiments of the disclosure relate to increasing plant resistance to infection by a bacterial species from the genus Ca. Liberibacter. One aspect of the present disclosure relates to modified Citrus plants comprising genomes in which endogenous genes or regulatory elements thereof may be modified, wherein the modification confers resistance to HLB to the modified Citrus plant relative to a plant of the same variety lacking the modification. The Citrus plant in certain embodiments may be a grapefruit tree, orange tree, sweet orange tree, or mandarin tree. Further provided are plant parts and seeds of the modified Citrus plant. Another aspect of the disclosure is a method of producing a commodity plant product, from the modified Citrus plant. In certain embodiments this method comprises collecting the commodity plant product from the modified Citrus plant. Further provided are commodity plant products produced by this method. In addition to modified Citrus plants, other plants known to be infected by Ca. Liberibacter such as solanaceous crops may be genomically modified to disrupted to confer resistance to such infection.

In certain embodiments, modified endogenous genes may encode any polypeptide that interacts with any Sec-dependent effector (SDE) secreted by a bacterial species from the genus Ca. Liberibacter. In certain embodiments, modified regulatory elements regulate any endogenous gene that may encode any polypeptide that interacts with any SDE secreted by a bacterial species from the genus Ca. Liberibacter. An endogenous gene in particular embodiments may encode PP2-B2/12, Lectin, Cysteine protease, Cysteine protease 15A-like, Papain-like cysteine proteases, Myb family transcription factor, YLS9-like, Cell death suppressor protein Lls1, Acd1-Like, Acd1, accelerated cell death 2 (ACD2) protein, red chlorophyll catabolite reductase-like, NDR1/HIN1-like protein 13 (Cs8g01640), PHL5-like (Cs7g01290). and PHL5 (orange1.1t02259). An SDE in particular embodiments may be Las4025, Las470, Las4065, Las5150, or Las4250.

Still a further aspect of the disclosure is a method of generating a modified plant comprising resistance to Ca. Liberibacter infection. In one embodiment, the method comprises the following steps: (a) introducing a genetic modification into the genome of a plant cell, wherein the modification is to an endogenous gene or regulatory element thereof, wherein a polypeptide encoded by the endogenous gene interacts with an SDE secreted by a bacteria species from the genus Ca. Liberibacter; (b) regenerating the modified plant from the plant cell or a progenitor cell thereof, wherein the plant comprises the modification (i.e. comprises cells that possess the modification); and (c) identifying a plant comprising the modification and the resistance to Ca Liberibacter infection. In a specific example, the plant is a Citrus plant or a solanaceous crop.

In certain embodiments, modified endogenous genes may encode any polypeptide that interacts with any SDE secreted by a bacterial species from the genus Ca. Liberibacter. In certain embodiments, modified regulatory elements regulate any endogenous gene that may encode any polypeptide that interacts with any SDE secreted by a bacterial species from the genus Ca. Liberibacter. An endogenous gene in particular embodiments may encode PP2-B2/12, Lectin, Cysteine protease, Cysteine protease 15A-like, Papain-like cysteine proteases, Myb family transcription factor, YLS9-like, Cell death suppressor protein Lls1, Acd1-Like, Acd1, accelerated cell death 2 (ACD2) protein, red chlorophyll catabolite reductase-like, NDR1/HIN1-like protein 13 (Cs8g01640), PHL5-like (Cs7g01290), and PHL5 (orange1.1t02259). An SDE in particular embodiments may be Las4025, Las470, Las4065, Las5150, or Las4250. In certain embodiments, step (a) comprises a genome-editing technique. In certain embodiments, the genome-editing technique comprises a nuclease, wherein the nuclease introduces a single-strand DNA break or a double-strand DNA break. In certain embodiments, the genome-editing technique comprises a TALEN, a ZFN, meganuclease, or a CRISPR/Cas system. The disclosure still further provides a Citrus plant produced by this and the foregoing methods.

Still yet another aspect of the disclosure is a method for conferring a plurality of plants with a resistance to Ca. Liberibacter infection. In one embodiment, the method comprises the following steps: (a) introducing a genetic modification into a plurality of plants, wherein the modification is to an endogenous gene or regulatory element thereof, wherein a polypeptide encoded by the endogenous gene interacts with an SDE secreted by a bacteria species from the genus Ca. *Liberibacter*; and (b) screening the plurality of plants for the modification and a resistance to Ca. *Liberibacter* infection. The plurality of plants may include *Citrus* plants or solanaceous plants. In certain embodiments, modified endogenous genes may encode any polypeptide that interacts with any SDE secreted by a bacterial species from the genus Ca. *Liberibacter*. In certain embodiments, modified regulatory elements regulate any endogenous gene that may encode any polypeptide that interacts with any SDE secreted by a bacterial species from the genus Ca. *Liberibacter*. An endogenous gene in particular embodiments may encode PP2-B2/12, Lectin, Cysteine protease, Cysteine protease 15A-like, Papain-like cysteine proteases, Myb family transcription factor, YLS9-like, Cell death suppressor protein Lls1, Acd1-Like, Acd1, accelerated cell death 2 (ACD2) protein, red chlorophyll catabolite reductase-like, NDR1/HIN1-like protein 13 (Cs8g01640), PHL5-like (Cs7g01290), and PHL5 (orange1.1t02259). An SDE in particular embodiments may be Las4025, Las470, Las4065, Las5150, or Las4250. In certain embodiments, step (a) comprises a genome-editing technique. In certain embodiments, the genome-editing technique comprises a nuclease, wherein the nuclease introduces a single-strand DNA break or a double-strand DNA break. In certain embodiments, the genome-editing technique comprises a TALEN, a ZFN, meganuclease, or a CRISPR/Cas system. The disclosure still further provides a *Citrus* plant produced by this and the foregoing methods.

BRIEF DESCRIPTION OF THE DRAWINGS

FIGS. 1 A-C show transgenic expression of CLIBASIA_04025 (Las4025) in grapefruit (*Citrus paradisi*) caused HLB-like symptoms. FIG. 1A shows binary plasmid used for transgenic expression of CLIBASIA_04025 (Las4025) in *Citrus*. CsVMV: Cassava vein mosaic virus promoter; CaMV 35S: cauliflower mosaic virus 35S promoter; 35T: cauliflower mosaic virus terminator; NosT: nopaline synthase gene terminator; LB: left border of the T-DNA region; RB: right border of the T-DNA region; GFP: green fluorescent protein; NptII: coding sequence of neomycin phosphotransferase II; and Mature protein: nucleotide sequence encoding the mature CLIBASIA_04025 (Las4025) protein without its signal peptide. FIG. 1B shows transgenic grapefruit plants transformed with empty vector (control) or the vector that expressed CLIBASIA_04025 (Las4025) (T1, T2, and T3). FIG. 1C shows Western blots that confirmed transgenic grapefruit lines T1, T2, and T3 expressed CLIBASIA_04025. For these Western blots, a CLIBASIA_04025 (Las4025)-specific antibody was used; the polypeptide with SEQ ID NO:1 was the antigen used to produce this antibody.

FIG. 2 shows interactions between CLIBASIA_04025 (Las4025) and targets proteins demonstrated by yeast two-hybrid assay. Yeast cells were co-transformed with GAL4 DNA-binding domain (BD) expression vector pGBKT7 and GAL4 activation domain (AD) expression vector pGADT7. The pGBKT7 vector was either empty (EV) or contained CLIBASIA_04025 (Las4025) without its signal peptide cloned in-frame with the BD; and the pGADT7 vector contained either RLK2, Pathogenesis-related protein 10 (Cs9g03630) (PR10), or PP2-B2 (orange1.1t04174) (PP2B2) cloned in-frame with the AD. The negative control was performed with empty-AD and -BD vectors, and the positive control was performed with p53-BD and T-antigen-AD vectors. Cultures of the co-transformed yeast clones were adjusted to an OD600 of 0.2 and then spotted at three dilutions (1/10, 1/100, and 1/1000) on DDO, DDO/X, DDO/X/A, QDO, QDO/X, and QDO/X/A mediums. The images were captured after 4 days of growth. SD: synthetic defined yeast minimal medium; DDO: double dropout media, SD-Leu/-Trp; QDO: quadruple dropout media, SD/-Ade/-His/-Leu/-Trp; X: X-α-Gal; and A: Aureobasidin A.

FIGS. 3 A-B show CLIBASIA_04025 interacted with cysteine protease (Cs4g07410). FIG. 3A shows the interaction between CLIBASIA_04025 (4025) and cysteine protease (CP, Cs4g07410) detected with a Glutathione-S-transferase (GST) pull-down assay. GST/CP was expressed in *E. coli*, immobilized on glutathione sepharose beads, and incubated with *E. coli* lysates containing Maltose-Binding Protein (MBP)-4025. The bound proteins were immunoblotted using anti-GST and anti-MBP antibodies. FIG. 3B shows the interaction between 4025 and CP detected using Bimolecular Fluorescence Complementation (BiFC), in which EYFP fluorescence represents a protein-protein interaction. Expression vectors with 4025 without its signal peptide or CP cloned in-frame with either the N- or C-terminal fragments of EYFP (EYFPN and EYFPC) were synthesized. *Citrus* protoplasts were co-transformed with combinations of EYFPC or EYFPN with 4025 or CP expression vectors. The co-expression of 4025-EYFPN and EYFPC/CP and the co-expression of EYFPC-4025 and CP-EYFPN produced strong signal in the *Citrus* protoplasts; whereas, no detectable fluorescence signal was produced by the negative control combinations.

FIG. 4 shows overexpression of Myb family transcription factor (MYTL, XP_015380888.1) in Duncan grapefruit induced HLB-like symptoms. FIG. 4A shows expression of MYTL in grapefruit driven by the 35S promoter reduced plant growth. FIG. 4B shows the normal amount of starch particles, red stain, that accumulated in wildtype grapefruit. FIG. 4C shows overexpression of MYTL in grapefruit induced greater starch accumulation than displayed by wild-type grapefruits.

FIGS. 5 A-E show SDE15 (identified as CLIBASIA_04025) interacts with CtACD2 protein, which negatively regulate hypersensitive reaction. FIG. 5A. Yeast-two hybrid (Y2H) assay. Full-length SDE15 fused to the GAL4 DNA binding domain (BD) was expressed in combination with full-length CtACD2 fused to the GAL4 activation domain (AD) in the yeast strain Y2HGold. Strains were grown on double dropout medium (DDO) with -Trp and -Leu and screened on quadruple dropout medium (QDO) with -Trp, -Leu, -Ade and -His supplemented with X-α-Gal and Aureobasidin A (QDO/X/A). The empty BD and AD vectors were used as the negative controls. FIG. 5B. Bimolecular fluorescence complementation (BiFC) assay. Coding sequence of SDE15 without signal peptide fused to N-terminal or C-terminal fragments of EYFP vectors pSAT6-nEYFP-C1 and pSAT6-cEYFP-C1-B were co-transformed with full-length CtCtACD2 and CtCtACD1 protein which fused to C-terminal and N-terminal fragments of EYFP vectors pSAT6-nEYFP-C1 and pSAT6-cEYFP-C1-B into *Citrus* protoplasts. The EYFP fluorescence of protoplasts were imaged 1 day after incubation using a Leica fluorescence microscope. For genuine interaction between SDE15 and CtACD2, co-expression of SDE15-$EYFP^N$ and $EYFP^C$-CtACD2 or $EYFP^C$-SDE15 and CtACD2-$EYFP^N$ should give strong fluorescent signals in protoplast. Co-transformations of SDE15-$EYFP^N$ and $EYFP^C$, $EYFP^N$ and $EYFP^C$-SDE15, SDE15-$EYFP^N$ and $EYFP^C$-SDE15, CtACD2-

EYFP$^N$ and EYFP$^C$, EYFP$^N$ and EYFP$^C$-CtACD2, CtACD2-EYFP$^N$ and EYFP$^C$-CtACD2, EYFP$^N$+EYFP$^C$ were used as negative controls which didn't produce any detectable fluorescence signal. FIG. 5C. Glutathione-S-transferase (GST) pull-down assay. GST-SDE15 and GST empty vectors were expressed in *E. coli*, immobilized on glutathione sepharose beads, and incubated with *E. coli* lysate containing MBP-CtACD2. Total cell extract (Input) and eluted protein (Elute) were immunoblotted using the anti-MBP and anti-GST antibody. FIG. 5D. Hypersensitive response (HR) assay. *Agrobacterium tumefaciens* strain GV2260 harboring binary vectors containing SDE15 and CtACD2 were infiltrated into leaves of *N. benthamiana* at the concentration of $10^8$ CFU ml. Two days later, another *Agrobacterium tumefaciens* strain GV2260 harboring the binary vector containing AvrBsT protein that can trigger HR was infiltrated on the same area of the leaves treated before. HR induction was observed and photographed 2-3 days past-inoculation. All experiments were repeated three times with the similar results, and only one leaf was presented. FIG. 5E. Electrolyte leakage associated with HR induced by AvrBsT 2 days post infiltration. Leaf discs of AvrBsT infiltrated plants were floated on deionized water with shaking. The conductivity of the solution was measured after 4 h shaking. Error bars indicate standard error of mean (n=3). Alphabets represent significant differences in different types of samples.

FIGS. 6 A-F Characterization of SDE15. FIG. 6A. Sequence analysis of SDE15. Amino acid sequence of SDE15 (96 aa) with N-terminal signal peptide (highlighted in yellow) predicted using SignalP V4.1. The cleavage site localizes between the $22^{nd}$ and $23^{rd}$ aa (SCG-DT). FIG. 6B. Yellowing and mottling of the leaf were observed in transgenic *Citrus* cultivar 'Duncan' plants constitutively expressing SDE15 compared with the leaf of empty-vector (EV) transgenic *Citrus*. FIG. 6C. SDE15 detection in phloem sap. Phloem sap was isolated from the bark of both healthy and HLB infected *Citrus*. T1: total bark proteins; T2: total bark proteins after phloem sap isolation; P: phloem sap. FIG. 6D. Subcellular localization of SDE15. SDE15-EYFP was co-expressed with the plasma membrane localization-marker PM-CFP or the nucleus localization-marker CFP-nucleus in leaves of *N. benthamiana*. *Agrobacterium* strains carrying the corresponding expression plasmids were infiltrated at the optical density (OD$_{600}$) of 0.2. Subcellular localization of SDE15-EYFP was inspected and photographed 1 day post infiltration. Scale bars: 10 m. FIG. 6E, FIG. 6F. qRT-PCR analysis of SDE15 expression in different Las hosts (FIG. 6E) and in different stages of Las infection (FIG. 6F). Relative transcript abundances were determined using gyrase subunit A of Las (CLIBASIA_00325) and *Citrus* house keeping gene encoding glyceraldehyde-3-phosphate dehydrogenase-C (GAPDH-C) as endogenous controls. Bars represent the mean of eight replicates. Asterisks represent significant differences in the transcript abundance between *Citrus* and psyllids (** p-Value <0.01). Alphabets represent significant differences in samples of different Las infection stages. Error bars indicate standard error of mean (n=6). All experiments were repeated three times with the similar results.

Figure 7A:
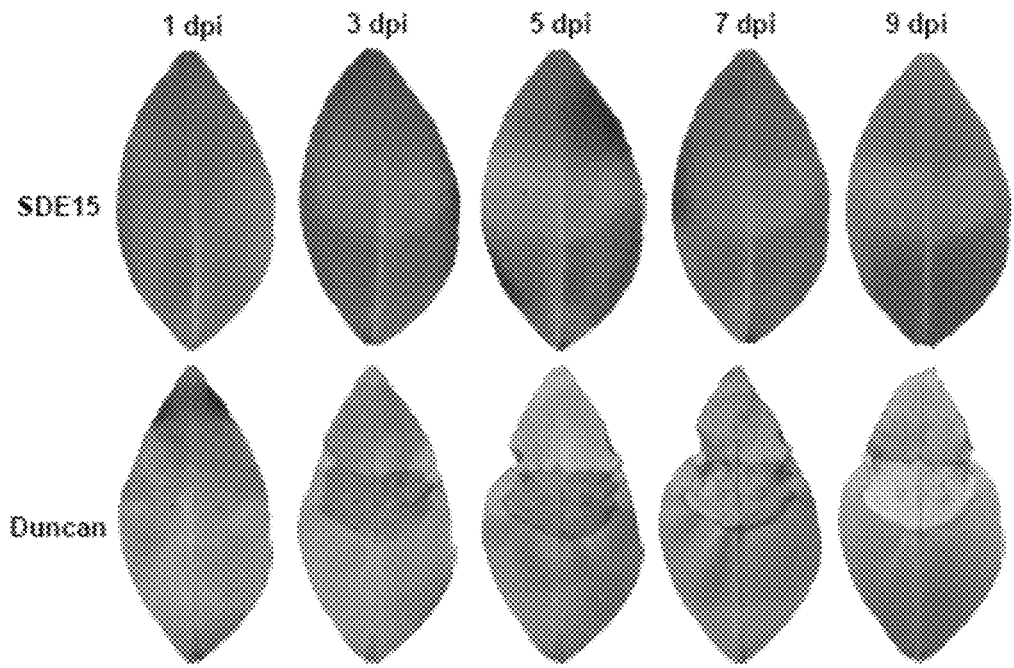
Figure 7B:
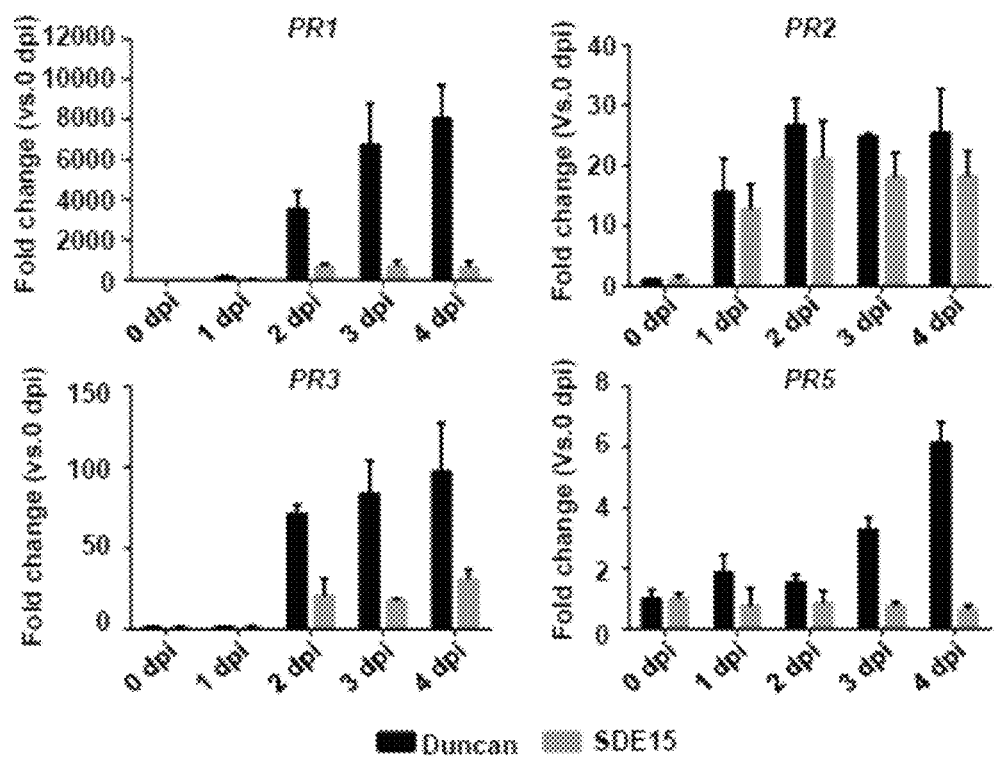
Figures 10A, 10B, 10C, 10D, 10E:
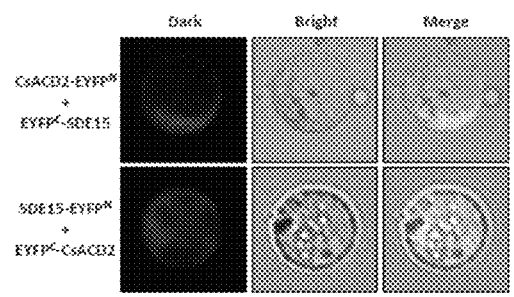

FIGS. 7 A-B. Hypersensitive reaction (HR) was repressed in SDE15-transgenic *Citrus*. FIG. 7A A strong HR, a form of programmed cell death (PCD), was observed in wild type Duncan grapefruit at 3 days after inoculation with *Xanthomonas citri* subsp. *citri* strain A$^w$ (XccA$^W$). Only slight cell death was observed on the XccA$^W$-infiltrated leaves of SDE15-transgenic *Citrus* at 5 days post inoculation. XccA$^W$ cells were infiltrated into *Citrus* leaves at a concentration of $10^8$ CFU/ml. FIG. 7B. qRT-PCR analysis of PR genes. Expression of PR1, PR3 and PR5 was repressed in SDE15-transgenic *Citrus* compared to that in wild type Duncan after HR induction by XccA$^W$. The house keeping gene encoding glyceraldehyde-3-phosphate dehydrogenase-C (GAPDH-C) was used as an endogenous control. Bars represent the mean of four replicates. Error bars indicate standard error of mean. All experiments were repeated three times with the similar results.

Figure 11:
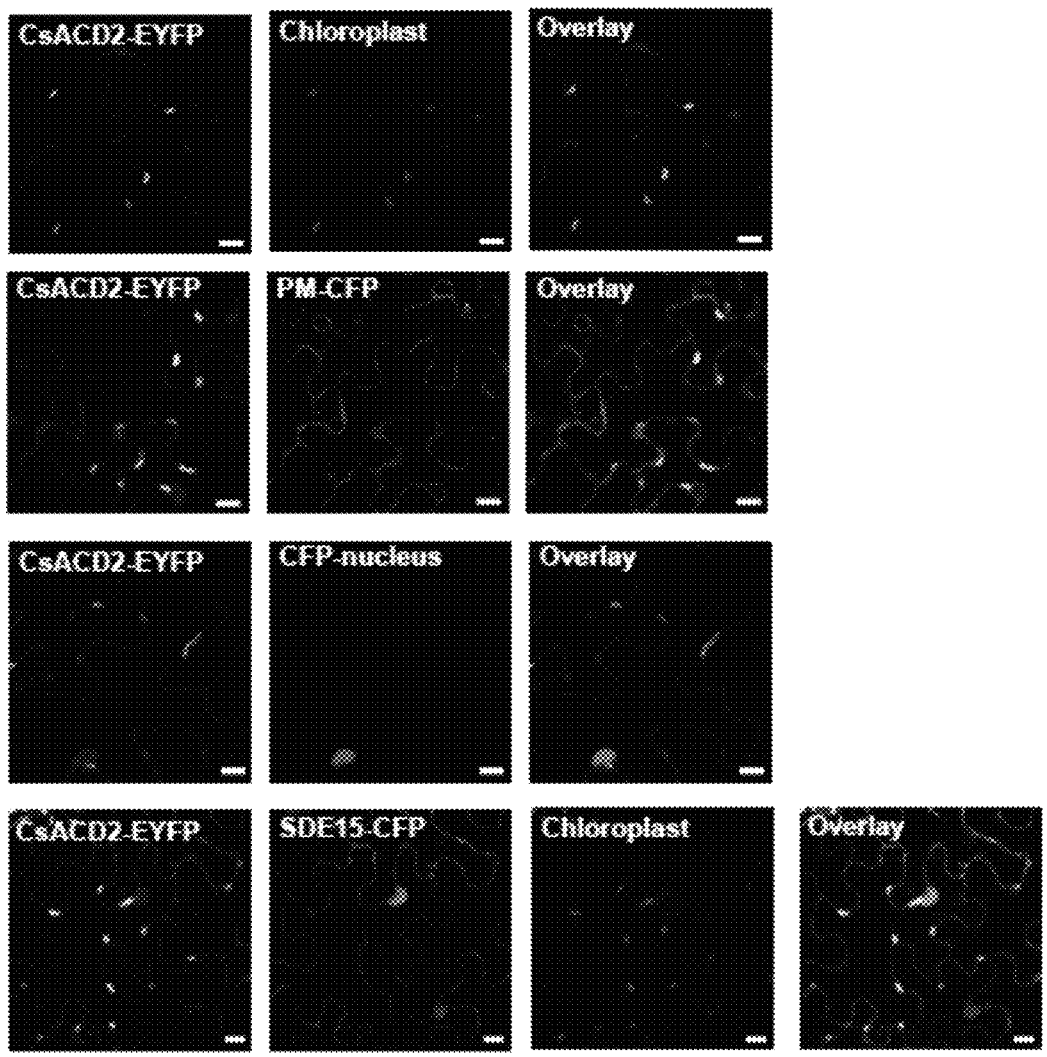

FIG. 8. Transgenic SDE15 *Citrus* plants are more susceptible to HLB. Leaf images taken 3 months post HLB infection via budding grafting. The Las titer in SDE15-transgenic *Citrus* and EV-transgenic control *Citrus* were determined by TaqMan qPCR 0, 1, 2, and 3 months post HLB infection. Each Ct value was represented by Means±standard error ($n_{SDE15}$=7, $n_{EV}$=5). Asterisks represent significant differences in the Las titer between SDE15-transgenic *Citrus* and non-transgenic control (** p-Value <0.01).

FIGS. 9 A-B SDE15-transgenic *Citrus* became more susceptible to *Citrus* canker caused by a virulent strain (XacA 306) of *Xanthomonas citri* pv. *citri*. FIG. 9A. Water-soak symptom (grey color) was observed on SDE15-transgenic *Citrus* at 5 days post XacA 306 inoculation. FIG. 9B. Bacterial population increase of XacA 306 in SDE15-transgenic *Citrus* was faster than in non-transgenic Duncan grapefruit. Bacterial cells were infiltrated into *Citrus* leaves at a concentration of $10^6$ CFU/ml. Error bars indicate standard error of mean (n=4). Asterisks represent significant differences in the bacteria population between SDE15-transgenic *Citrus* and non-transgenic control ( p-Value <0.01, * p-Value <0.001).

FIGS. 10 A-E. SDE15 interacts with CsACD2 protein. FIG. 10A. Yeast-two hybrid (Y2H) assay using SDE15 as the bait and full-length CsACD2 protein as prey. Full-length SDE15 fused to the GAL4 DNA binding domain (BD) was expressed in combination with full-length CsACD2 fused to the GAL4 activation domain (AD) in the yeast strain Y2HGold. Strains were grown on double dropout medium (DDO) with -Trp and -Leu and screened on quadruple dropout medium (QDO) with -Trp, -Leu, -Ade and -His supplemented with X-α-Gal and Aureobasidin A (QDO/X/A). The empty BD and AD vectors were used as the negative controls. FIG. 10B Bimolecular fluorescence complementation (BiFC) assay. The coding sequence of SDE15 (without its signal peptide) fused to that of the N-terminal or C-terminal fragment of EYFP in vectors pSAT6-nEYFP-C1 and pSAT6-cEYFP-C1-B, respectively, was co-transformed into *Citrus* leaf protoplasts with full-length CsACD2 or CsACD2 protein which fused to the C-terminal or N-terminal fragment of EYFP in vectors pSAT6-nEYFP-C1 and pSAT6-cEYFP-C1-B. The EYFP fluorescence of protoplasts were imaged, 1 day after incubation, using a Leica fluorescence microscope. Co-transformations of SDE15-$EYFP^N$ and EYFPC, $EYFP^N$ and $EYFP^C$-SDE15, SDE15-$EYFP^N$ and $EYFP^C$-SDE15, CsACD2-$EYFP^N$ and $EYFP^C$, $EYFP^N$ and $EYFP^C$-CsACD2, CsACD2-$EYFP^N$ and $EYFP^C$-CsACD2, $EYFP^N$+$EYFP^C$ were used as negative controls, which did not produce any detectable fluorescence signal. FIG. 10C, FIG. 10D, FIG. 10E. Glutathione-S-transferase (GST) pull-down assay. GST-SDE15 and GST empty vectors were expressed in *E. coli*, immobilized on glutathione sepharose beads, and incubated with *E. coli* lysate containing MBP-CsACD2. Total cell extract (Input) and eluted protein (Elute) were immunoblotted using the anti-MBP and anti-GST antibody.

FIG. 11. Subcellular localization of CsACD2 and co-localization of SDE15 and CsACD2. CsACD2-EYFP was co-expressed with the plasma membrane localization-marker PM-CFP, the nucleus-marker CFP-nucleus or SDE15-CFP in leaves of *N. benthamiana*. *A. tumefaciens* strain GV2260 harboring the corresponding plasmids were infiltrated into leaves at $OD_{600}$ of 0.2. Subcellular localization was inspected and photographed 1 day post infiltration. Scale bars: 10 m.

Figure 12A:
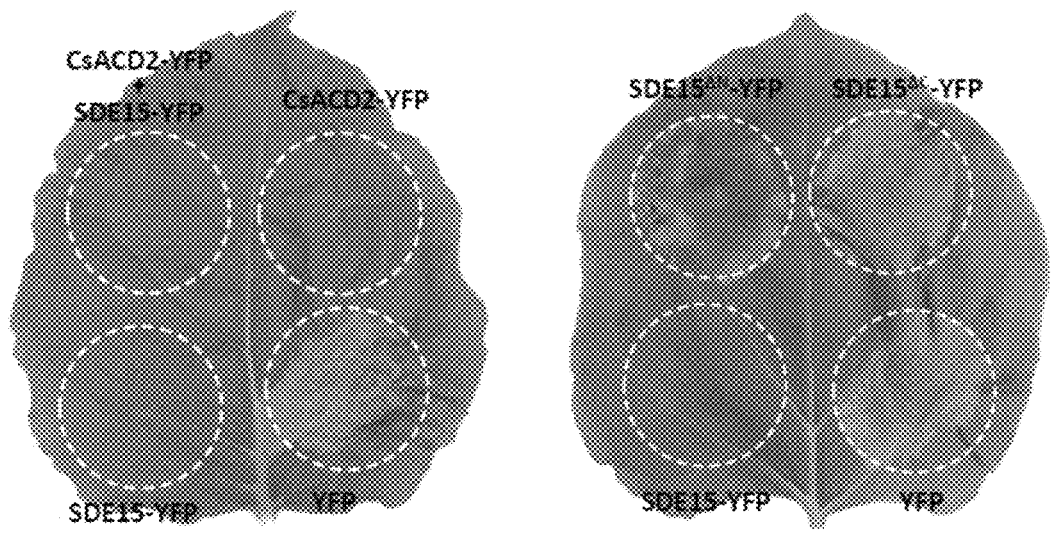
Figure 12B:
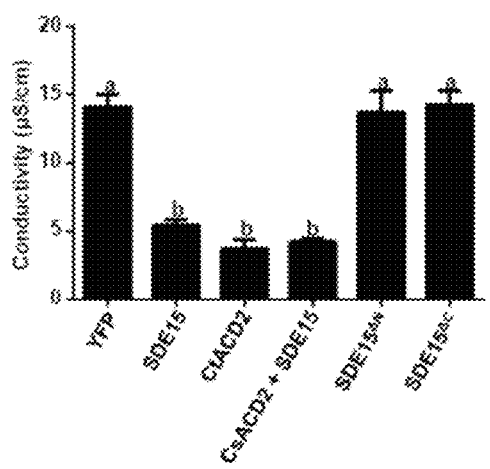
Figure 12C:
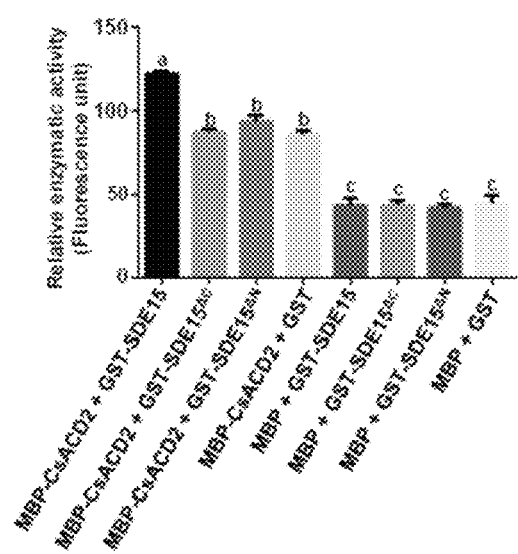

FIGS. 12 A-C. SDE15 represses the hypersensitive response in tobacco and promotes the RCCR activity of CsACD2 in vitro. FIG. 12A. Hypersensitive response (HR) assay. *A. tumefaciens* strain GV2260 harboring binary vectors that are designed to express SDE15, CsACD2 (Left) or truncated SDE15 (Right) were co-infiltrated into leaves of *N. benthamiana* at the concentration of $10^8$ CFU ml$^{-1}$. Two days later, another *A. tumefaciens* strain GV2260 harboring the binary vector that is designed to express AvrBsT protein, which can trigger an HR was infiltrated on the same area of the leaves. HR induction was observed and photographed 2-3 days past-inoculation. All experiments were repeated three times with the similar results. FIG. 12B. Electrolyte leakage associated with the HR induced by AvrBsT 2 days post infiltration. Leaf discs were floated on deionized water with shaking. The conductivity of the solution was measured after 4 h shaking. Error bars indicate standard error of mean (n=3). Alphabets represent significant differences in different types of samples. FIG. 12C. Coupled PAO/RCCR assay to measure CsACD2 activity. Activity of purified recombinant CsACD2 was assessed in a coupled assay using purified PAO and co-factors. pFCC as the product was measured by HPLC. Purified GST-SDE15, SDE15$^{\Delta N}$ or SDE15$^{\Delta C}$ were added to the reaction mixture to examine whether full-length SDE15 and truncated SDE15 proteins affect the activity of CsACD2. As negative controls, purified GST protein or mock purification of the vector alone without CsACD2 was added to the reaction system. Error bars represent SD (n=3). This experiment was done twice with similar results.

BRIEF DESCRIPTION OF THE SEQUENCES

SEQ ID NO:1 Antigen sequence used to produce CLIBASIA_04025 (Las4025)-specific antibody from Ca. *Liberibacter asiaticus*.

SEQ ID NO:2 CLIBASIA_04025 cDNA sequence from Ca. *Liberibacter asiaticus*.

SEQ ID NO:3 CLIBASIA_00470 cDNA sequence from Ca. *Liberibacter asiaticus*.

SEQ ID NO:4 CLIBASIA_04065 cDNA sequence from Ca. *Liberibacter asiaticus*.

SEQ ID NO:5 CLIBASIA_05150 cDNA sequence from Ca. *Liberibacter asiaticus.*

SEQ ID NO:6 CLIBASIA_04250 cDNA sequence from Ca. *Liberibacter asiaticus.*

SEQ ID NO:7 ACD2 Cs1g22670 gene sequence from *Citrus sinensis* cultivar Valencia.

SEQ ID NO:8 ACD2 Cs1g22670.1 cDNA sequence from *Citrus sinensis* cultivar Valencia.

SEQ ID NO:9 AT4G37000 DNA sequence from *Arabidopsis thaliana.*

SEQ ID NO:10 AT4G37000 protein sequence from *Arabidopsis thaliana.*

SEQ ID NO:11 Cysteine Protease Cs4g07410 gene sequence from *Citrus sinensis* cultivar Valencia.

SEQ ID NO:12 Cysteine Protease Cs4g07410.1 cDNA variant sequence from *Citrus sinensis* cultivar Valencia.

SEQ ID NO:13 Cysteine Protease CS4g07410.2 cDNA variant sequence from *Citrus sinensis* cultivar Valencia.

SEQ ID NO:14 RCCR-like Cs1g22680 gene sequence from *Citrus sinensis* cultivar Valencia.

SEQ ID NO:15 RCCR-like Cs1g22680.1 cDNA sequence from *Citrus sinensis* cultivar Valencia.

SEQ ID NO:16 Lls1 Cs9g02990 gene sequence from *Citrus sinensis* cultivar Valencia.

SEQ ID NO:17 Lls1 Cs9g02990.1 cDNA sequence from *Citrus sinensis* cultivar Valencia.

SEQ ID NO:18 ACD1-like Cs9g03000 gene sequence from *Citrus sinensis* cultivar Valencia.

SEQ ID NO:19 ACD1-like Cs9g03000.1 cDNA sequence from *Citrus sinensis* cultivar Valencia.

SEQ ID NO:20 ACD1 Cs8g15480 gene sequence from *Citrus sinensis* cultivar Valencia.

SEQ ID NO:21 ACD1 Cs8g15480.1 cDNA sequence from *Citrus sinensis* cultivar Valencia.

SEQ ID NO:22 Cysteine Proteinase 15A-like Cs3g25530 gene sequence from *Citrus sinensis* cultivar Valencia.

SEQ ID NO:23 Cysteine Proteinase 15A-like Cs3g25530.1 cDNA sequence from *Citrus sinensis* cultivar Valencia.

SEQ ID NO:24 Myb orange1.1t02260 gene sequence from *Citrus sinensis* cultivar Valencia.

SEQ ID NO:25 Myb orange1.1t02260.1 cDNA sequence from *Citrus sinensis* cultivar Valencia.

SEQ ID NO:26 YLS9-like Cs2g29120 gene sequence from *Citrus sinensis* cultivar Valencia.

SEQ ID NO:27 YLS9-like Cs2g29120.1 cDNA sequence from *Citrus sinensis* cultivar Valencia.

SEQ ID NO:28 Lectin orange1.1t05126 gene sequence from *Citrus sinensis* cultivar Valencia.

SEQ ID NO:29 Lectin orange1.1t05126.1 cDNA sequence from *Citrus sinensis* cultivar Valencia.

SEQ ID NO:30 PP2-B2/12 orange1.1t04174 gene sequence from *Citrus sinensis* cultivar Valencia.

SEQ ID NO:31 PP2-B2/12 orange1.1t04174.1 cDNA sequence from *Citrus sinensis* cultivar Valencia.

SEQ ID NO:32 NDR1/HIN1-like protein 13 Cs8g01640 gene sequence from *Citrus sinensis* cultivar Valencia.

SEQ ID NO:33 NDR1/HIN1-like protein 13 Cs8g01640.1 cDNA sequence from *Citrus sinensis* cultivar Valencia.

SEQ ID NO:34 PHL5 orange1.1t2259 gene sequence from *Citrus sinensis* cultivar Valencia.

SEQ ID NO:35 PHL5 orange1.1t02259.1 cDNA variant sequences from *Citrus sinensis* cultivar Valencia.

SEQ ID NO:36 PHL5 orange1.1t02259.2 cDNA variant sequences from *Citrus sinensis* cultivar Valencia.

SEQ ID NO:37 PHL5-like Cs7g01290 gene sequence from *Citrus sinensis* cultivar Valencia.

SEQ ID NO:38 PHL5-like Cs7g01290.1 cDNA sequence from *Citrus sinensis* cultivar Valencia.

SEQ ID NO:39 ACD2 LOC102591737 gene sequence from *Solanum tuberosum.*

SEQ ID NO:40 ACD2 NM_001318612.1 CDS sequence from *Solanum tuberosum.*

SEQ ID NO:41 Cysteine Proteinase 3 LOC102578939 gene sequence from *Solanum tuberosum.*

SEQ ID NO:42 Cysteine Proteinase 3 XM_006342320.2 CDS sequence from *Solanum tuberosum.*

SEQ ID NO:43 Lls1 LOC102597185 gene sequence from *Solanum tuberosum* (bp 734-7789).

SEQ ID NO:44 Lls1 XM_006364374.2 CDS sequence from *Solanum tuberosum.*

SEQ ID NO:45 Lls1/ACD1-like LOC102604461 gene sequence from *Solanum tuberosum.*

SEQ ID NO:46 Lls1/ACD1-like XM_006340026.2 CDS sequence from *Solanum tuberosum*.

SEQ ID NO:47 YLS9-like LOC102602250 gene sequence from *Solanum tuberosum*.

SEQ ID NO:48 YLS9-like NM_001289011.1 CDS sequence from *Solanum tuberosum*.

SEQ ID NO:49 Myb family transcription factor LOC102578723 gene sequence from *Solanum tuberosum*.

SEQ ID NO:50 Myb family transcription factor XM_006362170.2 CDS sequence from *Solanum tuberosum*.

SEQ ID NO:51 Lls1 LOC102597185 gene sequence from *Solanum tuberosum* (bp 1-144).

DETAILED DESCRIPTION

Introduction

The disclosure provides a modified plant comprising a genetic modification to an endogenous gene or regulatory element thereof, wherein it is believed that the polypeptide encoded by said endogenous gene interacts with Sec-dependent pathway effector polypeptides secreted by pathogenic species of Ca. *Liberibacter*. The cysteine protease gene may be modified such that expression of the endogeneous gene is knocked-down or reduced, or otherwise modified such that interaction with SDE is reduced. In specific examples, the endogenous gene is cysteine protease and the modified plant is *Citrus*, wherein the *Citrus* plant exhibits increased resistance to HLB as a result of the modification. Also provided are seeds, fruit, and plant parts of such plants. In another embodiment, methods are provided for generating a modified plant that is tolerant to Ca. *Liberibacter* infection, such as *Citrus* plant that is tolerant to HLB. Methods are also provided for conferring plants with resistance to Ca. *Liberibacter* infection, such as conferring *Citrus* plants with a resistance to HLB, and screening that plurality of plants for said resistance. In specific examples this is accomplished using nucleic acid modification techniques, genome recombination techniques, genome editing techniques, or a combination thereof.

Definitions

Expression: The term "expression" as used herein refers to the transcription of a particular nucleic acid sequence to produce sense or antisense RNA or mRNA, and/or the translation of an mRNA molecule to produce a polypeptide, with or without subsequent post-translational events. Expression also encompasses production of a functional nucleic acid (e.g., an RNAi, antisense molecule, ribozyme, aptamer, etc.).

Genome editing: Modifying a genome with techniques that employ targeted mutagenesis to activate DNA repair pathways. These techniques include, but are not limited to, those that utilize endonucleases to generate single-strand and double-strand DNA breaks that activate DNA repair pathways. Genome editing techniques may also comprise systems that enable targeted editing at any genomic locus. These targeting systems include, but are not limited to, polypeptides, such as, Transcription Activator-Like Effectors (TALEs) and zinc fingers (ZFs), or nucleic acids, such as, Clustered Regularly Interspaced Short Palindromic Repeats/Cas (CRISPR/CAS) single guide RNAs or NgAgo (Argonaute) single strand DNAs. As used herein, "genome editing" and "genome-engineering" are interchangeable.

Genetic modification: A DNA sequence difference, epigenetic difference, or combination thereof between two genomes of the same species in which one genome is identified as the modified genome and the other is identified as the unmodified genome and the DNA sequence or epigenetic difference is the result of applying genome modifying techniques to the unmodified genome to yield the modified genome. A genetic modification, as used herein, encompasses any insertion, deletion, or substitution of a nucleotide sequence of any size and nucleotide content, any epigenetic modification to any number of nucleotides, or a combination thereof. A genetic modification, as used herein, may also encompass introduction of one or more exogenous coding nucleic acids that do not integrate into the unmodified genome, yet are capable of autonomous replication. In certain embodiments, a modification to an endogenous gene or regulatory element thereof may be a deletion, a substitution, or an insertion that reduces expression of the endogenous gene or the polypeptide for which it encodes. In specific embodiments, the modification may be an indel, wherein the indel may cause a frameshift mutation, a missense mutation, a nonsense mutation, a neutral mutation, or a silent mutation. In specific embodiments, a modification to a regulatory element of an endogenous gene may alter or eliminate a function of the regulatory element. In further contemplated embodiments, the modification may comprise a nucleic acid sequence that provides exogenous control of endogenous gene, mRNA, or polypeptide expression levels. In specific embodiments, the modification may also disrupt a post-translational process of a polypeptide encoded by an endogenous gene. Post-translational processes in certain embodiments may be post-translational modification, protein sorting, or proteasomal degradation.

Genetically modified cell: A cell in which the endogenous genome has been genetically modified; a cell in which one or more exogenous, coding nucleic acids have been introduced that do not integrate into the genome, yet are capable of autonomous replication; or a combination thereof.

Genetically modified plant: A plant comprising at least one genetically modified cell. A genetically modified plant may be regenerated from a genetically modified cell or plant part comprising genetically modified cells, and thus the genetic modification may be heritable and inherited by progeny thereof. The progeny thereof that inherit the genetic modification are also considered genetically modified plants. A genetically modified plant, as used herein, also refers to a plant in which at least one genetically modified cell is introduced to a plant or arises as a result of genetic modification techniques directly applied to the plant.

Genetic modification techniques: Any technique known to those in the art that can modify the genome of a cell including, but not limited to, genome editing, site-specific genetic recombination, epigenetic modifications, and genetic transformation.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be from another species, organism, plant, tree, or variety, or may be native to the host genome, but be rearranged with respect to other genetic sequences within the host sequence. For example, a regulatory sequence may be heterologous in that it is linked to a different coding sequence relative to the native regulatory sequence. In addition, a particular recombinant DNA molecule may be heterologous with respect to a cell or organism into which it is inserted when it would not naturally occur in that particular cell or organism.

Overexpress: As used herein, "overexpress" refers to increased expression of a gene or coding sequence over that found in nature or a control plant or tissue. In some embodiments, "overexpress" may refer to greater expression of a gene or coding sequence in a genetically modified plant, when compared to a plant lacking the genetic modification.

Plant: As used herein, the term "plant" refers to *Citrus* or solanaceous plant, or any other plant that can be infected by a Ca *Liberibacter* species.

Plant part: The term "plant part" refer to cells, tissues, organs, seeds, and severed parts (e.g., roots, leaves, and flowers) that retain the distinguishing characteristics of the parent plant. "Seed" refers to any plant structure that is formed by continued differentiation of the ovule of the plant, following its normal maturation point at flower opening, irrespective of whether it is formed in the presence or absence of fertilization and irrespective of whether or not the seed structure is fertile or infertile. A plant part may be any part of the plant from which another plant may arise.

Promoter: A recognition site on a DNA sequence or group of DNA sequences that provides an expression control element for a structural gene and to which RNA polymerase specifically binds and initiates RNA synthesis (transcription) of that gene.

$R_0$ genetically modified plant: A plant that has been genetically modified or has been regenerated from a plant cell or cells that have been genetically modified.

Reduction of Expression: The term "Reduc(e), (es) or (ing) the expression" of a gene or polypeptide in a plant or a plant cell includes inhibiting, interrupting, knocking-out, or knocking-down the gene or polypeptide, such that transcription of the gene and/or translation of the encoded polypeptide is reduced as compared to a corresponding control plant, plant cell, or population of plants or plant cells in which expression of the gene or polypeptide is not inhibited, interrupted, knocked-out, or knocked-down. "Reduced expression" encompasses any decrease in expression level (e.g., a decrease of 10% or more, 20% or more, 30% or more, 40% or more, 50% or more, 60% or more, 70% or more, 80% or more, 90% or more, or even 100%) as compared to the corresponding control plant, plant cell, or population of plants or plant cells. In some embodiments, reducing expression by 50% or more may be particularly useful. Expression levels can be measured using methods such as, for example, reverse transcription-polymerase chain reaction (RT-PCR), Northern blotting, dot-blot hybridization, in situ hybridization, nuclear run-on and/or nuclear run-off, RNase protection, or immunological and enzymatic methods such as ELISA, radioimmunoassay, and western blotting Regeneration: The process of growing a plant from a plant cell (e.g., plant protoplast, callus, or explant).

Rootstock: As used herein, a "rootstock" refers to underground plant parts such as roots, from which new aboveground growth of a plant or tree can be produced. In accordance with the disclosure, a rootstock may be used to grow a different variety through asexual propagation or reproduction such as grafting. As used herein, a "scion" refers to a plant part that is grafted onto a rootstock variety. A scion may be from the same or a different plant type or variety.

Site-specific genome modification: Any genome modification technique that employs an enzyme that can modify a nucleotide sequence in a sequence-specific manner. Site-specific genome modification enzymes include, but are not limited to, nucleases, endonucleases, recombinases, invertases, transposases, methytransferases, demethlylases, aminases, deaminases, helicases, and any combination thereof.

Transformation construct: A chimeric DNA molecule which is designed for introduction into a host cell by genetic transformation. Preferred transformation constructs will comprise all of the genetic elements necessary to direct the expression of one or more exogenous nucleic acid sequences. In particular embodiments of the instant disclosure, it may be desirable to introduce a transformation construct into a host cell in the form of an expression cassette.

Transgene: A segment of DNA which has been incorporated into a host genome or is capable of autonomous replication in a host cell and is capable of causing the expression of one or more nucleic acid sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was modified with the DNA segment.

Vector: A DNA molecule designed for transformation into a host cell. Some vectors may be capable of replication in a host cell. A plasmid is an exemplary vector, as are expression cassettes isolated therefrom.

Tolerance or resistance: Tolerance encompasses any relief from, reduced presentation of, improvement of, or any combination thereof of any symptom of an infection by a Ca. *Liberibacter* species. Resistance encompasses tolerance as well as a reduction of bacteria upon infection or reduction of ability to infect by a Ca. *Liberibacter* species. In specific embodiments of the disclosure, *Citrus* plant may be provided that are defined as comprising a complete or less than complete resistance or tolerance to HLB. This may be assessed, for example, relative to a *Citrus* plant not comprising a genetic modification according to the disclosure.

Hypersensitive Response (or Reaction): The hypersensitive response (or sometimes referred to a hypersensitive reaction) (HR) is plant defense mechanism that protects a plant against infection by a plant pathogen. HR is a form of cell death often associated with plant resistance to pathogen infection to prevent the spread of the potential pathogen from infected to uninfected tissues. Cell death is activated by recognition of pathogen-derived molecules by the resistance (R) gene products, and is associated with the massive accumulation of reactive oxygen species (ROS), salicylic acid (SA), and other pro-death signals such as nitric oxide (NO). Ca. *Liberibacter* species inhibit hypersensitive response, which inhibits the plant from defending itself against the Ca. *Liberibacter, Xanthomonas* species, and other pathogens It is shown herein that secretion of SDEs by a bacterial species inhibit HR. The genomic modifications described herein prevent or minimize inhibition of HR by SDES.

DETAILED DESCRIPTION OF EMBODIMENTS

The disclosure provides a significant improvement over the art due to the lack of agronomically acceptable *Citrus* plants with tolerance or resistance to HLB. HLB is a disease caused by species of the phloem-limited, gram-negative bacteria of genus Ca. *Liberibacter*. In the U.S., the predominant pathogenic species is Ca. *Liberibacter asiaticus* (Las); whereas Ca. *Liberibacter africanus* (Laf) and Ca. *Liberib-*

*acter americanus* (Lam) are the predominant pathogenic species in South Africa and Brazil, respectively. Ca. *Liberibacter* is a vector-transmitted pathogen. The vector organisms are the Asian *Citrus* psyllid, *Diaphorina citri*, and African *Citrus* psyllid, *Trioza erytreae*. HLB was first detected in the United States in August 2005 and has rapidly moved into several *Citrus* producing areas. All commercial *Citrus* plants are susceptible to HLB, and infected *Citrus* plants will irrevocably decline. Plant decline is usually preceded by a decline in the quality of the fruit and fruit drop. Fruit from infected plants are smaller, yield less juice, and have higher acidity, lower sugar and greener peel color than those from uninfected plants.

HLB has resulted in a severe decline in fruit production in Florida, where it has become endemic. However, due to the lack of rapid curative methods that control HLB, prevention of new infections is essential in HLB management. Currently, HLB management consists of preventing trees from becoming infected, which includes protecting young flush from HLB vector organisms and destroying infected plant material.

New infections could be prevented, and the disease could be managed, by planting trees that are tolerant or resistant to the disease. However, utilization of resistant germplasm to slow the spread of HLB is difficult due to the lack of commercially available resistant rootstock/scion combinations. Identification and incorporation of resistance traits from tolerant *Citrus* species and relatives is also a potential disease management strategy, but applying conventional plant breeding methods to *Citrus* plants is difficult and time consuming due to their level of nucellar embryony and long juvenile phases.

Genetically modifying *Citrus* plants is a viable alternative to conventional plant breeding. It is a relatively rapid process and some techniques allow for targeted modification of genetic locus without significant off-target effects. In such cases, genetic modification of existing cultivars has been a key component to combat HLB. In some embodiments, the disclosure employs genetic modification to render the modified *Citrus* plant tolerant to pathogenic Ca. *Liberibacter* species. In specific embodiments, the disclosure provides a *Citrus* plant that is tolerant to Ca. *Liberibacter* effector proteins. As will be understood to those of skill in the art, once a genetic modification conferring resistance to HLB is generated this could readily be introduced into any other cultivar by crossing.

Zebra Chip (ZC) is an economically important disease that occurs in commercial potato fields in the United States, Mexico, Central America, and New Zealand (Munyaneza, J. E. Am. J. Pot Res (2012) 89: 329). ZC was first found in Mexico in 1994 then spread to the United States in 2000 (Rondon, S., Schreiber, A., Hamm, P., Olsen, N., Wenninger, E., Wohleb, C., Waters, T., Cooper, R., Walenta, D., and Reitz, S. 2017. Potato Psyllid Vector of Zebra Chip Disease in the Pacific Northwest. A Pacific Northwest Extension Publication. pp. 1-8.). Similar to Huanglongbing (HLB), ZC and diseases of other solanaceous crops are associated with a fastidious alpha-proteobacterium belonging to the 'Candidatus' genus *Liberibacter*, 'Candidatus *Liberibacter solanacearum*' (CLso), that is transmitted by a phloem-feeding psyllid vector, *Bactericera cockerelli* (Jagoueix, S., et al. 1994, Int. J. Syst. Bacteriol. 44:379-386.; Bove', J. M. 2006, J. Plant Pathol. 88:7-37; Pelz-Stelinski et al. 2010, J. Econ. Entomol. 103:1531-1541). CLso vectored by *B. cockerelli* results in a severe decline of potato, tomato, and pepper production. Current management of CLso consists of chemical controls using insecticides (Rondon et al. 2017). Due to the rapid spread of CLso, new methods to prevent infections are required.

Exemplary Ca. *Liberibacter* effector proteins contemplated by this disclosure are those secreted via the Sec-dependent pathway. Sec-dependent effector (SDE), as used herein, refers to any bacterial effector protein secreted from a bacterium via the Sec-dependent pathway. Pathogenic Ca. *Liberibacter* species secrete SDEs into the phloem of host plants, such as *Citrus* and solanaceous crops. As used herein, the terms "solanaceous crop" or "solanaceous plant" are used interchangeably and are directed plants of the Solanacea family including tomato (*Solanum lycopersicum* and *Solanum pennelli*); potato (*Solanum tuberosum*); eggplant (*Solanum melongena*), bell/chili peppers (*Capsicum annuum, Capsicum baccatum*, and *Capsicum chinense*). These SDEs interact with endogenous proteins and nucleic acids in the phloem and companion cells, disrupting normal physiology and inducing the symptoms of HLB in *Citrus*. Moreover, this same interaction can occur with SDEs related to Ca. *Liberibacter* species (e.g. Ca. *Liberibacter solanacearum*, 'CLso') infection in solanaceous crops such as tomato, pepper eggplant, tamarillo and potato (e.g. zebra chips).

Here we show that one of these secreted proteins, SDE15 also known as Las4025, targets a well-known negative regulator of plant programmed cell death (PCD) to promote infection. Las4025 could be detected in the phloem sap of Las-infected plants. Transgenic expression of Las4025 in *Citrus* promotes Las multiplication and HLB symptom development. SDE15 suppresses not only PCD induced by *Xanthomonas citri* subsp. *citri* (Xcc) in *Citrus*, but also PCD induced by AvrBsT (a PCD-eliciting *Xanthomonas* effector) in tobacco, suggesting that Las4025 is a broad-spectrum bacterial suppressor of plant PCD. Yeast two-hybrid, in vitro protein pull-down and in vivo bimolecular fluorescence complementation assays showed that SDE15 interacts with ACD2 (ACCELERATED CELL DEATH 2), a repressor of plant PCD and that it enhances the red chlorophyll catabolite reductase (RCCR) activity of ACD2 to remove porphyrin-related molecules, accumulation of which causes PCD. Las4025 promotes the chlorophyll break-down in planta and contributes to the development of yellowing symptom associated with HLB. Characterization of Las4025 unravels an elusive aspect of the mechanism of a major plant disease.

In some embodiments, a modified plant no longer expresses endogenous molecules, for example, polypeptides and nucleic acids, capable of interacting with Ca. *Liberibacter* SDEs. In specific embodiments, the SDEs are those secreted by Las. In more specific embodiments, an Las SDE is selected from CLIBASIA_04025 (Las4025), CLIBASIA_00470 (Las470), CLIBASIA_04065 (Las4065), CLIBASIA_05150 (Las5150), and CLIBASIA_04250 (Las4250), which are encoded by the cDNA sequences corresponding to SEQ ID NOs:2-6.

In other embodiments, a modified plant no longer expresses an endogenous molecule, for example, a polypeptide or nucleic acid, and which may be capable of interacting with a Ca. *Liberibacter* Sec-dependent effector (SDE), that is modified. A susceptibility protein or S-protein, as used herein, refers to an endogenous host polypeptide targeted by an SDE. A susceptibility gene or S-gene, as used herein, refers to an endogenous host gene encoding an S-protein. An S-protein-SDE complex, as used herein refers to an S-protein interacting with an SDE. An S-protein-SDE interaction, as used herein refers to a protein-protein interaction between an S-protein and an SDE. In some embodiments, an S-gene is modified such that the encoded S-protein is no longer capable of interacting with an SDE. In other embodiments, an S-gene is modified such that the encoded S-protein may interact with an SDE, but not disrupt normal physiology to an extent that a deleterious mechanism of action is triggered, for a non-limiting example, a modified S-gene that promotes proteasomal degradation of an SDE-S-protein complex before the complex activates a deleterious mechanism of action. In specific embodiments, an S-protein is selected from the group consisting of [accession numbers for *Citrus* provided in parentheses for each S-protein group] PP2-B2/12 (orange1.1t04174), Lectin (orange1.1t05126), Cysteine protease (Cs4g07410), Cysteine protease 15A-like (Cs3g25530), Papain-like cysteine proteases, Myb family transcription factor (orange1.1t02260), YLS9-like (Cs2g29120), Cell death suppressor protein Lls1 (Cs9g02990.1), Acd1-Like Cs9g03000, Acd1 Cs8g15480, accelerated cell death 2 (ACD2) protein (AT4G37000.1, Cs1g22670), red chlorophyll catabolite reductase-like (Cs1g22680), NDR1/HIN1-like protein 13 (Cs8g01640), PHL5-like (Cs7g01290), and PHL5 (orange1.1t02259), for which cDNA examples of the *Citrus* versions are encoded by the cDNA sequences corresponding to SEQ ID NOs:7-29 and SEQ ID NO:31. Potato orthologs are encoded by SEQ ID Nos 39-51. Provided below in Table 1 are accession numbers for select *Citrus* S-protein sequences and S-genes encoding such S-proteins, as well as orthologs in solanaceous plants, that may be modified as taught herein (Cs or orange=gene id (*Citrus* genome database Citrusgenomedb.org); NC or NW=genome sequence (NCBI database); XM=cDNA accession no. (NCBI database); LOC=gene accession no (NCBI database); and XP, NP, PHT or PHU=polypeptide accession no. (NCBI database)):

TABLE 1

| Species | Myb family transcription | Cell death suppressor protein Lls1 | ACD2 | Lectin |
|---|---|---|---|---|
| *Citrus sinensis* | 1. orange1.1t02260<br>LOC102621262<br>XM_025093288<br>XP_024949056<br>NW_006257094.1<br>(602674 . . . 604650)<br>2. XP_024949055<br>3. orange1.1t02259<br>LOC102608693<br>XM_015525401<br>XP_015380887<br>NW_006257094.1<br>(597073 . . . 599506)<br>4. LOC102608059<br>XM_015531655<br>XP_015387141<br>5.XP_015380888.1 | 1. Cs9g02990.1<br>LOC102615553<br>XM_006488849<br>XP_006488912<br>NC_023054.1<br>(1382910 . . . 1386383)<br>2. Cs9g03000<br>XM_006488848<br>LOC102615272<br>XP_006488911<br>NC_023054.1<br>(1390097 . . . 1395026)<br>3. Cs8g15480,<br>XM_006487933<br>XP_006487996<br>NC_023053.1<br>(18675482 . . . 18679902) | 1. Cs1g22680<br>XM_006466545<br>LOC102623285<br>XP_006466608<br>NC_023046.1<br>(25356426 . . . 25358668)<br>2. Cs1g22670<br>NC_023046.1<br>XM_006466544<br>(LOC102622999)<br>XP_006466607<br>NC_023046.1<br>(25352463 . . . 25354069) | 1. orange1.1t05126<br>LOC102630138<br>XM_006495169<br>XP_006495232<br>NW_006257465.1<br>(8465 . . . 9844)<br>2. LOC107177625<br>XM_015531689<br>XP_015387175<br>3. XP_015387176<br>LOC107177626<br>4. XP_015387172<br>LOC107177622<br>6. XP_006475932<br>LOC102628131<br>7. XP_015387174,<br>LOC107177624 |
| *Capsicum annuum* | LOC107843940,<br>XP_016543872,<br>XP_016543873,<br>XP_016576061,<br>PHT77744,<br>XP_016576060,<br>XP_016565589,<br>PHT82561,<br>XP_016565591,<br>XP_016573871,<br>XP_016544890,<br>PHT71362 | PHT80565,<br>XP_016571811,<br>XP_016571812,<br>XP_016571813 | LOC107868112,<br>PHT83236,<br>XP_16570190,<br>NP_001311893,<br>XP_016557361 | PHT71355,<br>PHT71353 |
| *Capsicum baccatum* | PHT37283,<br>PHT44431,<br>PHT52438,<br>PHT48923,<br>PHT33349,<br>PHT60401,<br>PHT39991 | PHT54548,<br>PHT54549,<br>PHT33802,<br>PHT33064,<br>PHT45532 | PHT50387,<br>PHT58680 | PHT37058 |
| *Capsicum chinense* | PHU06047,<br>PHU13451,<br>PHU22243,<br>PHU18686,<br>PHU05798 | PHU16680,<br>PHU16678,<br>PHU16679,<br>PHU03790,<br>PHU02689,<br>PHU01515 | PHU19541 | PHT99312,<br>PHU_05788 |
| *Solanum lycoperiscum* | 1. LOC101251632<br>NC_015447.3<br>(60577349 . . . 60580659 complement) | 1. LOC101255583,<br>NC_015441.3<br>(11974361 . . . 11979604)<br>XP_004237332,<br>AAL32300,<br>NP_001234535 | 1. LOC778267<br>NC_015440.3<br>(9353792 . . . 9357403) | N/a |

TABLE 1-continued

| Solanum pennelli | LOC107032497(XP_015089588), XP_015088029, XP_015088022, XP_015078237, XP_015078236, XP_015076100, XP_015072629, XP_015055275 | XP_015073606, XP_015058211, XP_015072446 | LOC107014711, XP_015070234 | N/a |
|---|---|---|---|---|
| Solanum tuberosum | 1. LOC102578723 NW_006239309.1 (222724 . . . 226103) | 1. LOC102597185 NW_006239415.1 (360276 . . . 368064) 2. LOC102604461 NW_006238942.1 (19429 . . . 23712) | 1. LOC102591737, NW_006239292.1 (123266 . . . 127905 complement) NP_001305541 | N/a |

| Species | Cysteine protease | PP2-B12 | YLS9-like |
|---|---|---|---|
| Citrus sinensis | 1. Cs4g07410 LOC102578016 XM_006474664 NM_001288897 NP_001275826 NC_023049.1 (4697175 . . . 4700328) 2. Cs3g25530 XM_006473521 XP_006473584 LOC102608509 NC_023048.1 (27116634 . . . 27118954) | 1. orange1.1t04174 LOC102626181 XM_025094054 XP_024949822 NW_006257165.1 (68010 . . . 79424) | 1. Cs2g29120 LOC102624273 XM_006470378 XP_006470441 NC_023047.1 (28676278 . . . 28677278) 2. Cs2g29120 LOC107174220 NC_023053.1 (385414 . . . 385806 complement) |
| Capsicum annuum | XP_016580127, XP_016557040, PHT84613. XP_016539529, PHT90352, XP_016561024, PHT70914 | PHT66823, XP_016552209, XP_016552365, PHT66822, XP_016573353, XP_016552297, XP_016573817 | XP_016552935, XP_016561811, XP_016560224, XP_016563876, PHT87859, XP_016562568, PHT62176, PHT71162, XP_016562568 |
| Capsicum baccatum | PHT42963, PHT30454, PHT41774, PHT_57030, PHT_36437, PHT30404, PHT30386, PHT59073 | PHT32781, PHT32780, PHT32035, PHT39101, PHT32776, PHT32782, PHT48962 | PHT59305, PHT54760, PHT27977, PHT53910, PHT29394, PHT43389, PHT36895 |
| Capsicum chinense | PHU11729, PHU20763, PHU10453, PHU27226, PHU05443 | PHU01437, PHU01440, PHU00690, PHU21394, PHU01435, PHU18677, PHT98988, PHU10308 | PHU29409, PHU24981, PHT98447, PHU24513, PHU12324, BAD11071 |
| Solanum lycoperiscum | 1. LOC101252505 NC_015444.3 (54626241 . . . 54628525 complement) | XP_004239687, XP_004253004, XP_004237494, XP_004237583, XP_010314855, XP_004252380 | 1. LOC101250915 NC_015438.3 (3106210 . . . 3109693 complement) |
| Solanum pennelli | XP_015082349, XP_015081027, XP_015074247, XP_015068628, XP_015061093, XP_015058018, XP_015063485, XP_015069437 | XP_015074926, XP_015071726, XP_015059542, XP_015073190, XP_01505954, XP_015084179, XP_015060715 | XP_015084054, XP_015086729, XP_015065001, XP_015067199, XP_015070124, XP_015081836 |
| Solanum tuberosum | 1. LOC102578939 NW_006238961.1 (2218619 . . . 2220963 complement) | XP_006349935, XP_006345814, XP_006340500, XP_006366161, XP_015165222, XP_006344703, XP_006361502, XP_006351708 | 1. LOC102602250 NW_006238997.1 (685210 . . . 686001 complement) |

This disclosure also contemplates embodiments in which a genetic modification anywhere in the genome disrupts expression, and in turn, may disrupt an S-protein-SDE interaction from activating a deleterious mechanism of action. In some embodiments, an S-gene or a regulatory element thereof is modified. In some embodiments, a modification may be made elsewhere in the genome, but ultimately disrupts an S-protein-SDE interaction, for a non-limiting example, inserting genetic material encoding a polypeptide capable of disrupting an S-protein-SDE interaction anywhere in the genome. In specific embodiments, an SDE is secreted the Ca. *Liberibacter* species selected from the group consisting of Las, Laf, and Lam. In some specific embodiments, the SDEs are CLIBASIA_0402 (Las4025), CLIBASIA_00470 (Las470), CLIBASIA_04065 (Las4065), CLIBASIA_05150 (Las5150), and CLIBASIA_04250 (Las4250). In specific embodiments, an S-protein is selected from the group consisting of PP2-B2/12 (orange1.1t04174), Lectin (orange1.1t05126), , Cysteine protease (Cs4g07410), Cysteine protease 15A-like (Cs3g25530), Papain-like cysteine proteases, Myb family transcription factor (orange1.1t02260), YLS9-like (Cs2g29120), , Cell death suppressor protein Lls1 (Cs9g02990.1), Acd1-Like Cs9g03000, Acd1 Cs8g15480, accelerated cell death 2 (ACD2) protein (AT4G37000.1, Cs1g22670), red chlorophyll catabolite reductase-like (Cs1g22680), NDR1/HIN1-like protein 13 (Cs8g01640), PHL5-like (Cs7g01290), and PHL5 (orange1.1t02259).

In some cases, a modification is conducted at a target sequence as set forth in Table 1, or at a target sequence that is at least 95 percent (e.g., at least 96 percent, at least 97 percent, at least 98 percent, or at least 99 percent) identical to the sequence set forth in Table 1. In a more specific example, a modification is conducted at a target sequence set forth in SEQ ID Nos 7-38 or 39-51, or at a target sequence that is at least 95 percent (e.g., at least 96 percent, at least 97 percent, at least 98 percent, or at least 99 percent) identical to a sequence set forth in SEQ ID Nos 7-38 or 39-51.

The percent sequence identity between a particular nucleic acid or amino acid sequence and a sequence referenced by a particular sequence identification number may be determined by techniques known in the art. In one example, sequence identity is determined as follows. First, a nucleic acid or amino acid sequence is compared to the sequence set forth in a particular sequence identification number using the BLAST 2 Sequences (B12seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the B12 seq program can be found in the readme file accompanying BLASTZ. B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seql.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences:\C:\B12seq -i c:\seql.txt -j c:\seq2.txt -p blastn -o c:\output.txt -q -1 -r 2. To compare two amino acid sequences, the options of B12seq are set as follows:\-i is set to a file containing the first amino acid sequence to be compared (e.g., C:\seql.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences:\C:\B12seq -i c:\seq2.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:8), or by an articulated length (e.g., 100 consecutive nucleotides or amino acid residues from a sequence set forth in an identified sequence), followed by multiplying the resulting value by 100. For example, a nucleic acid sequence that has 1200 matches when aligned with the sequence set forth in SEQ ID NO:8 is 83.7 percent identical to the sequence set forth in SEQ ID NO:1 (i.e., 1200±1434×100=83.7). It is noted that the percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. It also is noted that the length value will always be an integer.

The embodiments described herein are not limited to a particular *Citrus* or solanaceous plant or variety but rather encompass any *Citrus* or solanaceous plant or hybrid thereof that may be useful in accordance with the disclosure. *Citrus* varieties contemplated by this disclosure include, but are not limited to, cultivated *Citrus* types such as sweet orange, bitter orange, blood orange, grapefruit, pomelo, citron, clementine, naval orange, lemon, lime, mandarin, tangerine, tangelo, or the like.

I. Genome Editing

Certain aspects of the present disclosure relate to methods of modifying the genome of a *Citrus* or solanaceous plant using genome editing techniques. As used herein, “genome editing” and “genome-engineering” are terms used interchangeably and refer to the modification of a genome through mutagenesis. For example, in plant genome engineering, endonucleases may be used to generate double-strand DNA breaks (DSBs) and activate genome repair pathways. These DSB repair pathways may repair the break cleanly, i.e., without altering the starting sequence, or, alternatively, induce a mutation through an error in repair. In some embodiments, genome editing is used to insert, delete, or substitute one or more base pairs at one or any combination of genetic loci. In some embodiments, a genome editing technique is used to create a mutation, for example, a point mutation or single nucleotide polymorphism.

In some embodiments the DSB repair pathway is non-homologous end-joining (NHEJ) or microhomology mediated end joining (MMEJ). During NHEJ, any nucleotide overhangs on the break ends are either resected or filled to form blunt ends that are ligated. During MMEJ, the break ends are processed to reveal overhangs comprising microhomology sequences that are then ligated together. The insertions or deletions resulting from the terminal end processing in both the NHEJ and MMEJ pathways can be referred to as indels. In some embodiments, the NHEJ or MHEJ that occurs can be relied upon to introduce a genome modification including, but not limited to, a silent mutation, a neutral mutation, a missense mutation, a nonsense mutation, or a frameshift mutation.

In other embodiments, the DSB repair pathway is homologous recombination (HR). During HR, a DSB is repaired using a template with sequences with homology to the DNA flanking the break, i.e., a homologous chromosome. In plant genome editing, a linear DNA polynucleotide flanked by sequences (e.g., of 50 base pairs or more) homologous to those flanking a targeted genomic locus, may be introduced into the genome when a DSB is repaired by HR. In some embodiments, this approach is used to introduce, substitute, or delete a DNA sequence at a genomic locus. Any DNA sequence of interest may be introduced, deleted, or substituted. An introduced or substituted DNA sequence may encode an RNA molecule with a specific activity or function, a DNA molecule with a specific activity or function (e.g., encoding a polypeptide, representing a detectable marker, etc.), a DNA molecule comprising cis-regulatory elements, or a DNA molecule encoding a polypeptide, a motif thereof, or domain thereof. In some embodiments, the nucleic acid encoding the linear DNA sequence that will act as the HR template is encoded by an expression vector. In some embodiments, the nucleic acid encoding the linear DNA sequence of interest is encoded by a DNA sequence separate from the expression vector. For example, and without limitation, the nucleic acid encoding a DNA sequence of interest may be a linear DNA polynucleotide that is co-transformed with an expression vector.

In some embodiments, single-strand breaks or "nicks" are introduced into the target DNA sequence. As used herein, the term "single-strand break inducing agent" or "nickase" refers to any agent that can induce a single-strand break (SSB) in a DNA molecule. In some embodiments two SSBs are introduced into the target DNA to generate a DSB. These breaks may also be repaired by HR, NHEJ, or MMEJ. In some embodiments, sequence modifications occur at or near the SSB sites, which can include deletions or insertions that result in modification of the nucleic acid sequence, or integration of exogenous nucleic acids by HR or NHEJ.

In one aspect, a "modification" comprises the insertion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In another aspect, a "modification" comprises the deletion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In a further aspect, a "modification" comprises the inversion of at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In still another aspect, a "modification" comprises the substitution of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In some embodiments, a "modification" comprises the substitution of an "A" for a "C," "G" or "T" in a nucleic acid sequence. In some embodiments, a "modification" comprises the substitution of an "C" for an "A," "G" or "T" in a nucleic acid sequence. In some embodiments, a "modification" comprises the substitution of a "G" for an "A," "C" or "T" in a nucleic acid sequence. In some embodiments, a "modification" comprises the substitution of a "T" for an "A," "C" or "G" in a nucleic acid sequence. In some embodiments, a "modification" comprises the substitution of a "C" for an "U" in a nucleic acid sequence. In some embodiments, a "modification" comprises the substitution of a "G" for an "A" in a nucleic acid sequence. In some embodiments, a "modification" comprises the substitution of an "A" for a "G" in a nucleic acid sequence. In some embodiments, a "modification" comprises the substitution of a "T" for a "C" in a nucleic acid sequence.

In some embodiments, genome editing of a *Citrus* plant as described herein may encompass techniques that employ methods of targeting endonucleases to one or more genetic loci. In some embodiments, synthetic polypeptides, for example, Transcription Activator-Like Effectors (TALEs) and zinc fingers (ZFs), or nucleic acids, for example, Clustered Regularly Interspaced Short Palindromic Repeats/Cas (CRISPR/CAS) single guide RNAs or NgAgo (Argonaute) single strand DNAs, are used to target endonucleases to any genomic locus. The targeted endonucleases may catalyze a DSB at a target locus. Upon detecting these breaks, a cell may initiate any DSB repair pathway. In some embodiments, genome editing is carried out at more than one genomic locus simultaneously (i.e., multiplex genome engineering). In some embodiments, multiplex genome engineering may be used to remove a sequence of any size from the genome. In some embodiments, any combination and number of endonuclease targeting techniques may be used to target one or more genetic loci.

A. RNA- and DNA-Guided Genome Editing Systems

In some embodiments, genome engineering of a *Citrus* plant as described herein may employ RNA-guided endonucleases including, but not limited to CRISPR/Cas systems. CRISPR/Cas systems have been described in U.S. Patent Application Publication Nos. 2017/0191082 and 2017/0106025, each of which are incorporated herein by reference in their entirety. In some embodiments, a targeted genome modification as described herein comprises the use of at least one, at least two, at least three, at least four, at least five, at least six, at least seven, at least eight, at least nine, or at least ten RNA-guided nucleases. In some embodiments, a CRISPR/Cas9 system, a CRISPR/Cpf1 system, a CRISPR/CasX system, or a CRISPR/CasY system are alternatives that may be used to generate modifications to target sequences as described herein.

The CRISPR systems are based on RNA-guided endonucleases that use complementary base pairing to recognize DNA sequences at target sites. CRISPR/Cas systems are part of the adaptive immune system of bacteria and archaea, protecting them against invading DNA, such as viral DNA, by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA.

A prerequisite for cleavage is the presence of a conserved protospacer-adjacent motif (PAM) downstream of the target DNA, which usually has the sequence 5'-NGG-3' but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA. Specificity of the CRISPR/Cas system is based on an RNA-guide that use complementary base pairing to recognize target DNA sequences. In some embodiments, the site-specific genome modification enzyme is a CRISPR/Cas system. In an aspect, a site-specific genome modification enzyme provided herein can comprise any RNA-guided Cas endonuclease (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof); and, optionally, the guide RNA necessary for targeting the respective nucleases.

In some embodiments, an RNA-guided endonuclease is the DNA cleavage domain of a restriction enzyme fused to a deactivated Cas9 (dCas9), for example dCas9-Fok1. As used herein, a "dCas9" refers to a endonuclease protein with one or more amino acid mutations that result in a Cas9 protein without endonuclease activity, but retaining RNA-guided site-specific DNA binding. As used herein, a "dCas9-restriction enzyme fusion protein" is a dCas9 with a protein fused to the dCas9 in such a manner that the restriction enzyme is catalytically active on the DNA.

In some embodiments, genome editing of a *Citrus* or solanaceous plant as described herein may employ DNA-guided endonucleases including, but not limited to, NgAgo systems.

In one aspect, a method and/or composition provided herein comprises one or more, two or more, three or more, four or more, or five or more guide RNAs or DNAs. In another aspect, a CRISPR/CAS system, dCas9-restriction enzyme fusion protein, NgAgo system provided herein is capable of generating a targeted DSB in a target sequence as described herein. In one aspect, vectors comprising nucleic acids encoding one or more, two or more, three or more, four or more, or five or more guide RNAs or DNAs and the corresponding CRISPR/CAS system, dCas9-restriction enzyme fusion protein, NgAgo system are provided to a cell by transformation methods known in the art (e.g., without being limiting, viral transfection, particle bombardment, PEG-mediated protoplast transfection or *Agrobacterium*-mediated transformation).

B. Transcription Activator-Like Effector Nucleases

In some embodiments, genome editing of a *Citrus* plant as described herein may employ Transcription Activator-Like Effector Nucleases (TALENs). TALENs have been described in U.S. Patent Application Publication Nos. 2016/0369301 and 2015/0203871 (both of which are incorporated herein by reference in their entirety) and are well known in the art. TALENs are artificial restriction enzymes generated by fusing the transcription activator-like effector (TALE) DNA binding domain to an endonuclease domain. In one aspect, the nuclease is selected from a group consisting of PvuII, MutH, TevI and FokI, AwI, MlyI, SbfI, SdaI, StsI, CleDORF, Clo051, Pept071. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

TALEs can be engineered to bind practically any DNA sequence, such as a target sequence as described herein. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

In one aspect, a method and/or composition provided herein comprises one or more, two or more, three or more, four or more, or five or more TALENs. In another aspect, a TALEN provided herein is capable of generating a targeted DSB in a target sequence as described herein. In one aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation).

C. Zinc Finger Nucleases

In some embodiments, genome engineering of a *Citrus* or solanaceous plant as described herein may employ Zinc Finger Nucleases (ZFNs). ZFNs have been described in U.S. Pat. No. 9,322,006 (incorporated herein by reference in its entirety) and are well known in the art. ZFNs are synthetic proteins consisting of an engineered zinc finger DNA-binding domain fused to the cleavage domain of an endonuclease, for example, Fok1. ZFNs can be designed to cleave almost any long stretch of double-stranded DNA by the modification of the zinc finger DNA-binding domain. ZFNs form dimers from monomers composed of a non-specific DNA cleavage domain of FokI nuclease fused to a zinc finger array engineered to bind a target DNA sequence. The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art. The FokI nuclease domain requires dimerization to cleave DNA and therefore two ZFNs with their C-terminal regions are needed to bind opposite DNA strands of the cleavage site (separated by 5-7 nt). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

Several embodiments relate to a method and/or composition provided herein comprising one or more, two or more, three or more, four or more, or five or more ZFNs directed to a target sequence as described herein. In another aspect, a ZFN provided herein is capable of generating a targeted DSB. In one aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or *Agrobacterium*-mediated transformation).

D. Meganucleases

In some embodiments, genome engineering of a *Citrus* or solanaceous plant as described herein may employ a meganuclease. Meganucleases, which are commonly identified in microbes, are unique enzymes with high activity and long recognition sequences (>14 nt) resulting in site-specific digestion of target DNA. Engineered versions of naturally occurring meganucleases typically have extended DNA recognition sequences (for example, 14 to 40 nt). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

In one aspect, a method and/or composition provided herein comprises one or more, two or more, three or more, four or more, or five or more meganucleases directed to a target sequence as described herein. In some embodiments, a meganuclease provided herein is capable of generating a targeted DSB. In some embodiments, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

II. Site-Specific Genome Modification

Certain aspects of the present disclosure relate to methods of modifying the genome of a *Citrus* plant using site-specific genome modification techniques. In some embodiments, site-specific genome modification of a *Citrus* plant as described herein may employ any site-specific genome modification enzyme. As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme is a recombinase. In some embodiments, a site-specific genome modification enzyme is a transposase. In the present disclosure, site-specific genome modification enzymes include, but are not limited to, nucleases, endonucleases, recombinases, invertases, transposases, methytransferase, demethlylases, aminases, deaminases, helicases, and any combination thereof.

In some embodiments, the site-specific genome modification enzyme is a recombinase. Non-limiting examples of recombinases include a tyrosine and serine recombinases and coupled with a DNA recognition motifs, for example, a Cre recombinase, a Gin recombinase, a Flp recombinase, and a Tnp1 recombinase. In another aspect, a serine recombinase coupled with a DNA recognition motif, for example, a PhiC31 integrase, an R4 integrase, and a TP-901 integrase. In an aspect, a recombinase is tethered to a zinc-finger DNA-binding domain, or a TALE DNA-binding domain, or a Cas9 nuclease.

The Flp-FRT site-directed recombination system comes from the 2p plasmid from the baker's yeast *Saccharomyces cerevisiae*. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites.

Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

In another aspect, the site-specific genome modification enzyme is a dCas9-recombinase fusion protein. As used herein, a "dCas9-recombinase fusion protein" is a dCas9 with a protein fused to the dCas9 in such a manner that the recombinase is catalytically active on the DNA. In some embodiments, dCas9 may be fused with the catalytic domain of any enzyme such that the catalytic domain is catalytically active on DNA. In another aspect, a DNA transposase is attached to a DNA binding domain for example, a TALE-piggyBac and TALE-Mutator.

Several embodiments relate to promoting DNA recombination by providing a site-specific genome modification enzyme to a plant cell. In some embodiments, recombination is promoted by providing a strand separation inducing reagent. In one aspect, the site-specific genome modification enzyme is selected from an endonuclease, a recombinase, an invertase, a transposase, a helicase or any combination thereof. In some embodiments, recombination occurs between B chromosomes. In some embodiments, recombination occurs between a B chromosome and an A chromosome.

Several embodiments relate to promoting integration of one or more DNAs of interest by providing a site-specific genome modification enzyme. In some embodiments, integration of one or more DNAs of interest is promoted by providing a strand separation inducing reagent. In one aspect, the site-specific genome modification enzyme is selected from an endonuclease, a recombinase, a transposase, a helicase or any combination thereof. Any DNA sequence can be integrated into a target site of a chromosome sequence by introducing the DNA sequence and the provided site-specific genome modification enzymes. Any method provided herein can utilize any site-specific genome modification enzyme provided herein.

Several embodiments relate to a method and/or a composition provided herein comprising at least one, at least two, at least three, at least four, at least five, at least six, at least seven, at least eight, at least nine, or at least ten site-specific genome modification enzymes. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific genome modification enzymes.

III. Plant Transformation Constructs

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. In some embodiments, a viral vector based on a plant virus such as a *Citrus* Tristeza Virus may be used in accordance with the disclosure. It is contemplated that utilization of cloning systems with large insert capacities will allow introduction of large genetic sequences comprising more than one selected gene. In accordance with the disclosure, this could be used to introduce genetic material corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes that have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant genetically modified cells resulting in a screenable or selectable trait and/or will impart an improved phenotype to the resulting genetically modified plant. However, this may not always be the case, and the present disclosure also encompasses genetically modified plants incorporating non-expressed transgenes.

In accordance with the disclosure, a nucleic acid vector comprising a coding sequence may be introduced into a plant such as a *Citrus* tree or variety, such that, when the vector is transformed into a *Citrus* variety or plant as described herein, the coding sequence is expressed in the plant. In some embodiments the coding sequence may be expressed in, for example, the phloem or roots of the plant, or any other part of the plant. Expression of the coding sequence in the resulting genetically modified *Citrus* tree or variety results in the tree exhibiting increased tolerance or resistance to HLB when compared to a tree lacking expression of the coding sequence.

A. Proteins and Recombinant DNA Molecules

As used herein, a "protein/Coding DNA molecule" or "polypeptide/Coding DNA molecule" refers to a DNA molecule comprising a nucleotide sequence that encodes a protein or polypeptide. A "coding sequence" or "protein/Coding sequence" or "polypeptide/Coding sequence" means a DNA sequence that encodes a protein or polypeptide. A "sequence" means a sequential arrangement of nucleotides or amino acids. The boundaries of a protein/Coding sequence or polypeptide/Coding sequence are usually determined by a translation start codon at the 5'-terminus and a translation stop codon at the 3'-terminus. A protein/Coding molecule or polypeptide/Coding molecule may comprise a DNA sequence encoding a protein or polypeptide sequence. As used herein, "transgene expression," "expressing a transgene," "protein expression," "polypeptide expression," "expressing a protein," and "expressing a polypeptide" mean the production of a protein or polypeptide through the process of transcribing a DNA molecule into messenger RNA (mRNA) and translating the mRNA into polypeptide chains, which may be ultimately folded into proteins. A protein/Coding DNA molecule or polypeptide/Coding DNA molecule may be operably linked to a heterologous promoter in a DNA construct for use in expressing the protein or polypeptide in a cell transformed with the recombinant DNA molecule. As used herein, "operably linked" means two DNA molecules linked in manner so that one may affect the function of the other. Operably-linked DNA molecules may be part of a single contiguous molecule and may or may not be adjacent. For example, a promoter is operably linked with a protein/Coding DNA molecule or polypeptide/Coding DNA molecule in a DNA construct where the two DNA molecules are so arranged that the promoter may affect the expression of the transgene.

As used herein, a "DNA construct" is a recombinant DNA molecule comprising two or more heterologous DNA sequences. DNA constructs are useful for transgene expression and may be comprised in vectors and plasmids. DNA constructs may be used in vectors for the purpose of genome modification, that is the introduction of heterologous DNA into a host cell, in order to produce genetically modified plants and cells, and as such may also be contained in the plastid DNA or genomic DNA of a genetically modified plant, seed, cell, or plant part. As used herein, a "vector" means any recombinant DNA molecule that may be used for the purpose of genetically modifying a plant or plant cell. Recombinant DNA molecules as set forth in the sequence listing, can, for example, be inserted into a vector as part of a construct having the recombinant DNA molecule operably linked to a promoter that functions in a plant to drive expression of the protein encoded by the recombinant DNA molecule. Methods for constructing DNA constructs and vectors are well known in the art. The components for a DNA construct, or a vector comprising a DNA construct, generally include, but are not limited to, one or more of the following: a suitable promoter for the expression of an operably linked DNA, an operably linked protein/Coding DNA molecule, and a 3' untranslated region (3'-UTR). Promoters useful in practicing the present disclosure include those that function in a plant for expression of an operably linked polynucleotide. Such promoters are varied and well known in the art and include those that are inducible, viral, synthetic, constitutive, temporally regulated, spatially regulated, and/or spatio-temporally regulated. Additional optional components include, but are not limited to, one or more of the following elements: 5'-UTR, enhancer, leader, cis-acting element, intron, chloroplast transit peptides (CTP), and one or more selectable marker transgenes.

Recombinant DNA molecules of the present disclosure may be synthesized and modified by methods known in the art, either completely or in part, especially where it is desirable to provide sequences useful for DNA manipulation (such as restriction enzyme recognition sites or recombination-based cloning sites), plant-preferred sequences (such as plant/Codon usage or Kozak consensus sequences), or sequences useful for DNA construct design (such as spacer or linker sequences). The present disclosure includes recombinant DNA molecules and proteins having at least about 80% (percent) sequence identity, about 81% sequence identity, about 82% sequence identity, about 83% sequence identity, about 84% sequence identity, about 85% sequence identity, about 86% sequence identity, about 87% sequence identity, about 88% sequence identity, about 89% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, about 99% sequence identity, or about 100% sequence identity to a coding sequence provided herein, for instance the sequences set forth as SEQ ID NOs: 2-9-11-51. As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, CA), MEGAlign (DNAStar, Inc., Madison, WI), and MUSCLE (version 3.6) (Edgar, Nucl. Acids Res. 32:1792-1797, 2004) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

Proteins in accordance with the disclosure may be produced by changing (that is, modifying) a wild-type protein to produce a new protein with a novel combination of useful protein characteristics, such as altered Vmax, Km, substrate specificity, substrate selectivity, and protein stability. Modifications may be made at specific amino acid positions in a protein and may be a substitution of the amino acid found at that position in nature (that is, in the wild-type protein) with a different amino acid. Proteins provided by the disclosure thus provide a new protein with one or more altered protein characteristics relative to the wild-type protein found in nature. In one embodiment of the disclosure, a protein may have altered protein characteristics such as improved or decreased activity against one or more herbicides or improved protein stability as compared to a similar wild-type protein, or any combination of such characteristics. In one embodiment, the disclosure provides a protein, and the DNA molecule or coding sequence encoding it, having at least about 80% sequence identity, about 81% sequence identity, about 82% sequence identity, about 83% sequence identity, about 84% sequence identity, about 85% sequence identity, about 86% sequence identity, about 87% sequence identity, about 88% sequence identity, about 89% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, about 99% sequence identity, or about 100% sequence identity to a protein sequence such as set forth as SEQ ID NOs: 2-9 and SEQ ID NO:11-51. Amino acid mutations may be made as a single amino acid substitution in the protein or in combination with one or more other mutation(s), such as one or more other amino acid substitution(s), deletions, or additions. Mutations may be made as described herein or by any other method known to those of skill in the art.

B. Regulatory Elements

The plants and methods of the present disclosure can utilize a vector comprising a coding sequence that, when the vector is transfected into a plant, the coding sequence is expressed in the plant. The site and conditions under which the first selected DNA is expressed can be controlled to a great extent by selecting a promoter element in the vector that causes expression under the desired conditions.

In some embodiments, the coding sequence is expressed primarily in the roots of the plant, or in the phloem tissue of the plant. In this case, the coding sequence may be expressed in a greater quantity in roots or phloem than in other tissues of the plant. In some embodiments, more than one copy of an coding sequence may be expressed in a plant such that expression in the roots or phloem may be at least twice as much as in any other individual plant tissue (e.g., leaves, flowers, etc.).

Limiting expression of the coding sequence primarily to the roots or phloem of a plant may be accomplished by operably linking the coding sequence to a heterologous promoter active in plant tissues, such as a root-specific or phloem-specific promoter. In other embodiments, a constitutive promoter may be preferred such that the coding sequence is expressed in all tissues of the plant. In some embodiments, a phloem-specific promoter in accordance with the disclosure may comprise an *Arabidopsis* sucrose-proton symporter 2 (AtSUC2) promoter, or a constitutive promoter may comprise a CaMV 35S promoter. Any root-specific or phloem-specific promoter known in the art may potentially be utilized to direct expression of the coding sequence to the roots or the phloem tissue. Examples of these may include, but are not limited to, an RB7, RPE15, RPE14, RPE19, RPE29, RPE60, RPE2, RPE39, RPE61, SHR, ELG3, EXP7, EXP18 or Atlg73160 promoter (Vijaybhaskar et al., 2008; Kurata et al., 2005; PCT Publication WO 01/53502; U.S. Pat. No. 5,459,252; Cho and Cosgrove, 2002).

In some embodiments, a coding sequence as described herein may be expressed at any level in the plant such that it may be detected in the plant using techniques known in the art. A coding sequence may be expressed in a greater quantity in a genetically modified *Citrus* plant or variety than in a plant not expressing the coding sequence as described herein. In some embodiments, the coding sequence is expressed at least twice as much as in a plant not expressing a coding sequence. In further embodiments, the coding sequence is expressed at least three, or four, or five times, or more, as much as in a plant not expressing a coding sequence. In yet another embodiment, there is no detectable expression of the coding sequence in a plant not expressing a coding sequence.

The DNA sequence between the transcription initiation site and the start of the coding sequence, i.e., the untranslated leader sequence, can also influence gene expression. One may thus wish to employ a particular leader sequence with a transformation construct of the disclosure. Useful leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure.

It is contemplated that vectors for use in accordance with the present disclosure may be constructed to include an ocs enhancer element. This element was first identified as a 16-bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

C. Terminators

Transformation constructs prepared in accordance with the disclosure will typically include a 3' end DNA sequence that acts as a signal to terminate transcription and allow for the poly-adenylation of the mRNA produced by coding sequences operably linked to a promoter. In one embodiment of the disclosure, the native terminator of a coding sequence coding sequence may be used. Alternatively, a heterologous 3' end may enhance the expression of coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

D. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a genetically modified plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

E. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Many examples of suitable marker proteins are known to the art and can be employed in the practice of the disclosure. Examples include, but not limited to, neo (Potrykus et al., 1985), bar (Hinchee et al., 1988), bxn (Stalker et al., 1988); a mutant acetolactate synthase (ALS) (European Patent Application 154, 204, 1985) a methotrexate resistant DHFR (Thillet et al., 1988), β-glucuronidase (GUS); R-locus (Dellaporta et al., 1988), β-lactamase (Sutcliffe, 1978), xylE (Zukowsky et al., 1983), α-amylase (Ikuta et al., 1990), tyrosinase (Katz et al., 1983), β-galactosidase, luciferase (lux) (Ow et al., 1986), aequorin (Prasher et al., 1985), and green fluorescent protein (Sheen et al., 1995; Haseloff et al., 1997; Reichel et al., 1996; Tian et al., 1997; WO 97/41228).

Included within the terms "selectable" or "screenable" markers also are genes which encode a "secretable marker" whose secretion can be detected as a means of identifying or selecting for genetically modified cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., (α-amylase, β-lactamase, phosphinothricin acetyltransferase); and proteins that are inserted or trapped in the cell wall (e.g., proteins that include a leader sequence such as that found in the expression unit of extensin or tobacco PR-S).

IV. Antisense and RNAi Constructs

In the methods and compositions of the present disclosure, endogenous gene activity can be down-regulated by any means known in the art, including through the use of ribozymes or aptamers. Endogenous gene activity can also be down-regulated with an antisense or RNAi molecule.

In particular, constructs comprising a coding sequence, including fragments thereof, in antisense orientation, or combinations of sense and antisense orientation, may be used to decrease or effectively eliminate the expression of the gene in a plant such as a *Citrus* tree or variety. Accordingly, this may be used to "knock-out" the function of the coding sequence or homologous sequences thereof.

Techniques for RNAi are well known in the art and are described in, for example, Lehner et al., (2004) and Downward (2004). The technique is based on the ability of double stranded RNA to direct the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson/Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the disclosure, such an oligonucleotide may comprise any unique portion of a nucleic acid sequence provided herein. In certain embodiments of the disclosure, such a sequence comprises at least 18, 30, 50, 75, or 100 or more contiguous nucleic acids of the nucleic acid sequence of a gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that an embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., as in a ribozyme) could be designed. Methods for selection and design of sequences that generate RNAi are well known in the art (e.g. Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

V. Methods for Genetic Transformation

Suitable methods for transformation of plant or other cells for use with the current disclosure are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into genetically modified plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Another method for delivering transforming DNA segments to plant cells in accordance with the disclosure is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force.

VI. Production and Characterization of Genetically Modified Plants

After effecting delivery of exogenous DNA to recipient cells, the next steps generally concern first identifying and selecting the transformed cells and from those cells identifying the selecting the genetically modified cells for further culturing and plant regeneration. In order to improve the ability to identify transformed and genetically modified cells, one may desire to employ one or more selectable or screenable marker genes with a transformation vector prepared in accordance with the disclosure. In this case, one would then generally assay the potentially transformed and modified cell population by exposing the cells to a selective agent or agents, or one would screen the cells for the desired marker gene trait.

It is believed that DNA is introduced into only a small percentage of target cells in any one study. In order to provide an efficient system for identification of those cells that are transformed and predisposed to genetic modification one may employ a means for selecting those cells that are stably transformed. One exemplary embodiment of such a method is to introduce, into the host cell, a marker gene which confers resistance to some normally inhibitory agent, such as an antibiotic or herbicide. Potentially transformed cells then are exposed to the selective agent. In the population of surviving cells will be those cells where, generally, the resistance/Conferring gene has been integrated and expressed at sufficient levels to permit cell survival. Cells may be tested further to confirm stable integration of the exogenous DNA.

Cells that survive the exposure to the selective agent, or cells that have been scored positive in a screening assay, may then be selected again using a second, distinct selection paradigm that detects those cells that contain the genetic modification. Cells that survive the exposure to the second selective agent, or cells that have been scored positive in the second screening assay, may be cultured in media that supports regeneration of plants. The genetically modified cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a genetically modified cell is identified, depending on the initial tissue.

To confirm the presence of the genetic modification in the regenerating plants, a variety of assays may be performed. Such assays include, for example, "molecular biological" assays, such as Southern and northern blotting and polymerase chain reaction (PCR); "biochemical" assays, such as detecting the absence or presence of a protein product, e.g., by immunological means (ELISAs and western blots) or by enzymatic function; plant part assays, such as leaf or root assays; and also, by analyzing the phenotype of the whole regenerated plant. Modification of the host genome and the independent identities of genetically modified plants may be determined using, e.g., Southern hybridization or PCR. Genetic modifications that affect, for example, protein or gene expression may then be evaluated by specifically measuring the expression of those affected molecules or evaluating the phenotypic changes brought about by their expression change.

VII. Breeding Plants of the Disclosure

In addition to direct transformation of a particular plant genotype with a construct prepared according to the current disclosure, genetically modified plants may be made by crossing a plant having a selected genetic modification of the disclosure to a second plant lacking the construct. For example, a selected lignin biosynthesis coding sequence can be introduced into a particular plant variety by crossing, without the need for ever directly transforming a plant of that given variety. Therefore, the current disclosure not only encompasses a plant directly modified or regenerated from cells which have been modified in accordance with the current disclosure, but also the progeny of such plants.

As used herein the term "progeny" denotes the offspring of any generation of a parent plant prepared in accordance with the instant disclosure, wherein the progeny comprises a selected DNA construct. "Crossing" a plant to provide a plant line having one or more added transgenes relative to a starting plant line, as disclosed herein, is defined as the techniques that result in a coding sequence of the disclosure being introduced into a plant line by crossing a starting line with a donor plant line that comprises a first selected DNA of the disclosure. To achieve this in a plant such as a *Citrus* tree one could, for example, perform the following steps:

(a) plant seeds of the first (starting line) and second (donor plant line that comprises a first selected DNA of the disclosure) parent plants;
(b) grow the seeds of the first and second parent plants into plants that bear flowers;
(c) pollinate a flower from the first parent plant with pollen from the second parent plant; and
(d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;
(b) selecting one or more progeny plant containing the desired gene, DNA sequence or element;
(c) crossing the progeny plant to a plant of the second genotype; and
(d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

In some embodiments, asexual reproduction or propagation may be used to obtain a progeny plant in accordance with the disclosure. Techniques to achieve asexual propagation or reproduction in *Citrus* trees or varieties may include, for example, grafting, budding, top-working, layering, runner division, cuttings, rooting, T-budding, and the like. In some embodiments, one *Citrus* variety into which a coding sequence has been introduced may be grafted onto the rootstock of another variety. In other embodiments, a coding sequence may be introduced into the rootstock. In either of these situations, one or both of the plant varieties may exhibit increased tolerance or resistance to HLB.

EXAMPLES

Example 1

Identification of Las SDEs

Las has been predicted to produce at least 166 SDEs, 36 of which have been shown to be highly expressed in plants. These 36 Las SDEs were stably or transiently expressed in Citrus plants and Nicotiana benthamiana to determine if they are HLB effectors. Transgenic expression of CLIBASIA_04025 (Las4025), CLIBASIA_00470 (Las470), CLIBASIA_04065 (Las4065), CLIBASIA_05150 (Las5150), and CLIBASIA_04250 (Las4250) induced symptoms consistent with HLB. For example, transgenic expression of CLIBASIA_04025 (Las4025) without its signal peptide stunted leaf growth, delayed plant growth, and induced leaf yellowing (FIG. 1A and FIG. 1B). The CLIBASIA_04025 expression in transgenic lines was confirmed using an antibody against CLIBASIA_04025 (FIG. 1C). Transgenic expression of CLIBASIA_00470 also delayed plant growth.

Example 2

Las SDE and Host Target Proteins Interaction Assays

Yeast two-hybrid (Y2H) screening was performed to identify putative target proteins of the SDEs identified above. A cDNA library was generated from mRNA isolated from 'Valencia' sweet orange plants infected with Las. The mRNA was obtained from these plants during the early stage of infection in which the Las Ct value was between 28-30. The cDNA library was constructed using the Make Your Own Mate & Plate™ Library System (Clontech) following the manufacturer's instructions and had a titer greater than $3 \times 10^8$ cfu.

The coding sequences of CLIBASIA_04025 (Las4025), CLIBASIA_00470 (Las470), CLIBASIA_04065 (Las4065), CLIBASIA_05150 (Las5150), and CLIBASIA_04250 (Las4250), without their signal peptides, were cloned in-frame with the GAL4 DNA-binding domain (BD) of the bait vector pGBKT7. The Y2H screen was performed using the Matchmaker® Gold Yeast Two-Hybrid System (Clontech) following the manufacturer's instructions. The SDE target proteins identified in the screen are summarized in Table 1B.

TABLE 1B

Y2H-confirmed Las SDE target proteins.

| SDEs | Target proteins |
|---|---|
| CLIBASIA_04025 (Las4025) | PP2-B2/12 (orange1.1t04174) |
| | Lectin (orange1.1t05126) |
| | Cysteine protease (Cs4g07410) |
| | Cysteine protease 15A-like (Cs3g25530) |
| | Myb family transcription factor (orange1.1t02260) |
| | YLS9-like (Cs2g29120) |
| | Cell death suppressor protein Lls1(Cs9g02990) |
| | Red chlorophyll catabolite reductase; Accelerated cell death 2 (Cs1g22670) |
| | Homolog to Acd2, red chlorophyll catabolite reductase-like (Cs1g22680), which is 64% similar |
| | Homolog to Lls1 - Acd1-Like Cs9g03000, which is 93.4% similar; Acd1 Cs8g15480, which is 51% similar, but is also work in same chlorophyll catabolism pathway to Acd2. |
| | Homologs to Cysteine protease (Cs3g25530) and Cysteine Protease (Cs4g07410), all Papain-like cysteine proteases |
| | Homolog YLS9-like, NDR1/HIN1-like protein 13, Cs8g01640, which is 75% similar |
| | Homologs to Myb family transcription factor, PHL5-like, Cs7g01290, 56% similar; PHL5, orange1.1t02259, which is 76% similar |
| | Galactinol-sucrose galactosyltransferase 2 (Cs9g12460) |
| | Vacuolar protein sorting-associated protein 36 (Cs7g24050) |
| | DnaJ protein homolog (Cs7g23510) |
| | Plastid-specific ribosomal protein 4 (Cs6g08000) |
| | Pathogenesis-related protein 10 (Cs9g03630) |
| | Glucan endo-1,3-beta-D-glucosidase-like protein (orange1.1t00643) |
| | Core-2/I-branching beta-1,6-N-acetylglucosaminyltransferase family protein (Cs7g07430) |
| | Leucyl-tRNA synthetase bacterial/mitochondrial, class Ia (Cs2g02720) |
| | Annexin D1 (Cs3g18360) |
| | Pentatricopeptide repeat-containing protein (Cs5g26120) |
| | Probable fructose-bisphosphate aldolase 2, chloroplastic (Cs8g08710) |
| | Arginine/serine-rich splicing factor, putative, expressed (Cs3g18350) |
| | SVP1-like protein 2 (Cs5g32770) |
| | Alanine aminotransferase 2 (Cs7g09270) |
| | BEL1-like homeodomain protein 1 (Cs6g13660) |
| | AT-rich interactive domain-containing protein 4 (Cs4g06750) |
| | Heat shock factor protein HSF8 (Cs7g24140) |
| | Plasma membrane ATPase 1 (Cs6g03480) |
| | Gag-pol polyprotein (Cs7g14770) |
| | Phospholipid: diacylglycerol acyltransferase (Cs1g17750) |
| | Aconitate hydratase, cytoplasmic (Cs2g21430) |
| | DNA-directed RNA polymerase subunit alpha (orange1.1t03665) |
| | Polyubiquitin 10 (Cs4g11190) |

TABLE 1B-continued

Y2H-confirmed Las SDE target proteins.

| SDEs | Target proteins |
|---|---|
| | Diacylglycerol kinase theta (Cs4g02800) |
| | Chloroplast methionine sulfoxide reductase B2 (Cs9g05400) |
| | Leucine-rich repeat receptor protein kinase EXS (Cs7g18050) |
| | Lateral organ boundaries-domain 29 (orange1.1t00246.1) |
| | Formamidase (Cs1g21820) |
| | Signal peptidase complex subunit 3B (Cs3g13460) |
| | Probable plastid-lipid-associated protein 8 (Cs7g07440) |
| | Stress responsive gene 6 protein (orange1.1t01091) |
| | UBX domain-containing protein (Cs5g01690) |
| | Protein SRG1 (Cs5g13180) |
| | Thioredoxin H-type (Cs1g24740) |
| | Glycoside hydrolase (Cs8g12020) |
| | Thioredoxin F2 (Cs6g02830) |
| | RNA pseudourine synthase 7 (orange1.1t02625) |
| | Kunitz-type protease inhibitor KPI-D2.2 (Cs5g16850) |
| | Aspartate aminotransferase (Cs4g19830) |
| | UDP-glucuronate decarboxylase 4 (Cs6g05450) |
| | Nitrate transporter 1.5 (orange1.1t00223) |
| | FKBP-like peptidyl-prolyl cis-trans isomerase family protein (orange1.1t00062) |
| | Zinc-binding alcohol dehydrogenase domain-containing protein 2 (Cs8g05790) |
| | Mannitol dehydrogenase (Cs1g20600) |
| | RNA recognition motif family protein (Cs2g07940) |
| | alpha/beta-Hydrolases superfamily protein (Cs2g21120) |
| | Protein argonaute 1 (Cs5g16710) |
| | Progesterone 5-beta-reductase (Cs3g11840) |
| | NADH dehydrogenase [ubiquinone] 1 alpha subcomplex subunit 6 (Cs1g16240) |
| | Tetratricopeptide repeat (TPR)-like superfamily protein (Cs6g03690) |
| | Mitochondrial carrier domain-containing protein (Cs6g03800) |
| | Cell division control protein 48 homolog C (Cs3g01650) |
| | Subtilisin-like protease (Cs8g02780) |
| | U6 snRNA-associated Sm-like protein LSm6 (orange1.1t02120) |
| | Subtilisin-like protease (Cs8g06090) |
| | Histone H4 (Cs8g18120) |
| | Chromatin-associated protein Dek (Cs4g08790) |
| | Serine carboxypeptidase-like 49 (Cs7g24460) |
| | RING/U-box superfamily protein (Cs8g16720) |
| | Linoleate 13S-lipoxygenase 2-1 (orange1.1t04376) |
| | Isoflavone reductase-like (Cs2g16260) |
| | alpha-like protein (Cs6g16290.1) |
| | THO complex subunit 3 (Cs7g18110) |
| | Uncharacterized protein Sb07g024435 (Cs7g26460) |
| | Ubiquitin-activating enzyme E1 2 (Cs8g20660) |
| | Structure-specific endonuclease subunit SLX1 (Cs2g09350) |
| | Putative uncharacterized protein P0458H05.117 (Cs4g05300) |
| | Aconitate hydratase 1 (Cs1g26040) |
| | DnaJ homolog subfamily B member 13 (Cs3g04780) |
| | Plastocyanin (Cs3g26730) |
| | Putative uncharacterized protein Sb03g000880 (Cs5g31880) |
| | 50S ribosomal protein L14 (orange1.1t04817) |
| | Oligopeptidase A (Cs1g20720) |
| | Maturase K (Cs2g09070) |
| | Protein FRA10AC1 (Cs7g01730) |
| | Putative Uncharacterized protein AlNc14C124G6763 (Cs8g09030) |
| | Putative Uncharacterized protein Sb10g020525 (orange1.1t00482) |
| | Putative Uncharacterized protein OSJNBb0021O11.27 (Cs4g16820) |
| CLIBASIA_00470 (Las470) | Lectin (orange1.1t05126) |
| | Galactinol-sucrose galactosyltransferase 2-like (Cs9g12460) |
| | DnaJ homolog 1 like (Cs1g19720) |
| | YLS9-like (Cs2g29120) |
| | 8-hydroxygeraniol dehydrogenase (XM_006466284.2) |
| CLIBASIA_04065 (Las4065) | Hypothetical protein (orange1.1t00563) |
| CLIBASIA_05150 (Las5150) | Cysteine protease (Cs4g07410) |
| CLIBASIA_04250 (Las4250) | Translation initiation factor IF-3 (orange1.1g044576m) |

Multiple proteins interacted with CLIBASIA_04025 (Las4025) and CLIBASIA_00470 (Las470); whereas, CLIBASIA_04065 (Las4065), CLIBASIA_05150 (Las5150), and CLIBASIA_04250 (Las4250) each interacted with a single protein. CLIBASIA_04025 (Las4025) interacted with PP2-B2 (orange1.1t04174), a phloem protein. Phloem protein encoding genes are known to be involved in phloem blockage and are suggested to contribute to HLB symptom onset. In addition, SDE15 was shown to interact with the CtACD2 protein by the Y2H assay (FIG. 5A).

To confirm the initial Y2H screen results, full-length sequences of the SDE target proteins were cloned in-frame with the GAL4 activation domain (AD) of the prey vector pGADT7. Following the manufacturer's instructions, the Y2HGOLD yeast strain was co-transformed with relevant bait and prey vector pairs. For negative controls, a prey vector co-transformed with an empty bait vector was used. Exemplary results that were achieved in the Y2H assay using the CLIBASIA_04025 (Las4025) bait vector are shown in FIG. 2. CLIBASIA_04025 (Las4025) interacted with PP2-B2 (orange1.1t04174), and Pathogenesis-related protein 10 (Cs9g03630).

Glutathione S-transferase (GST) pull-down and Bimolecular fluorescence complementation (BiFC) assays were performed to further confirm Y2H results. Las genomic DNA was extracted from infected Citrus leaves and the coding sequences of CLIBASIA_04025 (Las4025), CLIBASIA_00470 (Las470), CLIBASIA_04065 (Las4065), CLIBASIA_05150 (Las5150), and CLIBASIA_04250 (Las4250) were PCR-amplified for use in both assays. For the GST pull-down assay, the respective fragments were cloned in-frame with Maltose-binding protein (MBP) in the pMAL™/C5X vector (NEB, USA) to generate MBP-SDE fusion proteins. The coding sequences of the SDE target proteins were PCR-amplified using Citrus leaf cDNA as a template. The respective fragments were cloned in-frame with GST in the pGEX-4T-1 vector (GE Healthcare, USA) to generate GST-target fusion proteins. For the BiFC assays, the coding sequences of the SDE target proteins were PCR-amplified using Citrus leaf cDNA as a template. The respective SDEs and SDE target proteins were cloned in-frame with either N-terminal or C-terminal fragments of EYFP using pSAT6-nEYFP/C1 and pSAT6/CEYFP/C1-B vectors, respectively. This was done with an In-Fusion cloning kit (Clontech, USA) and produced SDE-EYFPN, EYFPC-SDE, SDE target-EYFPN, and EYFPC-SDE target fusion proteins. Citrus protoplasts isolated from grapefruit epicotyl segments were co-transformed with pairs of EYFPC and EYFPN vectors. Additionally, SDE15 was shown to interact with the CtACD2 protein by the GST pull-down assay (FIG. 5C) and the BiFC assay (FIG. 5B).

Exemplary results obtained in the GST pull-down and BiFC assays are provided in FIG. 3. In both assays, the CLIBASIA_04025 (Las4025) directly interacted with cysteine protease (Cs4g07410), therefore confirming the interaction observed between the two proteins in the Y2H assays. No interactions were detected in any of the negative controls (FIG. 3A and FIG. 3B).

SDE15 was also shown to interact with the CtACD2 protein that negatively regulates the hypersensitive reaction by the hypersensitive response (HR) assay (FIG. 5D). The electrolyte leakage associated with HR induced by AvrBsT protein is shown in FIG. 5E.

Example 3

Overexpression of SDE Target Proteins in Citrus Plants

Figure 4:
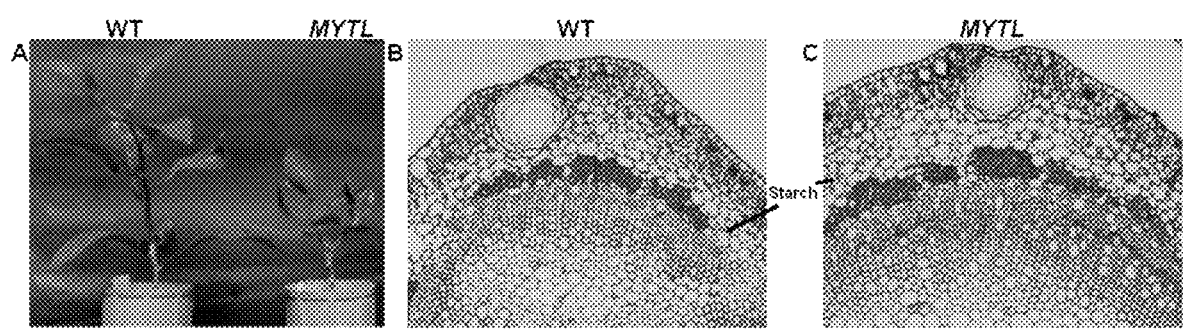

Overexpression of Myb family transcription factor (orange1.1t02260), a CLIBASIA_04025 (Las4025) target protein, in Duncan grapefruits induced symptoms similar to those observed in Citrus plants infected with Candidatus Liberibacter asiaticus. Plants that overexpressed MYTL displayed stunted plant growth and greater starch accumulation when compared to wild type controls (FIG. 4A, FIG. 4B, and FIG. 4C).

Example 4

Mod fection or biolistics, and delivery by expression from a virus. One or more nucleases or gRNA may be used. Donor molecules to deliver the desired changes may include, but are not limited to, double-stranded DNA, single-stranded DNA oligonucleotides, RNA or viral DNA. Donor molecules may be delivered by *Agrobacterium*, virus, biolistic delivery, or transfection. In the presence of a donor template molecule, the one or more DSBs or nicks may then be repaired by homologous recombination between the homology arm(s) of the donor template and the plant genome, by non-homologous end joining (NHEJ), by single-strand annealing pathway or other DNA repair mechanisms resulting in modification of the native sequence in the plant genome to that contained by the donor to create the desired mutation.

Modified *Citrus* plants may be tested for resistance to HLB. *Citrus* plants that are modified to exhibit reduced expression of one or more of the susceptibility genes identified herein may be inoculated with a strain from the genus Ca. *Liberibacter* and evaluated for symptoms of HLB infection compared to *Citrus* plants that do not comprise modified susceptibility genes or regulatory elements thereof. Modified plants that test negative for HLB may be used for further greenhouse and field testing and breeding of HLB resistant *Citrus* lines.

Example 5

Overexpression of SDE15 in *Nicotiana tabacum* and *Citrus*

SDE15 (CLIBASIA_04025, 11.17 kDa) is a hypothetical protein. Sequence analysis of SDE15 did not reveal any insights into its function except the presence of a typical signal peptide (amino acids 1-22) predicted by SignalP v4.1 (FIG. 6A). Interestingly, transgenic expression of SDE15 without the signal peptide (8.68 kDa) in *N. tabacum* caused markedly reduced plant growth and a slightly yellow leaf phenotype, suggestive of biological effects of SDE15 on host biology. These interesting phenotypes, observed in a heterologous plant (*N. tabacum*), prompted us to overexpress SDE15 in the native hostplant *Citrus* (cv. Duncan grapefruit) via stable *Agrobacterium* mediated transformation to determine whether SDE15 is involved in inducing HLB-like symptoms, suppressing plant defenses and/or promoting Las growth. Indeed, SDE15-transgenic Duncan grapefruit plants showed some HLB-like symptoms including slight yellowing, smaller leaves, and reduced growth at the early stage of development (FIG. 6 B). Interestingly, these HLB-like symptoms disappeared approximately one year after transgenic plants were grown under greenhouse conditions.

Las-infected plants show characteristic gene expression patterns (Albrecht, U., and Bowman, K. (2008). PLANT SCIENCE 175, 291-306; Kim, J. S., Sagaram, U. S., Burns, J. K., Li, J. L., and Wang, N. (2009). Phytopathology 99, 50-57; Albrecht, U., and Bowman, K. D. (2012). Plant Sci 185-186, 118-130; Rawat, N., Kiran, S. P., Du, D., Gmitter, F. G., and Deng, Z. (2015). BMC Plant Biol 15, 184). To determine whether SDE15 also modulates host gene expression, we compared the expression patterns of HLB-associated marker genes in SDE15-transgenic and EV (empty vector)-transgenic *Citrus* plants. We found that expression of the genes encoding phloem protein 2 (PP2)-B15, WRKY40, and Zn transporter 5 (ZIP5) was highly induced in SDE15-transgenic *Citrus*, whereas expression of the genes encoding sugar transporter protein Sweet7 and Sweet15 and chalcone synthase were reduced compared to control, resembling those in HLB plants for these marker genes (Albrecht and Bowman, 2008; Kim et al., 2009; Albrecht and Bowman, 2012; Rawat et al., 2015). Taken together, both the partial HLB-like symptom, albeit transient, and the expression pattern of HLB marker genes in the SDE15-transgenic *Citrus* indicate that SDE15 is involved in the outcome of the Las-*Citrus* interaction.

Example 6

Detection of SDE15 Inside Phloem Sap and Subcellular Localization of SDE15

To function as an effector, we expect that SDE15 would be secreted into the cytosol of phloem cells and may be detected in the phloem sap of Las-infected plants. We therefore developed a SDE15-specific antibody and examined whether SDE15 can be detected in the phloem sap by western blot. We could clearly detect SDE15 in the phloem sap extract of Las-infected barks but not in healthy *Citrus* barks by western blot (FIG. 6C). To determine the subcellular locations of SDE15 in the plant cell, we performed subcellular localization of SDE15 by transient expression of SDE15-EYFP fusion protein in *N. benthamiana*. We found that SDE15 is localized to the cytoplasm and the nucleus (FIG. 6D).

We next analyzed the expression pattern of the SDE15 transcript in Las-infected *Citrus* and psyllids using quantitative reverse transcription-PCR (qRT-PCR). SDE15 showed a higher expression level in *Citrus* than in psyllids (FIG. 6E). Furthermore, SDE15 expression level was higher in the early stage (asymptomatic) than the later stage (symptomatic) of Las infection (FIG. 6F), indicating that SDE15 likely functions at a relatively early stage of Las infection before the appearance of visible HLB symptoms.

Example 7

SDE15 Suppresses PCD and Promotes Las Growth in Planta

Many effectors of extracellular pathogens have been reported to suppress plant defenses (Jones, J. D., and Dangl, J. L. (2006). Nature 444, 323-329.; Toruno, T. Y., Stergiopoulos, I., and Coaker, G. (2016). Annu Rev Phytopathol 54, 419-441). To investigate whether SDE15 (from a cytosolic bacterial pathogen) is involved in suppressing plant defenses, we inoculated SDE15-transgenic and nontransgenic Duncan grapefruit with *Xanthomonas citri* subsp. *citri* strain $A^w$ (Xcc$A^w$), which triggers the immunity-associated hypersensitive reaction (HR, a form of PCD) in Duncan grapefruit. Intriguingly, we found Xcc$A^w$ did not induce an HR in the leaves of SDE15-transgenic Duncan grapefruit, whereas an HR was observed in the nontransgenic Duncan grapefruit (FIG. 7A). We next examined immunity-associated gene expression in SDE15 transgenic and nontransgenic plants after inoculation with Xcc$A^w$. The expression of PR1, PR3, and PR5 genes was markedly reduced in the SDE15-transgenic than nontransgenic Duncan grapefruit (FIG. 7B). Taken together, these results suggest that SDE15 is a potent suppressor of PCD in *Citrus*.

The ability of SDE15 to suppress PCD and defense gene expression prompted us to examine whether the SDE15 transgenic plants could promote Las growth. For this purpose, we graft-inoculated SDE15-transgenic and EV-transgenic Duncan grapefruit plants with Las. Significant increase of Las titers was observed over a four-month period in the SDE15-transgenic *Citrus* compared to the EV-transgenic Duncan grapefruit plants, as estimated by qPCR assays (FIG. 8). In accordance, visible HLB symptoms were observed earlier on leaves of SDE15-transgenic *Citrus* than control plants after Las graft-inoculation (FIG. 8).

Because SDE15 suppressed PCD triggered by $XccA^{w}$, we also tested whether SDE15 transgenic plants become more susceptible to virulent Xcc strain XacA 306. Indeed, the canker symptom caused by XacA 306 appeared faster in SDE15 transgenic *Citrus* compared to EV-transgenic plants. In addition, higher XacA 306 populations were detected in SDE15 transgenic grapefruit than that in the EV-transgenic Duncan grapefruit (FIG. 9). Thus, transgenic expression of SDE5 causes broad susceptibility to both HLB and *Citrus* canker, two of the most important diseases in *Citrus*.

Example 8

SDE15 Interacts with the PCD Repressing Protein CsACD2

Because SDE15 does not contain obvious sequence domains that suggest enzymatic activities, we hypothesized that SDE15 might exert its suppressive effect on PCD and defense gene expression via protein-protein interactions. To identify the targets of SDE15, we performed yeast two-hybrid (Y2H) screening with SDE15 without its signal peptide using cDNA libraries generated with mRNAs isolated from the Valencia sweet orange at different Las infection stages (healthy (H), asymptomatic (AS) and symptomatic (S)). We identified 20 SDE15-interacting proteins in the H library, 60 in the AS library and 6 in the S library (Table 1B).

Among the SDE15-interacting proteins identified by Y2H (Table 1B), CsACD2 (Accession No. Cs1g22670) (FIG. 10) was of special interest. It shares 55% similarity with the *Arabidopsis* ACD2 protein (Greenberg et al., 1994; Wuthrich et al., 2000). In *Arabidopsis*, ACD2 protects cells from PCD caused by endogenous porphyrin-related molecules including red chlorophyll catabolite (RCC) or exogenous protoporphyrin IX (Mach, J. M., Castillo, A. R., Hoogstraten, R., and Greenberg, J. T. (2001). T Proc Natl Acad Sci USA 98, 771-776; Yao, N., Eisfelder, B. J., Marvin, J., and Greenberg, J. T. (2004). Plant J 40, 596-610). We hypothesized that SDE15 may target CsACD2 to suppress PCD as a mechanism to promote Las growth in the phloem. We confirmed the SDE15-CsACD2 interaction via pair-wise Y2H assay (FIG. 10A). To further confirm the interaction between SDE15 and CsACD2, we conducted bimolecular fluorescence complementation (BiFC) assay in vivo and glutathione-S-transferase (GST) pull-down assay in vitro. Co-transformation of SDE15-$EYFP^{N}$ and $EYFP^{C}$-CsACD2 or $EYFP^{C}$-SDE15 and CsACD2-$EYFP^{N}$ into *Citrus* leaf protoplasts displayed strong signals in the cytoplasm, but not in negative controls (FIG. 10B GST pull-down assay confirmed direct interaction between GST-SDE15 and MBP-CsACD2 fusion proteins (FIG. 10C). These results demonstrate a genuine interaction between SDE15 and CsACD2.

Example 9

C-Terminal is Essential for SDE15 to Interact with RCCR Domain of CsACD2

To further define the regions of SDE15 and CsACD2 involved in interaction, truncated proteins GST-$SDE15^{\Delta N}$ (SDE15 protein without the signal peptide and additional 25 aa at the N-terminus), GST-$SDE15^{\Delta C}$ (SDE15 protein without the signal peptide and additional 25 aa at the C-terminus) and MBP-RCCR (the RCCR domain of CsACD2 with deletion of 71 aa at the N-terminus) were expressed in *E. coli*, purified and used in GST pull-down assays (FIG. 10D, E). Results showed that the RCCR domain of CsACD2 was sufficient to interact with GST-SDE15 (FIG. 10D). In addition, deletion of the C-terminal, but not the N-terminal of SDE15 abolished its interaction with CsACD2 (FIG. 10E).

Next, we examined the subcellular localization of CsACD2 in *Nicotiana benthamiana* leaf cells. CsACD2 was mostly found in the chloroplast and partially in the cytosol and the nucleus (FIG. 11). Co-localization of SDE15-CFP and CsACD2-EYFP could be detected in the cytoplasm and the nucleus (FIG. 11).

Example 10

SDE15 Promotes the RCCR Activity of CsACD2

It has been shown that ACD2 in *Arabidopsis* represses PCD by functioning as a red chlorophyll catabolite reductase (RCCR) to catalyzing porphyrin-related molecules such as RCC Pruzinski, A., Tanner, G., Aubry, S., Anders, I., Moser, S., Muller, T., Ongania, K. H., Krautler, B., Youn, J. Y., Liljegren, S. J., and Hörtensteiner, S. (2005). Plant Physiol 139, 52-63). To determine whether CsACD2 is involved in SDE15-mediated suppression of PCD, we infiltrated the leaves of *N. benthamiana* with *Agrobacterium* harboring the binary vector that expresses CsACD2-YFP fusion protein and/or SDE15, followed by infiltration with *Agrobacterium* containing a binary vector that expresses AvrBsT 2 days after CsACD2 infiltration (FIG. 12A, B). As expected, AvrBsT triggered an HR in the absence of SDE15 but that HR was repressed in the presence of SDE15. On the other hand, we found neither $SDE15^{\Delta N}$ nor $SDE15^{\Delta C}$ could repress HR induced by AvrBsT. Intriguingly, however, we found that transient overexpression of CsACD2-YFP protein alone was also sufficient to suppress AvrBsT-elicited HR in *N. benthamiana* (FIG. 12A, B), suggesting that (i) SDE15 could interact with the endogenous homolog of ACD2 in *N. benthamiana* (NbACD2 hereinafter) and (ii) it enhances the stability or activity of CsACD2. To test the first possibility, we performed GST pull-down assays. Indeed, SDE15 interacted strongly with NbACD2. As in the case of CsACD2, the NbACD2-YFP fusion protein alone, when transiently expressed, was sufficient to suppress HR induction by AvrBsT. To examine the second hypothesis, we directly performed RCCR activity assay. SDE15 significantly increased the RCCR activity of CsACD2 to catabolize RCC to primary fluorescent catabolite (pFCC), while $SDE15^{\Delta N}$ and $SDE15^{\Delta C}$ lost the ability to promote the RCCR activity of CsACD2 (FIG. 12C).

Example 11

SDE15 Promotes the Chlorophyll Break-Down in Planta

HLB is associated with tissue chlorosis and vein mottling, both are indicative of chlorophyll break down and previous studies have shown that the levels of chlorophyll a and b were significantly reduced in HLB-diseased *Citrus* trees (Killiny, N., and Nehela, Y. (2017). Mol Plant Microbe Interact 30, 543-556). As ACD2 is critical for alleviating the accumulation of toxic intermediates in the chlorophyll breakdown pathway, we surmise that SDE15 promotes the RCCR activity during Las infection by lowering toxic intermediates that induce PCD. We quantified the concentration of pheophorbide a, which is upstream of RCC in the chlorophyll break-down pathway. The concentration of pheophorbide a was significantly lower in the leaves of SDE15 transgenic Citrus than that of the EV transgenic Citrus under HLB-free conditions. In addition, the levels of chlorophyll a and chlorophyll b were also lower in SDE15 transgenic Citrus than those in the EV transgenic Citrus. Furthermore, the concentrations of the three compounds were lower in the leaves of Las-infected Citrus (both SDE15 and EV transgenic plants) than those in the healthy EV transgenic plants. Our results suggest that, by promoting the RCCR activity of CsACD2, SDE15 likely prevents accumulation of PCD-eliciting intermediates during the breakdown of chlorophylls. This activity also likely contributes to the development of yellowing symptom associated with HLB and explained the yellowing symptoms observed in the SDE15 transgenic Citrus (FIG. 6B).

Example 12

Methods For Examples 5-11

Vectors Construction

To generate the construct for plant transformation, Las genomic DNA was isolated from HLB diseased Citrus leaf by CTAB method. The coding sequence of SDE15 (222 bp) without signal peptide was PCR-amplified using gene-specific primers (Table S2). A BamHI recognition sequence and a KpnI recognition site with two protecting nucleotides were added to the 5' end of primers. The PCR product was purified and cloned into pGEM-T Easy vector (Promega, Madison, WI, USA) and then cloned into the binary vector erGFP-1380N at the BamHI and KpnI sites to generate SDE15-overexpression vector. The resulting binary vector was transferred into *Agrobacterium tumefaciens* strain EHA105 and LBA4404 for Citrus and tobacco transformation. Empty Vector (EV) without SDE15 fragment was used for Citrus and tobacco transformation as negative controls.

For Y2H, the coding region of SDE15 (minus the putative signal peptide) was amplified and cloned in-frame with the GAL4 DNA-binding domain (BD) of the bait vector pGBKT7 to generate BD-SDE15 for Y2H library screening and co-transformation in yeast. The 996 bp coding sequence of CsACD2 was PCR-amplified from Citrus leaf cDNA and cloned in-frame with the GAL4 DNA-activating domain (AD) of the prey vector pGADT7 to generate AD-CsACD2 for co-transformation with bait vector in yeast to confirm the interaction. BD and AD vectors were constructed by using the In-Fusion cloning kit (Clontech, Mountain View, CA, USA).

Transient expression in Citrus protoplast were used for subcellular localization and BiFC assays. For the subcellular localization assay, the coding region of SDE15 without signal peptide was inserted into EcoRI-digested C-terminal EYFP containing vector pSAT6-EYFP-N1 by using In-Fusion cloning kit to generate SDE15-EYFP fusion proteins. For the BiFC assay, SDE15 and CsACD2 were inserted into SalI-digested BiFC vectors pSAT6-nEYFP-C1 and pSAT6-cEYFP-C1-B by using In-Fusion cloning kit to produce SDE15-EYFP$^N$, EYFP$^C$-SDE15, CsACD2-EYFP$^N$ and EYFP$^C$-CsACD2 fusion proteins. All the vectors were subsequently used for Citrus protoplast transformation.

To generate recombinant protein constructs for GST pull-down assay and red chlorophyll catabolite reductase (RCCR) assay, the coding region of SDE15 (without signal peptide) was inserted between EcoRI and XhoI sites of pGEX-4T-1 vector (GE Healthcare, Chicago, IL, USA) to generate GST-SDE15 fusion protein vector as bait. The coding sequence of CsACD2 was inserted between BamHI and EcoRI sites of pMAL™-c5X vector (NEB, Ipswich, MA, USA) to generate MBP-CsACD2 fusion protein vector as prey and source of RCCR for enzyme assay. The truncated sequences of SDE15 fragments (SDE15$^{\Delta N}$ and SDE15$^{\Delta C}$) were inserted into EcoRI-digested pGEX-4T-1 vector by using In-Fusion cloning kit to generate GST-SDE15$^{\Delta N}$ and GST-SDE15$^{\Delta C}$ fusion protein vectors as bait. The coding sequence of RCCR domain of CsACD2 was amplified and inserted between BamH I and EcoRI sites of pMAL™-c5X vector by using In-Fusion cloning kit to generate MBP-RCCR fusion protein vector as prey.

To generate the constructs for agro-infiltration assay in *N. benthamiana*, modified pCambia1380 vectors were constructed by inserting cauliflower mosaic virus promoter (CaMV 35S) and EYFP/CFP coding sequence to create the transient expression vectors with C-terminal EYFP reporter protein (pCambia1380-35S-EYFP) or C-terminal CFP reporter protein (pCambia1380-35S-CFP). The coding sequence of SDE15 without signal peptide was PCR-amplified and inserted between BamH I and Kpn I sites of pCambia1380-35S-EYFP and pCambia1380-35S-CFP to generate 35S-SDE15-EYFP and 35S-SDE15-CFP individually. The truncated sequences of SDE15 fragments (SDE15$^{\Delta N}$ and SDE15$^{\Delta C}$) were inserted between BamH I and Kpn I sites of pCambia1380-35S-EYFP by using In-Fusion cloning kit to generate 35S-SDE15$^{\Delta N}$-EYFP and 35S-SDE15$^{\Delta C}$-EYFP. The coding sequence of CsACD2 was inserted between BamH I and Kpn I sites of pCambia1380-35S-EYFP to generate 35S-CsACD2-EYFP vector. The coding sequence of NbACD2 was inserted between BamH I and Kpn I sites of pCambia1380-35S-EYFP by using In-Fusion cloning kit to generate 35S-BenACD2-EYFP vector. All the vectors were then transferred into *Agrobacterium tumefaciens* strain GV2260 for agro-infiltration assay.

All the primers used for vector construction were listed in Table S2.

TABLE S2

| | primers used for vector construction | |
|---|---|---|
| | Forward (5'-3') | Reverse (5'-3') |
| SDE15-OE | GGGGATCCATGGATACTCTCTCTGACTC | GGGGTACCTCTTTCCCATTCTCTAAC |
| BD-SDE15 | CATGGAGGCCGAATTCATGGATACTCTCTCTGACTC | GGATCCCCGGGAATTCTCTTTCCCATTCTCTAAC |
| AD-CsACD2 | GGAGGCCAGTGAATTCATGGCTGTGAACCACTTATG | CACCCGGGTGGAATTCGGCAGTAAAAACCTTCTGTA |

TABLE S2-continued primers used for vector construction

| | Forward (5'-3') | Reverse (5'-3') |
|---|---|---|
| SDE15-BiFC | GAATTCTGCAGTCGACATGGATACTCTCTCTGACTC | CCGCGGTACCGTCGACTCTTTCCCATTCTCTAAC |
| CsACD2-BiFc | GAATTCTGCAGTCGACATGGCTGTGAACCACTTATG | CCGCGGTACCGTCGACGGCAGTAAAAACCTTCTGTA |
| GST-SDE15 | GGGAATTCATGGATACTCTCTCTGACTC | GGCTCGAGTCTTTCCCATTCTCTAAC |
| GST-SDE15$^{\Delta N}$ | TGGATCCCCGGAATTCATGGACGACTCCCATAATCAA | GTCGACCCGGGAATTCTCTTTCCCATTCTCTAAC |
| GST-SDE15$^{\Delta C}$ | TGGATCCCCGGAATTCATGGATACTCTCTCTGACTC | GTCGACCCGGGAATTCTATATTGTTCTTTATCTTTAT |
| MBP-CsACD2 | TATCGTCGACGGATCCATGGCTGTGAACCACTTATG | TACCTGCAGGGAATTCGGCAGTAAAAACCTTCTGTA |
| MBP-RCCR | TATCGTCGACGGATCCATGCCTGTTAGGCAGCTGAT | TACCTGCAGGGAATTCGGCAGTAAAAACCTTCTGTA |
| MBP-NbACD2 | TATCGTCGACGGATCCATGGCTATTTCAATATCCT | TACCTGCAGGGAATTCAGCATTGTAGATTTCCC |
| SDE15-YFP | TTGGATCCATGGATACTCTCTCTGACTC | GGGGTACCTCTTTCCCATTCTCTAAC |
| SDE15-CFP | TTGGATCCATGGATACTCTCTCTGACTC | GGGGTACCTCTTTCCCATTCTCTAAC |
| SDE15$^{\Delta N}$-EYFP | GGACTCTAGAGGATCCATGGACGACTCCCATAATCAA | CCCTTGCTCACCATGGTACCTCTTTCCCATTCTCTAAC |
| SDE15$^{\Delta C}$-EYFP | GGACTCTAGAGGATCCATGGATACTCTCTCTGACTC | CCCTTGCTCACCATGGTACCTATATTGTTCTTTATCTTTAT |
| CsACD2-YFP | TTGGATCCATGGCTGTGAACCACTTATG | GGGGTACCGGCAGTAAAAACCTTCTGTA |
| NbACD2-YFP | GGACTCTAGAGGATCCATGGCTATTTCAATATCCT | CCCTTGCTCACCATGGTACCAGCATTGTAGATTTCCC |

*Nucleotides underline is the restriction enzyme cutting site

Transient Gene Expression in *Citrus* Protoplasts

Protoplasts were isolated from etiolated Duncan grapefruit epicotyl segments by following the protocol of transient gene expression in *Arabidopsis* mesophyll protoplasts with modifications (Yoo, S. D., Cho, Y. H., and Sheen, J. (2007). Nat Protoc 2, 1565-1572). Briefly, epicotyl segments of Duncan grapefruit cultured in dark were cut to small pieces and digested in Cellulose "Onozuka" R-10 and MACEROZYME R-10 (Yakult Pharmaceutical, Japan) enzyme solution overnight. Protoplasts were harvested and used for plasmid transformation. Plasmids were transformed into *Citrus* protoplasts by the polyethylene glycol 4000 (PEG4000)-mediated transformation method (Citovsky, V., Lee, L. Y., Vyas, S., Glick, E., Chen, M. H., Vainstein, A., Gafni., Gelvin, S. B., and Tzfira, T. (2006). J Mol Biol 362, 1120-1131; Lee, L. Y., Fang, M. J., Kuang, L. Y., and Gelvin, S. B. (2008). Plant Methods 4, 24). For the BiFC assay, the coding sequence of SDE15 without signal peptide and full-length CsACD2 were cloned into either N-terminal or C-terminal fragments of EYFP vectors pSAT6-nEYFP-C1 and pSAT6-cEYFP-C1-B (Citovsky et al., 2006). The combinations of SDE15-EYFP$^N$/EYFP$^C$-CsACD2 and CsACD2-EYFP$^N$/EYFP$^C$-SDE15 were transiently co-transformed into protoplasts. Other combinations, such as SDE15-EYFP$^N$/EYFP$^C$, EYFP$^N$/EYFP$^C$-SDE15, SDE15-EYFP$^N$/EYFP$^C$-SDE15, CsACD2-EYFP$^N$-/EYFP$^C$, EYFP$^N$/EYFP$^C$-CsACD2, CsACD2-EYFP$^N$/EYFP$^C$-CsACD2, EYFP$^N$/EYFP$^C$ were also transformed into *Citrus* protoplasts as controls. After incubation in dark overnight, the EYFP signals were examined and photographed under a fluorescence microscope for BiFC assay with excitation wavelength 514 nm (Olympus, Tokyo, Japan).

Plant Transformation and Pathogen Inoculation

*Agrobacterium* mediated transformation of etiolated epicotyl segments of Duncan grapefruit were carried out as described previously (Orbović, V., and Grosser, J. W. (2015). Methods Mol Biol 1224, 245-257). *Agrobacterium tumefaciens* EHA105 harboring the recombinant plasmid was used for *Citrus* transformation. Transgenic lines showing kanamycin-resistance and erGFP-specific fluorescence were selected and then micro-grafted in vitro onto 1-month old Carrizo citrange nucellar rootstock seedlings. After a month of growth in vitro, the grafted shoots were potted into a peat based commercial potting medium and acclimated under greenhouse conditions.

*N. tabacum* cv. Petite Havana SR1 seeds were sown on MS medium (Sigma-Aldrich, St. Louis, MO, USA) containing 3% sucrose and 0.8% agar and allowed to germinate at 22±1° C. (16 h light and 8 h darkness). Subsequently, plants were grown and maintained in MS medium. Fresh tobacco leaf discs were infected with *A. tumefaciens* strain LBA4404 harboring the recombinant plasmid. The regenerated shoots were maintained on MS medium supplemented with 0.2 mg L$^{-1}$ NAA and 3 mg L$^{-1}$ 6-BA along with 100 mg L$^{-1}$ kanamycin and 500 mg L$^{-1}$ cephotaxime. Kanamycin-resistant, erGFP and PCR positive shoots of T0 transgenic plants were selected, transferred to the greenhouse and maintained up to T2 generations, which were used for phenotype inspection and further analysis.

For the HLB pathogenicity assay, the SDE15-transgenic and EV-transgenic trees was inoculated with Las via grafting as previously reported (Li, J., Pang, Z., Trivedi, P., Zhou, X., Ying, X., Jia, H., and Wang, N. (2017). Mol Plant Microbe Interact 30, 620-630). Midrib DNA was isolated from the grafted trees monthly after grafting up to 4-month post grafting and used to quantify Las by Taqman qPCR with Primer/probe combination (CQULA04F-CQULAP10-CQULA04R) as described previously (Wang, Z., Yin, Y., Hu, H., Yuan, Q., Peng, G., and Xia, Y. (2006). Plant Pathology 55, 630-638). The Ct value of each amplicon represents the Las genomic copy numbers in 100 ng *Citrus* midrib DNA. The test was repeated three times.

For the *Xanthomonas citri* subsp. *citri* (Xcc) pathogenicity and hypersensitive reaction (HR) assays in *Citrus*, SDE15-transgenic and non-transgenic Duncan grapefruit plants were used for inoculation in a quarantine greenhouse. The wild-type strain Xac306 causes disease on grapefruit whereas the Xcc A$^w$ strain triggers hypersensitive reaction in grapefruit leaves[7]. Xcc strains were grown with shaking overnight at 28° C. in NB, centrifuged down, and suspended in sterile tap water, and the concentrations were adjusted to 10$^6$ CFU/ml (for Xac306) and 10$^8$ CFU/ml (for Xcc A$^w$) individually. Bacterial solution was infiltrated into fully expanded, immature leaves with needleless syringes (Yan, Q., and Wang, N. (2012). Mol Plant Microbe Interact 25, 69-84.). The tests were repeated three times with similar results. Disease symptoms and HR phenotype were photographed at 3, 5, 7, 9 and 11 days post inoculation. Growth curve assay of Xac 306 was conducted at 0, 1, 3, 5, 7, 9 and 11 days post inoculation.

Agro-Infiltration Assay in *N. benthamiana*

*A. tumefaciens* strain GV2260 cells containing binary vectors were cultured overnight in LB medium with 50 μg ml$^{-1}$ of rifampicin and 50 μg ml$^{-1}$ kanamycin and re-suspended in induction medium (10 mM MgCl2, 10 mM MES pH 5.6, 200 uM acetosyringone), and incubated at 25° C. with shaking for 4 h. The cultures were diluted to OD600 of 0.1 or 0.2. For each vector, three leaves of young *N. benthamiana* plants were infiltrated with diluted *A. tumefaciens* suspension as triplicates.

For the HR assay, young leaves of *N. benthamiana* were first infiltrated with *A. tumefaciens* cells containing binary vectors for SDE15-EYFP and/or CsACD2-EYFP by using a needleless syringe, kept in a greenhouse for 2 days and then infiltrated with another *A. tumefaciens* strain harboring the binary vector carrying the AvrBsT protein which can trigger HR as reported previously Kim, N. H., Choi, H. W., and Hwang, B. K. (2010). Mol Plant Microbe Interact 23, 1069-1082). Agro-infiltrated plants were kept in a greenhouse and HR were examined and photographed at 3 days post AvrBsT inoculation. For the electrolyte leakage assay, leaf discs of AvrBsT infiltrated plants at 2 days post infiltration were floated on deionized water with shaking. The conductivity of the solution was measured 4 h later using an Oakton™ Conductivity Benchtop Meters (Thermo Fisher, Waltham, MA, USA). The *A. tumefaciens* transformant cells harboring an empty vector were infiltrated into the leaves of *N. benthamiana* as controls.

For the localization and co-localization assay, CsACD2-EYFP was co-expressed with the plasma membrane localization-marker PM-CFP, the nucleus-marker CFP-nucleus or SDE15-CFP in leaves of *N. benthamiana*. *A. tumefaciens* strain GV2260 harboring the corresponding plasmids were infiltrated into leaves at OD600 of 0.2. Subcellular localization was inspected and photographed 1 day post infiltration.

Extraction of Phloem Sap Proteins

An optimized method of protein extraction from phloem sap was performed by combining two methods reported before (Hijaz, F., and Killiny, N. (2014). Collection and chemical composition of phloem sap from *Citrus sinensis* L. Osbeck (sweet orange). PLoS One 9, e101830; O'Leary, B. M., Rico, A., McCraw, S., Fones, H. N., and Preston, G. M. (2014). J Vis Exp.). Briefly, 10-20 cm (0.5 cm diameter) stems from Las infected and uninfected trees were collected. The bark area was stripped into two pieces and was manually removed from the twig. The inner part of the bark was rinsed with deionized water and dried with Kim wipes. Then the bark strips were cut into about 1-cm pieces using a sterile razor blade and placed in a 60-mL syringe filled with distilled water. Vacuum was applied for 5-15 seconds repeatedly to let water penetrated barks. Then the barks were dried with Kim wipes and placed in a 20-mL syringe, centrifuged in 50 mL falcon tube for 10 min at 4,000 g, at 4° C. The collected phloem sap was centrifuged at 15,000 g for 5 min. The supernatant was heating for 5 min at 95° C. in SDS gel-loading buffer for SDE15 detection with specific antibody.

RNA Isolation and Expression Analysis of HLB Associated Genes qRT-PCR was performed to detect the expression of SDE15 in SDE15-transgenic plants (both in *Citrus* and tobacco) and in non-transgenic *Citrus* plants and psyllids. We also examined the expression of HLB marker genes in the SDE15-transgenic *Citrus* and PR genes in SDE15-transgenic plants after HR induction. Total RNA of transgenic *Citrus*, transgenic tobacco and psyllids were extracted by Trizol reagent (Thermo Fisher) and digested with DNase I (Promega) followed by the manufacturers' instructions. First-strand cDNA was synthesized from purified RNA with ImProm-II™ Reverse Transcription System (Promega) and diluted 10 times for RT-qPCR to detect related genes with specific primers (Table S3). 20 μl of qPCR reaction consisted of 10 μl of 2×KiCqStart® SYBR® Green qPCR ReadyMix™ (Sigma-Aldrich), 1 μl of each primer (5 μM), 2 μl of diluted cDNA template, and 6 μl of DNase/RNase free water. The PCR cycling consisted an initial activation step at 95° C. for 3 min, followed by 40 cycles of 95° C. for 15 s and 60° C. for 40 s. All cDNA samples were run in triplicates. *Citrus* GAPDH gene, tobacco Actin gene and Las gyrA gene were used as endogenous controls wherever appropriate.

The qPCR primer sequences of specific genes and endogenous control genes are listed in Table S3.

TABLE S3 primers used for qRT-PCR and Taqman probe PCR analysis

| | Forward (5'-3') | Reverse (5'-3') |
|---|---|---|
| qSDE15 | ACTCCCATAATCAAAAGCCTACG | CGTATCTTTCACCATTCCATCCTC |
| qCsACD2 | GGCTAAATCAGTGTGCTTGTG | ATCAACCCATCCCTCTTTTCC |
| PR1 | AAATGTGGGTGAATGAGAAAGC | ATTATTGTTGCACGTCACCTTG |
| PR2 | TTCCACTGCCATCGAAACTG | GTAATCTTGTTTAAATGAGCCTCTTG |
| PR3 | GGCTCAAACTTCACATGAAACTAC | GTTGACAATAATCTCCAGGGTTTC |
| PR5 | CACCATTGCCAATAACCCTAATG | GGGACAGTTACCGTTAAGATCAG |
| PP2-B15 | TCGTTGCCATCAGAAGTATCAC | CCAACGCAAATAAACTGTCCC |

TABLE S3-continued primers used for qRT-PCR and Taqman probe PCR analysis

| | Forward (5'-3') | Reverse (5'-3') |
|---|---|---|
| WRKY40 | CTCCTGTTCCAAATGCCAAG | CCGAGGTGAGGGATTATCTTTAG |
| ZIP5 | TGAATATGCTGGTGAATCGGAG | GCTGCAACCAAAGGCTTAATAG |
| Sweet7 | GCTAACCCTACTTCACTCCAC | GGCATATACTCCACGCTCTTG |
| Sweet15 | GTGTTGCCGTTTCTGTTAGTG | GCGAACCACATAATTGCACTC |
| Chalcone synthase | GCGTTCTAGTCGTATGCTCTG | GCCAATGATTAAAGCTGCGG |
| CsGAPDH | GGAAGGTCAAGATCGGAATCAA | GGAAGGTCAAGATCGGAATCAA |
| NbActin | CCTGAGGTCCTTTTCCAACCA | GGATTCCGGCAGCTTCCATT |
| gryA | CAATGTGCTGGTCAATGGTG | AATCTCCATCAAGGCATCCAG |
| CQULA04 (β operon primer) | TGGAGGTGTAAAAGTTGCCAAA | CCAACGAAAAGATCAGATATTCCTCTA |
| CQULAP10 (β operon probe, 5'-3') | FAM-TCGTCTCGTCAAGATTGCTATCCGTGATACTAG-TAMRA | |

Yeast Two-Hybrid Library Screening and Interaction Analysis

Total RNA was extracted from leaves of Valencia sweet orange (HLB symptomatic (S, Las Ct value 25-26 per 100 ng DNA), HLB asymptomatic (AS, Las Ct value 28-30 per 100 ng DNA) and healthy (H, Las free)) by Trizol reagent (Thermo Fisher), digested by DNase I (Promega). mRNA samples were purified using the NucleoSpin® RNA kit (Clontech). ALL three types of mRNA samples were used to construct yeast two-hybrid libraries in the pGADT7-Rec vector using the Make Your Own "mate and plate" library system (Clontech) following the manufacturer's instructions and transformed in the yeast strain Y187 by using Yeastmaker™ Yeast Transformation System 2 (Clontech). The titer of each constructed library is more than $3 \times 10^8$ which represents the good transformation efficiency. BD:SDE15 construct was transformed into Y2HGOLD yeast strain (Clontech) Library screening was performed according to the Matchmaker Gold yeast two-hybrid system protocol (Clontech). Standard positive controls (pGBKT7-53 and pGADT7-T; Clontech) and standard negative control (pGBKT7-Lam and pGADT7-T) were included. After mating between the Gold strain transformed with BD:SDE15 and the Y187 libraries, diploid yeasts were plated on synthetic dropout (SD)/-Leu/-Trp (DDO), SD/-Leu/-Trp/-Ade/-His (QDO) and SD/-Leu/-Trp/-Ade/-His plus X-α-gal and Aureobasidin A (AbA) (QDO/A/X) agar plates to detect the activation of reporter genes HIS3, ADE2, MEL1 (for α-galactosidase activity) and AbA$^r$ (for Aureobasidin A resistance). The fragments of positive diploid yeast were amplified by colony PCR with Matchmaker® Insert Check PCR Mix 2 (Clontech) and analyzed by electrophoresis on a 0.8% TAE Agarose/EtBr gel. The PCR products with single band were purified and sent for sequencing. The PCR products with multiple bands indicate the presence of more than one prey plasmid in a heterozygote cell. For this situation, plasmids were isolated from the heterozygote cells with multiple plasmids with Easy Yeast Plasmid Isolation Kit (Clontech) and transferred into E. coli for sequencing. BLAST was used to compare the inserts nucleotide sequences to the genome of sweet orange to identify corresponding proteins which interact with SDE15.

Recombinant Proteins Expression and GST Pull-Down Assay

E. coli cells expressing GST or GST fusion proteins were washed in PBS buffer and suspended with CelLytic B Cell Lysis Reagent (Sigma-Aldrich) to generate the cell lysates. After centrifugation, the cell lysates were incubated with glutathione agarose beads in accordance with the GST Protein Interaction Pull-Down Kit instructions (Thermo Scientific). The beads were washed to remove the unbound proteins and incubated with E. coli cell lysates expressing either MBP or MBP fusion protein for 1 to 2 h at 4° C. After washing four times, the beads were eluted with 10 mM glutathione, and the eluates were collected and immunoblotted using anti-MBP (NEB) and anti-GST (Abcam, Cambridge, UK) antibodies.

Enzyme Assays

Coupled Pheophorbide a oxygenase (PaO)/RCCR assay was performed to test CsACD2 activity according to published procedures (Hortensteiner, S., Vicentini, F., and Matile, P. (1995). Chlorophyll breakdown in senescent cotyledons of rape, Brassica napus L.: Enzymatic cleavage of phaeophorbide a in vitro. New Phytol. 129, 237-246; Withrich, K. L., Bovet, L., Hunziker, P. E., Donnison, I. S., and Hörtensteiner, S. (2000). Plant J 21, 189-198; Pruzinski et al., 2005). Thylakoids containing PaO were isolated and solubilized from senescent Citrus leaves as described previously (Hortensteiner et al., 1995). PaO was partially purified from solubilized membranes and used for enzyme assay (Rodoni, S., Vicentini, F., Schellenberg, M., Matile, P., and Hortensteiner, S. (1997). Plant Physiol 115, 677-682.). MBP-CsACD2 fused protein was expressed and purified with the pMAL protein fusion & purification system (NEB) as the source of RCCR. Briefly, assays (total volume of 50 μl) contained different combinations of PaO (equivalent to 0.5 g of tissue), E. coli (50 μg) protein extracts as a source of RCC-forming factor (RFF), and purified MBP-CsACD2 (1.5 μg) as the source of RCCR. The assays were supplemented with 0.5 mM pheide a, 10 μg ferredoxin (Fd), and a Fd-reducing system consisting of 2 mM Glc-6-P, 1 mM NADPH, 50 milliunits of Glc-6-P dehydrogenase, and 5 milliunits of Fd-NADP$^+$ oxidoreductase. After 1 hour incubation at 25° C., reactions were terminated by the addition of 80 mL methanol. Formation of primary fluorescent chlorophyll catabolite (pFCC) was followed by reversed-phase HPLC with 36% (v/v) 50 mM potassium phosphate buffer, pH 7.0, in methanol as solvent. Activities are determined as integrated fluorescence units (320/450 nm) of pFCCs.

Quantification of Compounds Participating Chlorophyll Break-Down Pathway

Three compounds (chlorophylls a, b and pheophorbide a) in Chlorophyll break-down pathway were extracted and quantified as previously descripted (Garrido, J. L., Rodríguez, F., Campaña, E., and Zapata, M. (2003). J Chromatogr A 994, 85-92.), with modification. Briefly, leaf samples of SDE15 transgenic *Citrus*, EV transgenic *Citrus*, SDE15 transgenic *Citrus* infected with HLB and EV transgenic *Citrus* infected with HLB were collected and homogenized with 8 ml of 90% acetone and left for 16 hours at −10° C. All extracts were filtered through 25 mm, 0.2 m GHP Acrodisc filters (Sigma-Aldrich) prior to injection. All sample preparations were done under subdued light. The standards of chlorophylls a, b and pheophorbide a were obtained from Sigma-Aldrich. All the standards and samples were followed by reversed-phase HPLC. Mobile phase consisted of (A) methanol, (B) 0.025M ammonium acetate and (C) acetone. A linear gradient from A-B (80:20, v/v) to A-C (80:20, v/v) was pumped during 15 min, followed by an isocratic hold at A-C (80:20, v/v) during a further 5 min. The flow-rate was 1 ml/min.

What is claimed is:

1. A plant comprising plant cells comprising a modification to an endogenous gene, wherein the polypeptide encoded by the endogenous gene interacts with a Sec-dependent effector (SDE) secreted by a bacterial species from the genus Ca. *Liberibacter*, wherein the modification knocks-down or reduces expression of the endogenous gene and/or interrupts interaction of the polypeptide with the SDE and confers resistance or tolerance to Ca *Liberibacter* infection in the plant relative to a plant of the same variety lacking the modification, and wherein the endogenous gene comprises at least one of SEQ ID NO: 16, 18, 20, 44, 45, or 51, or a sequence comprising at least 95% identity therewith, and wherein the SDE is Las4025, and the modification comprises a modification to the endogenous gene comprising:

insertion of at least 1 nucleotide, a deletion of at least 1 nucleotide, and/or a substitution of at least 1 nucleotide.

2. The plant of claim 1, wherein the plant is *Citris.*

3. The plant of claim 1, wherein the plant is a solanaceous plant.

4. The plant of claim 3, wherein the plant is *Solanum tuberosum.*

5. The plant of claim 1, wherein the plant is a grapefruit tree, an orange tree, a sweet orange tree, a lime tree, citrumelo tree, trifoliate tree, *reticulata* tree, aurantiuma tree, lemon tree, a papeda tree, a pummelo tree or a mandarin orange tree.

6. A seed that produces the plant of claim 1.

7. A plant part of the plant of claim 1, wherein the plant part comprises the modification.

8. A method of generating a modified *Citrus* or solanaceous plant comprising resistance or tolerance to infection by a bacterial species from the genus Ca. *Liberibacter*, the method comprising the steps of:

(a) modifying an endogenous gene of a *Citrus* or solanaceous plant cell such that expression of the endogenous gene is knocked-down or reduced and/or interaction of the polypeptide encoded by said endogenous gene with a Sec-dependent effector (SDE) secreted by a bacteria species from the genus Ca. *Liberibacter* is reduced, wherein the endogenous gene is SEQ ID NO: 16, 18, 20, 44, 45, or 51, or a sequence comprising at least 95% identity therewith, and wherein the SDE is Las4025; and (b) regenerating the modified plant from said plant cell or a progenitor cell thereof, wherein said the plant comprises said modification.

9. The method of claim 8, wherein the plant is *Citrus.*

10. The method of claim 9, wherein the plant is a solanaceous plant.

11. A plant comprising resistance to Ca. *Liberibacter* infection produced by the method of claim 10.

12. The method of claim 8, effects of a Sec-dependent effector (SDE) secreted by a bacteria species from the genus Ca. *Liberibacter* are reduced.

13. The method of claim 8, wherein step (a) comprises a genome-editing technique.

14. The method of claim 13, wherein the genome-editing technique comprises a use of a nuclease, wherein the nuclease introduces a single-strand DNA break or a double-strand DNA break.

15. The method of claim 13, wherein the genome-editing technique comprises use of a Talen, a ZFN, meganuclease, or a CRISP/Cas system.

* * * * *